(12) United States Patent
Ladtkow et al.

(10) Patent No.: US 9,259,269 B2
(45) Date of Patent: *Feb. 16, 2016

(54) MICROWAVE ABLATION CATHETER AND METHOD OF UTILIZING THE SAME

(71) Applicant: Covidien LP, Mansfield, MA (US)

(72) Inventors: Casey M. Ladtkow, Erie, CO (US);
Joseph D. Brannan, Erie, CO (US);
Darion R. Peterson, Boulder, CO (US);
Eric W. Larson, Thornton, CO (US);
Kaylen J. Haley, Westminster, CO (US);
William J. Dickhans, Longmont, CO (US); Jason A. Case, Longmont, CO (US)

(73) Assignee: Covidien LP, Mansfield, MA (US)

( * ) Notice: Subject to any disclaimer, the term of this patent is extended or adjusted under 35 U.S.C. 154(b) by 340 days.

This patent is subject to a terminal disclaimer.

(21) Appl. No.: 13/836,519

(22) Filed: Mar. 15, 2013

(65) Prior Publication Data

US 2014/0046174 A1   Feb. 13, 2014

Related U.S. Application Data

(60) Provisional application No. 61/680,555, filed on Aug. 7, 2012, provisional application No. 61/783,921, filed on Mar. 14, 2013, provisional application No. 61/784,048, filed on Mar. 14, 2013, provisional
(Continued)

(51) Int. Cl.
*A61B 18/04* (2006.01)
*A61B 18/18* (2006.01)
(Continued)

(52) U.S. Cl.
CPC ............ *A61B 18/1815* (2013.01); *A61B 1/018* (2013.01); *A61B 5/01* (2013.01);
(Continued)

(58) Field of Classification Search
CPC .... A61B 18/18; A61B 18/1815; A61B 10/04; A61B 1/2676; A61B 2019/2211; A61B 2019/2219
See application file for complete search history.

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CN | 1103807 A | 6/1995 |
| DE | 390937 C | 3/1924 |

(Continued)

OTHER PUBLICATIONS

U.S. Appl. No. 13/419,981, filed Mar. 14, 2012, Joseph D. Brannan.
(Continued)

*Primary Examiner* — Robert N Wieland

(57) ABSTRACT

A microwave ablation system configured for use in luminal network is provided. The microwave ablation system includes a microwave energy source. A tool for treating tissue is provided with the microwave ablation system. An extended working channel is configured to provide passage for the tool. A locatable guide catheter is positionable through the extended working channel and configured to navigate the extended working channel adjacent the target tissue. The microwave ablation system includes a navigation system that is configured for guiding the tool, extended working channel or the locatable guide through a luminal network following a predetermined determined pathway to the target tissue. One or more imaging modalities may be utilized for confirming placement of the tool within target tissue.

32 Claims, 39 Drawing Sheets

Related U.S. Application Data application No. 61/784,176, filed on Mar. 14, 2013, provisional application No. 61/784,297, filed on Mar. 14, 2013, provisional application No. 61/784,407, filed on Mar. 14, 2013.

(51) Int. Cl.

| | | |
|---|---|---|
| *A61B 6/12* | (2006.01) | |
| *A61B 5/01* | (2006.01) | |
| *A61B 6/03* | (2006.01) | |
| *A61B 10/02* | (2006.01) | |
| *A61B 10/04* | (2006.01) | |
| *A61B 10/06* | (2006.01) | |
| *A61B 5/11* | (2006.01) | |
| *A61B 1/018* | (2006.01) | |
| *A61B 6/00* | (2006.01) | |
| *A61B 1/267* | (2006.01) | |
| *A61B 5/053* | (2006.01) | |
| *A61B 5/00* | (2006.01) | |
| *A61B 5/06* | (2006.01) | |
| *A61B 18/00* | (2006.01) | |

(52) U.S. Cl.
CPC ............ *A61B 5/1114* (2013.01); *A61B 6/032* (2013.01); *A61B 6/12* (2013.01); *A61B 6/487* (2013.01); *A61B 10/0233* (2013.01); *A61B 10/04* (2013.01); *A61B 10/06* (2013.01); *A61B 1/2676* (2013.01); *A61B 5/0538* (2013.01); *A61B 5/062* (2013.01); *A61B 5/064* (2013.01); *A61B 5/4836* (2013.01); *A61B 5/7425* (2013.01); *A61B 5/7445* (2013.01); *A61B 2010/0216* (2013.01); *A61B 2018/00577* (2013.01); *A61B 2018/1861* (2013.01)

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,583,589 A | 4/1986 | Kasevich | |
| D295,893 S | 5/1988 | Sharkany et al. | |
| D295,894 S | 5/1988 | Sharkany et al. | |
| 5,301,687 A | 4/1994 | Wong et al. | |
| 5,370,644 A | 12/1994 | Langberg | |
| D354,218 S | 1/1995 | Van de Peer | |
| 5,545,137 A | 8/1996 | Rudie et al. | |
| 5,603,697 A | 2/1997 | Grundy et al. | |
| 5,624,392 A | 4/1997 | Saab | |
| 5,693,082 A | 12/1997 | Warner et al. | |
| 5,741,249 A | 4/1998 | Moss et al. | |
| 5,980,505 A | 11/1999 | Wilson | |
| 5,993,447 A | 11/1999 | Blewett et al. | |
| 5,995,875 A | 11/1999 | Blewett et al. | |
| 6,014,581 A | 1/2000 | Whayne et al. | |
| D424,693 S | 5/2000 | Pruter | |
| D424,694 S | 5/2000 | Tetzlaff et al. | |
| D425,201 S | 5/2000 | Tetzlaff et al. | |
| 6,061,551 A | 5/2000 | Sorrells et al. | |
| 6,106,524 A | 8/2000 | Eggers et al. | |
| 6,117,101 A | 9/2000 | Diederich et al. | |
| 6,139,527 A | 10/2000 | Laufer et al. | |
| 6,186,978 B1 | 2/2001 | Samson et al. | |
| 6,188,355 B1 | 2/2001 | Gilboa | |
| 6,210,367 B1 | 4/2001 | Carr | |
| 6,235,024 B1 | 5/2001 | Tu | |
| 6,277,113 B1 | 8/2001 | Berube | |
| D449,886 S | 10/2001 | Tetzlaff et al. | |
| 6,355,016 B1 | 3/2002 | Bagaoisan et al. | |
| D457,958 S | 5/2002 | Dycus et al. | |
| D457,959 S | 5/2002 | Tetzlaff et al. | |
| 6,398,781 B1 | 6/2002 | Goble et al. | |
| 6,485,486 B1 | 11/2002 | Trembly et al. | |
| 6,496,737 B2 | 12/2002 | Rudie et al. | |
| 6,496,738 B2 | 12/2002 | Carr | |
| 6,514,249 B1 | 2/2003 | Maguire et al. | |
| 6,547,788 B1 | 4/2003 | Maguire et al. | |
| 6,599,288 B2 | 7/2003 | Maguire et al. | |
| 6,629,951 B2 | 10/2003 | Laufer et al. | |
| 6,629,974 B2 | 10/2003 | Penny et al. | |
| 6,635,055 B1 | 10/2003 | Cronin | |
| 6,645,234 B2 | 11/2003 | Evans et al. | |
| 6,652,515 B1 | 11/2003 | Maguire et al. | |
| 6,676,657 B2 | 1/2004 | Wood | |
| D487,039 S | 2/2004 | Webster et al. | |
| 6,706,040 B2 | 3/2004 | Mahon et al. | |
| 6,723,091 B2 | 4/2004 | Goble et al. | |
| 6,740,108 B1 | 5/2004 | Just et al. | |
| 6,770,070 B1 | 8/2004 | Balbierz | |
| 6,780,183 B2 | 8/2004 | Jimenez, Jr. et al. | |
| D496,997 S | 10/2004 | Dycus et al. | |
| D499,181 S | 11/2004 | Dycus et al. | |
| 6,869,431 B2 | 3/2005 | Maguire et al. | |
| 6,893,436 B2 | 5/2005 | Woodard et al. | |
| 6,932,776 B2 | 8/2005 | Carr | |
| 6,997,925 B2 | 2/2006 | Maguire et al. | |
| 7,004,938 B2 | 2/2006 | Ormsby et al. | |
| 7,047,068 B2 | 5/2006 | Haissaguerre | |
| D525,361 S | 7/2006 | Hushka | |
| 7,089,063 B2 | 8/2006 | Lesh et al. | |
| 7,113,832 B2 | 9/2006 | Longo | |
| D531,311 S | 10/2006 | Guerra et al. | |
| D533,942 S | 12/2006 | Kerr et al. | |
| D535,027 S | 1/2007 | James et al. | |
| 7,197,356 B2 | 3/2007 | Carr | |
| D541,418 S | 4/2007 | Schechter et al. | |
| 7,200,445 B1 | 4/2007 | Dalbec et al. | |
| D541,938 S | 5/2007 | Kerr et al | |
| 7,233,820 B2 | 6/2007 | Gilboa | |
| 7,261,001 B2 | 8/2007 | Heijnsdijk et al. | |
| 7,263,398 B2 | 8/2007 | Carr | |
| 7,285,116 B2 | 10/2007 | de la Rama et al. | |
| 7,294,125 B2 | 11/2007 | Phalen et al. | |
| 7,300,436 B2 | 11/2007 | Penny et al. | |
| 7,303,558 B2 | 12/2007 | Swanson | |
| D564,662 S | 3/2008 | Moses et al. | |
| 7,402,168 B2 | 7/2008 | Sanderson et al. | |
| 7,410,486 B2 | 8/2008 | Fuimaono et al. | |
| D576,932 S | 9/2008 | Strehler | |
| 7,467,015 B2 | 12/2008 | van der Weide | |
| 7,507,229 B2 | 3/2009 | Hewitt et al. | |
| D594,736 S | 6/2009 | Esjunin | |
| D594,737 S | 6/2009 | Kelly et al. | |
| 7,559,916 B2 | 7/2009 | Smith et al. | |
| 7,608,056 B2 | 10/2009 | Kennedy, II | |
| 7,611,508 B2 | 11/2009 | Yang et al. | |
| D606,203 S | 12/2009 | Husheer et al. | |
| D613,412 S | 4/2010 | DeCarlo | |
| 7,713,259 B2 | 5/2010 | Gosiengfiao et al. | |
| 7,734,330 B2 | 6/2010 | Carr | |
| 7,769,469 B2 | 8/2010 | Carr et al. | |
| 7,850,685 B2 | 12/2010 | Kunis et al. | |
| D634,010 S | 3/2011 | DeCarlo | |
| 7,921,855 B2 | 4/2011 | Danek et al. | |
| 7,933,660 B2 | 4/2011 | Carr | |
| 7,993,351 B2 | 8/2011 | Worley et al. | |
| 8,152,795 B2 | 4/2012 | Farr et al. | |
| 8,182,466 B2 | 5/2012 | Stehr et al. | |
| 8,226,566 B2 | 7/2012 | Nita | |
| 8,251,987 B2 | 8/2012 | Willyard | |
| 8,289,551 B2 | 10/2012 | Wu | |
| 8,292,881 B2 | 10/2012 | Brannan et al. | |
| 8,340,740 B2 | 12/2012 | Holzer et al. | |
| D681,810 S | 5/2013 | Decarlo | |
| 8,476,242 B2 | 7/2013 | Mon | |
| 8,632,461 B2 | 1/2014 | Glossop | |
| 8,768,485 B2 | 7/2014 | Hancock et al. | |
| 8,951,225 B2 | 2/2015 | Evard et al. | |
| 2002/0022836 A1 | 2/2002 | Goble et al. | |
| 2002/0042564 A1 | 4/2002 | Cooper et al. | |
| 2003/0191451 A1 | 10/2003 | Gilmartin | |

(56) References Cited

U.S. PATENT DOCUMENTS

| | | | |
|---|---|---|---|
| 2004/0082860 A1 | 4/2004 | Haissaguerre | |
| 2004/0097805 A1 | 5/2004 | Verard et al. | |
| 2004/0133254 A1 | 7/2004 | Sterzer et al. | |
| 2004/0176740 A1 | 9/2004 | Chouinard | |
| 2005/0043713 A1 | 2/2005 | Zhou | |
| 2005/0080334 A1 | 4/2005 | Willis | |
| 2005/0215942 A1 | 9/2005 | Abrahamson et al. | |
| 2005/0273006 A1 | 12/2005 | Stewart et al. | |
| 2006/0009833 A1 | 1/2006 | Chobotov et al. | |
| 2006/0089637 A1 | 4/2006 | Werneth et al. | |
| 2006/0167416 A1* | 7/2006 | Mathis et al. | 604/164.01 |
| 2006/0241564 A1 | 10/2006 | Corcoran et al. | |
| 2006/0253102 A1 | 11/2006 | Nance et al. | |
| 2007/0027385 A1 | 2/2007 | Brister et al. | |
| 2007/0060944 A1 | 3/2007 | Boldenow et al. | |
| 2007/0088319 A1 | 4/2007 | Martone | |
| 2007/0129717 A1 | 6/2007 | Brown et al. | |
| 2007/0185554 A1 | 8/2007 | Appling et al. | |
| 2007/0282319 A1 | 12/2007 | van der Weide et al. | |
| 2007/0287912 A1 | 12/2007 | Khuri-Yakub et al. | |
| 2008/0091169 A1 | 4/2008 | Heideman et al. | |
| 2008/0147056 A1 | 6/2008 | van der Weide et al. | |
| 2008/0208031 A1 | 8/2008 | Kurpad et al. | |
| 2008/0208039 A1 | 8/2008 | Kurpad et al. | |
| 2008/0228167 A1 | 9/2008 | Mittermeyer et al. | |
| 2008/0255507 A1 | 10/2008 | Mushtaha | |
| 2008/0262342 A1 | 10/2008 | Averbruch | |
| 2008/0262472 A1 | 10/2008 | Lunn et al. | |
| 2009/0076409 A1 | 3/2009 | Wu et al. | |
| 2009/0187180 A1 | 7/2009 | Brannan | |
| 2009/0222002 A1 | 9/2009 | Bonn et al. | |
| 2009/0234220 A1 | 9/2009 | Maschke | |
| 2009/0312754 A1 | 12/2009 | Lenihan et al. | |
| 2010/0004631 A1 | 1/2010 | Zhou | |
| 2010/0036369 A1 | 2/2010 | Hancock | |
| 2010/0076424 A1 | 3/2010 | Carr | |
| 2010/0121319 A1* | 5/2010 | Chu et al. | 606/33 |
| 2010/0160719 A1 | 6/2010 | Kassab et al. | |
| 2010/0249754 A1 | 9/2010 | Griffin et al. | |
| 2010/0256621 A1 | 10/2010 | Babkin et al. | |
| 2010/0262134 A1 | 10/2010 | Jensen et al. | |
| 2010/0268196 A1 | 10/2010 | Hastings et al. | |
| 2011/0004205 A1 | 1/2011 | Chu et al. | |
| 2011/0034913 A1 | 2/2011 | Brannan | |
| 2011/0034917 A1 | 2/2011 | Brannan | |
| 2011/0040300 A1 | 2/2011 | Brannan | |
| 2011/0046622 A1* | 2/2011 | McAuley | 606/41 |
| 2011/0077634 A1 | 3/2011 | Brannan | |
| 2011/0085720 A1 | 4/2011 | Averbuch | |
| 2011/0118721 A1 | 5/2011 | Brannan | |
| 2011/0130750 A1 | 6/2011 | Ormsby et al. | |
| 2011/0166518 A1 | 7/2011 | Nguyen et al. | |
| 2011/0166519 A1 | 7/2011 | Nguyen et al. | |
| 2011/0282336 A1 | 11/2011 | Brannan et al. | |
| 2011/0301587 A1 | 12/2011 | Deem et al. | |
| 2012/0065481 A1 | 3/2012 | Hunter et al. | |
| 2012/0071822 A1 | 3/2012 | Romo et al. | |
| 2012/0078175 A1 | 3/2012 | Vreeman | |
| 2012/0078230 A1 | 3/2012 | Lowe et al. | |
| 2012/0277730 A1 | 11/2012 | Salahieh et al. | |
| 2013/0090552 A1* | 4/2013 | Ramamurthy et al. | 600/424 |
| 2013/0137977 A1 | 5/2013 | Eder | |
| 2013/0197481 A1 | 8/2013 | Guo et al. | |
| 2013/0197482 A1 | 8/2013 | Akitomo | |
| 2014/0024909 A1* | 1/2014 | Vij et al. | 600/373 |
| 2014/0066922 A1* | 3/2014 | Coe et al. | 606/33 |
| 2014/0094793 A1 | 4/2014 | Sharonov | |
| 2015/0141985 A1 | 5/2015 | Mayse et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1034747 A1 | 9/2000 |
| EP | 1034748 | 9/2000 |
| EP | 1055400 | 11/2000 |
| EP | 1 159 926 A2 | 12/2001 |
| EP | 2147651 A1 | 1/2010 |
| EP | 2322113 A1 | 5/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |

(56) References Cited

FOREIGN PATENT DOCUMENTS

| | | |
|---|---|---|
| JP | 2001128990 A | 5/2001 |
| JP | 2001231870 A | 8/2001 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 94/16632 A1 | 8/1994 |
| WO | 97/24074 A1 | 7/1997 |
| WO | 00/10456 A1 | 3/2000 |
| WO | 00/36985 A2 | 6/2000 |
| WO | 0057811 A1 | 10/2000 |
| WO | 0100114 A1 | 1/2001 |
| WO | 01/67035 A1 | 9/2001 |
| WO | 02/45790 A2 | 6/2002 |
| WO | 2006084676 A1 | 8/2006 |
| WO | 2008/068485 A2 | 6/2008 |
| WO | 2010/035831 A1 | 4/2010 |
| WO | 2011139589 A2 | 11/2011 |

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Joseph D. Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
LigaSureTM Vessel Sealing System, the Seal of Confidence in General , Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.

(56) References Cited

OTHER PUBLICATIONS

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. Ml, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.

(56) References Cited

OTHER PUBLICATIONS

Humphries Jr. et al., "Finite-Element Codes to Model Electrical Heating and Non-LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSureTM Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSureTM Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSureTM Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, " LigaSureTM System Used in Laparoscopic 1st and 2nd Stage Orchiopexy" Innovations That Work, Nov. 2002.

Kennedy et al., "High-burst-strength, feedback-controlled bipolar vessel sealing" Surgical Endoscopy (1998) 12:876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

International Search Report corresponding to PCT/US2013/052166, completed Nov. 15, 2013 and mailed Nov. 18, 2013; (12 pp).

International Search Report corresponding to PCT/2013/052182, completed Nov. 6, 2013 and mailed Nov. 6, 2013; (14pp).

International Search Report corresponding to PCT/US2013/052187, completed Nov. 4, 2013 and mailed Nov. 4, 2013; (19 pp).

International Search Report corresponding to PCT/US2013/052196, completed Nov. 11, 2013 and mailed Nov. 11, 2013; (21 pp).

Search Report dated Nov. 4, 2015 received with Office Action dated Nov. 16, 2015 issued in Chinese Patent Application No. 201380041763.4 by the Chinese Patent Office and English translation (4 pages).

\* cited by examiner

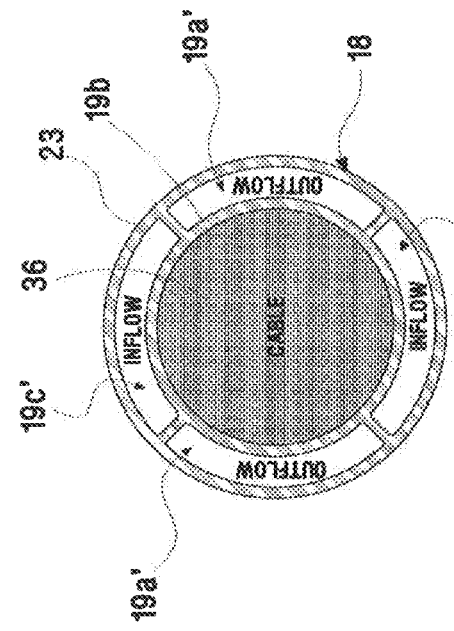
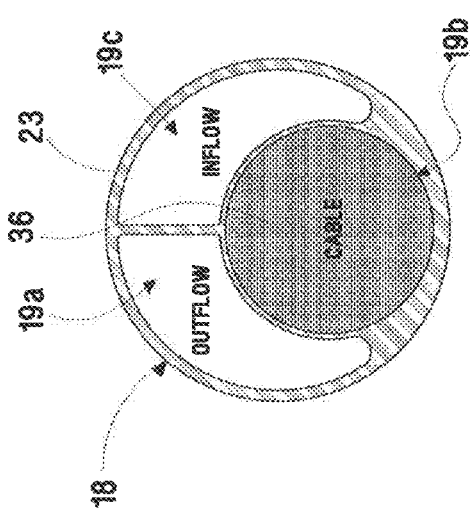
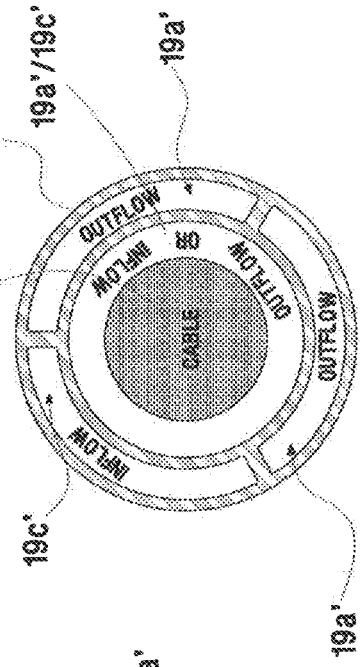
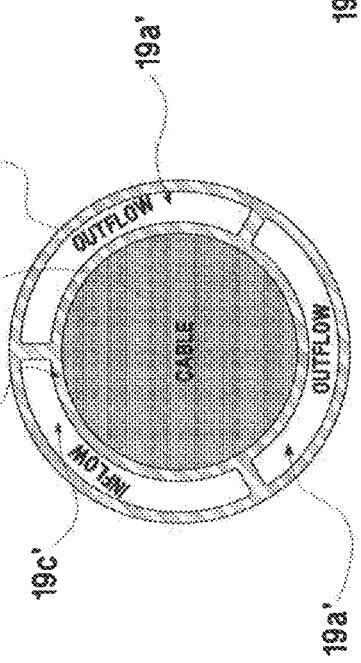
Fig.2
Fig.3A
Fig.3B
Fig.3C

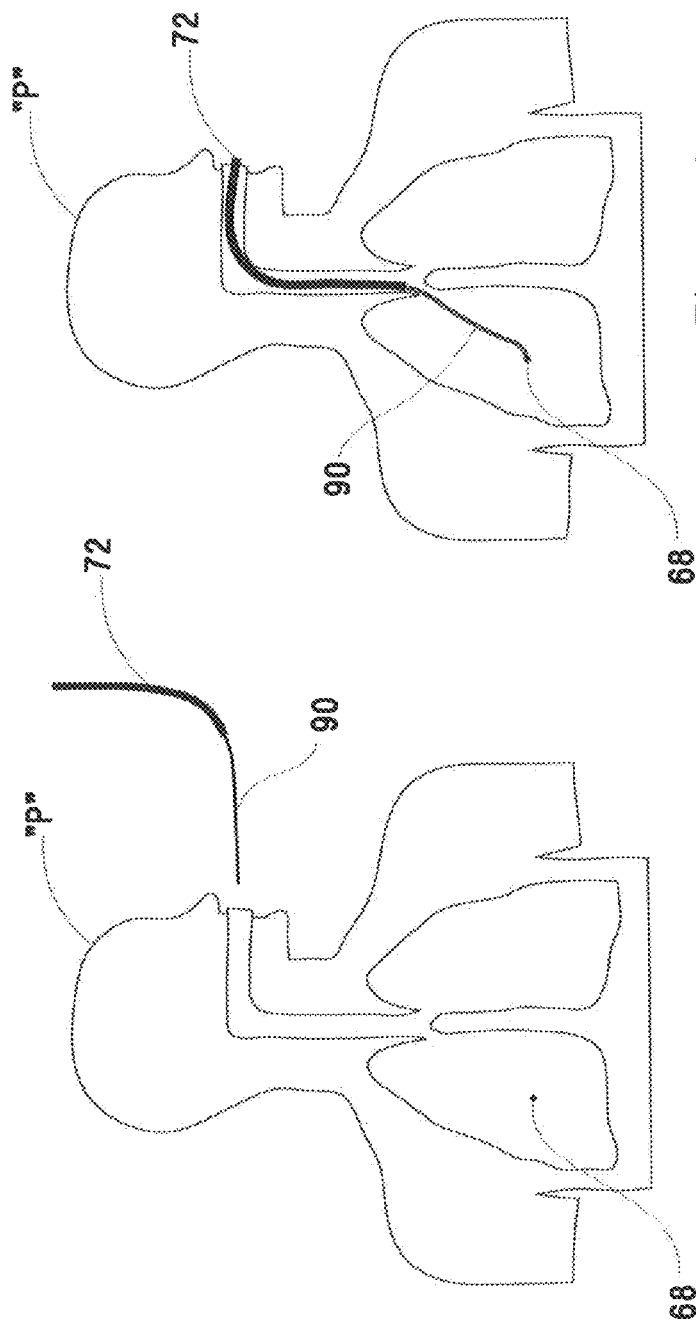
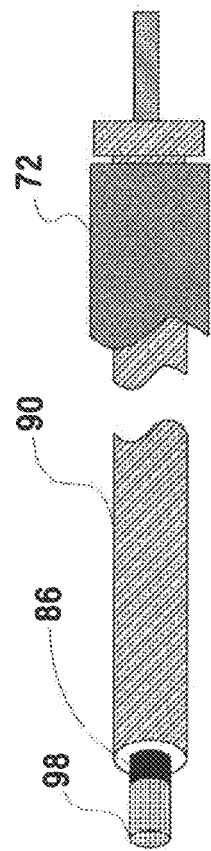
Fig. 12A  Fig. 12B  Fig. 12C

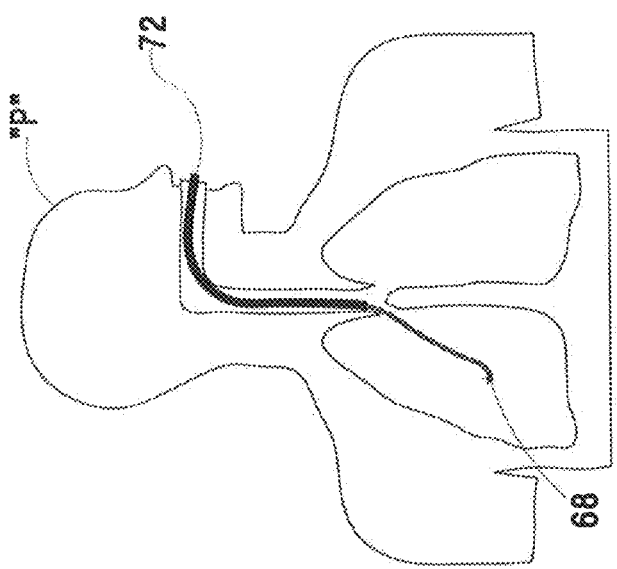
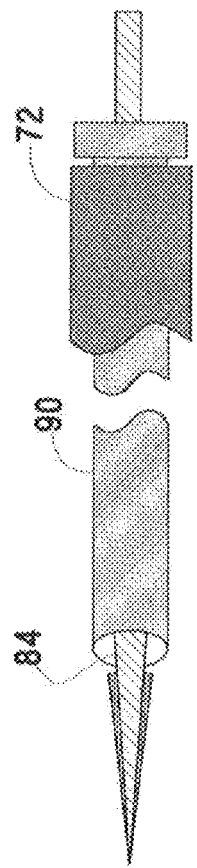
Fig. 13A
Fig. 13B

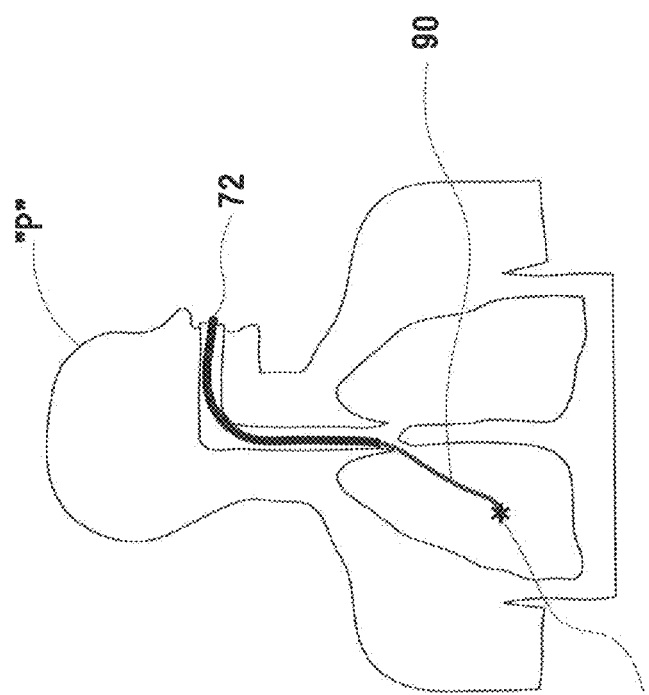
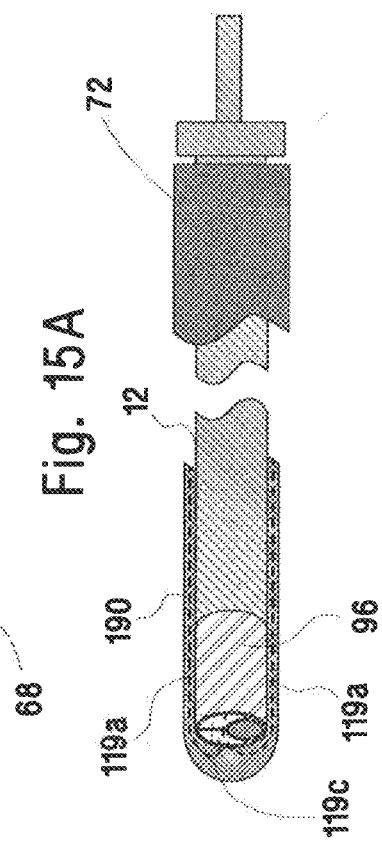

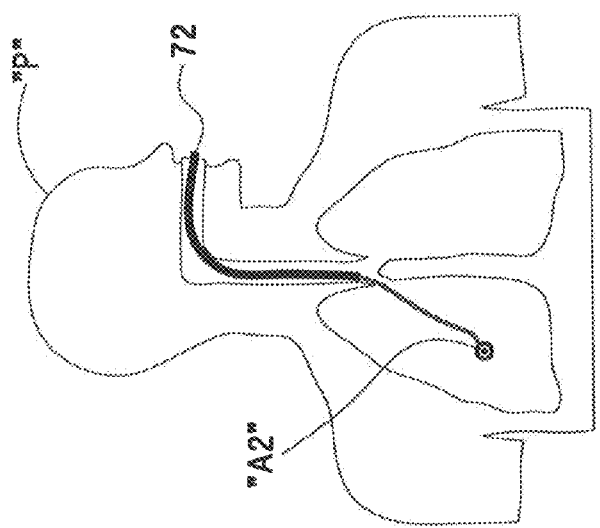
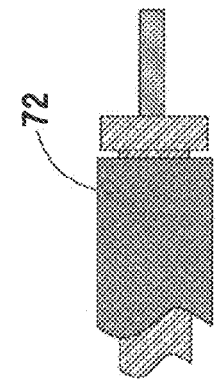
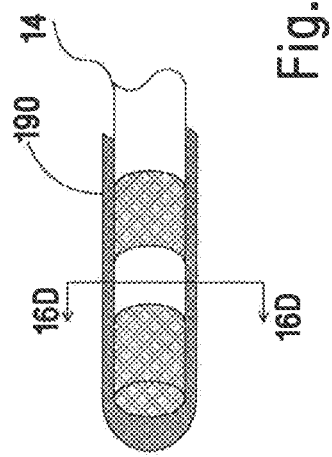
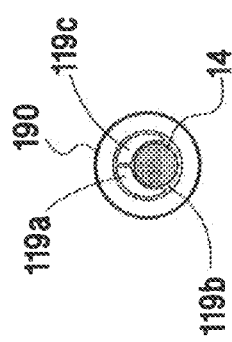
Fig. 16A
Fig. 16B
Fig. 16C
Fig. 16D

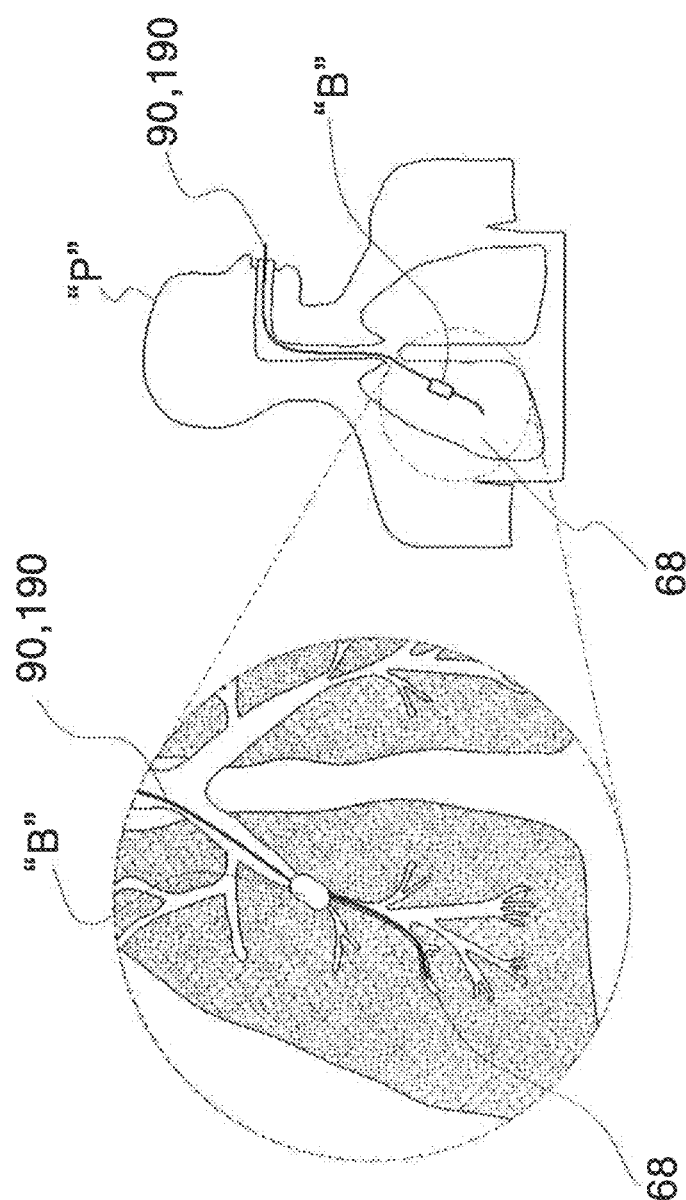

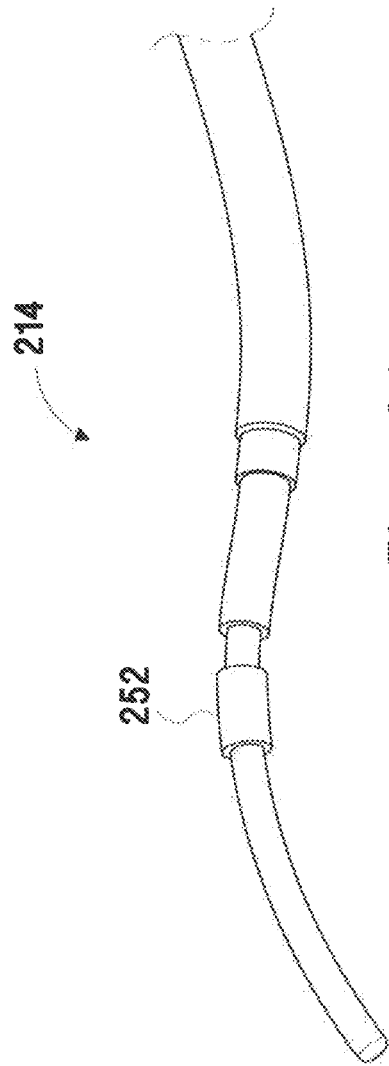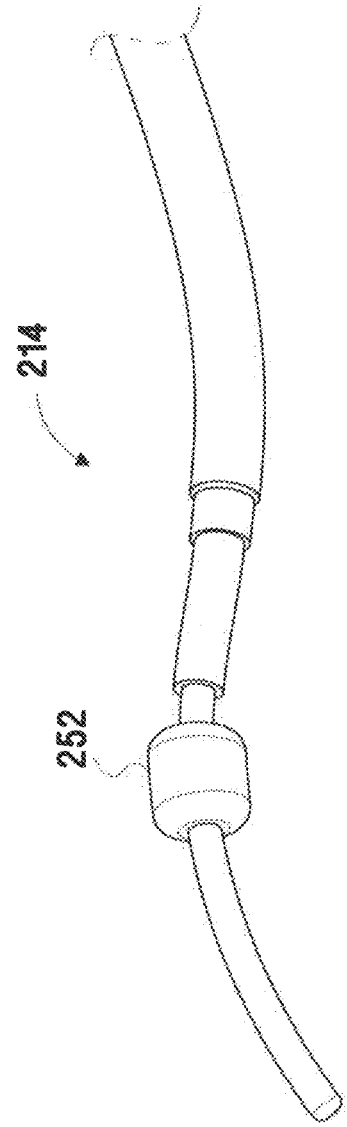

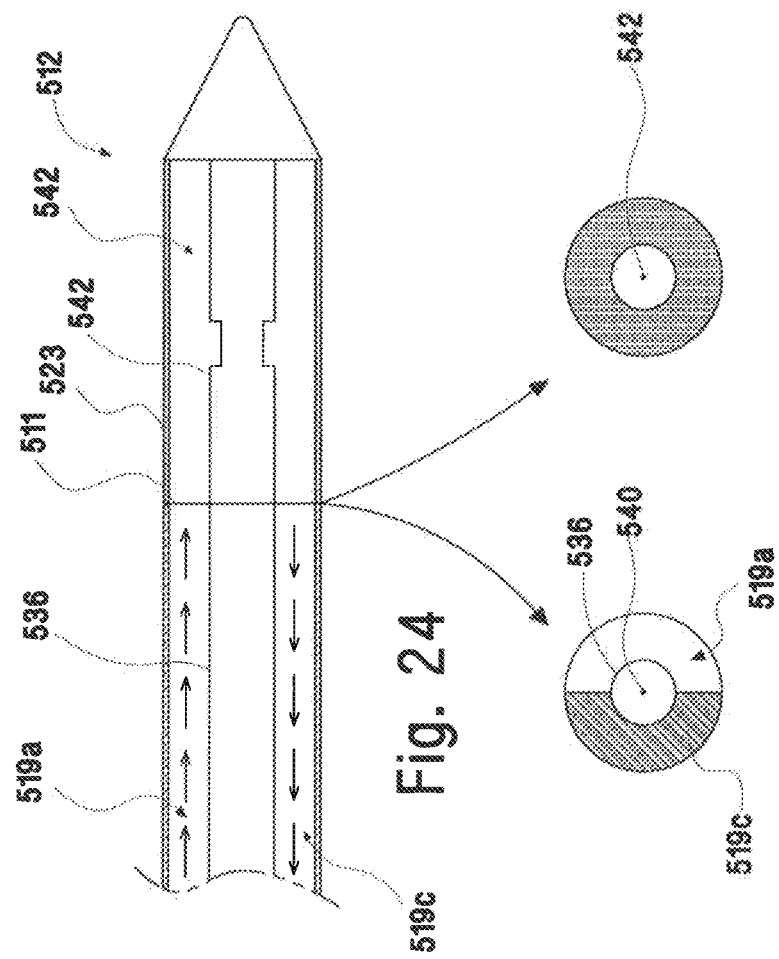

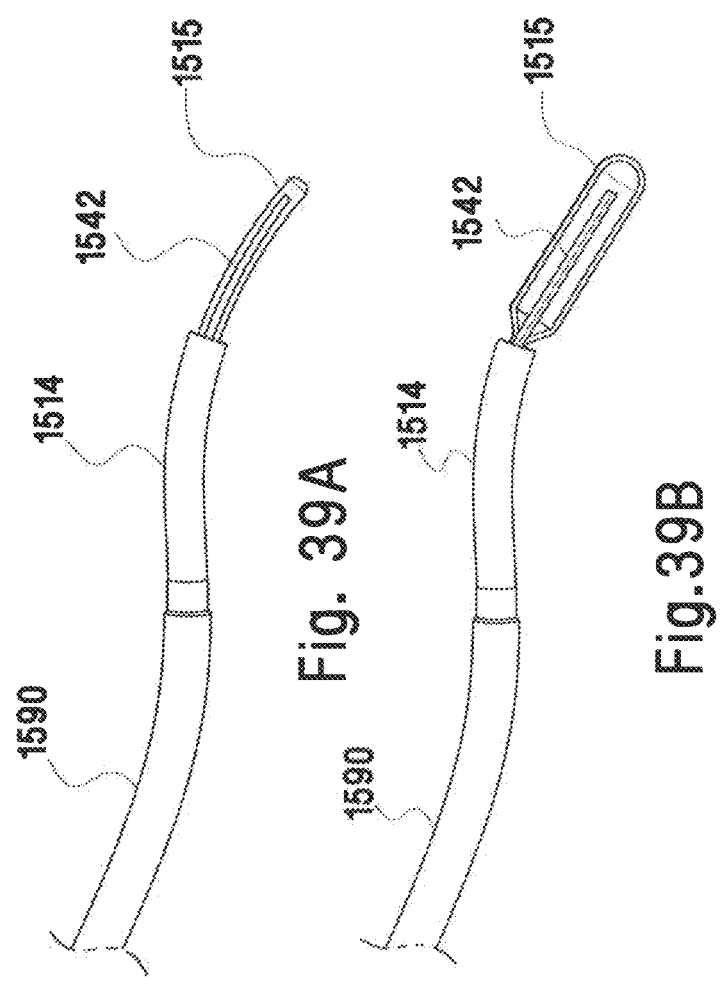

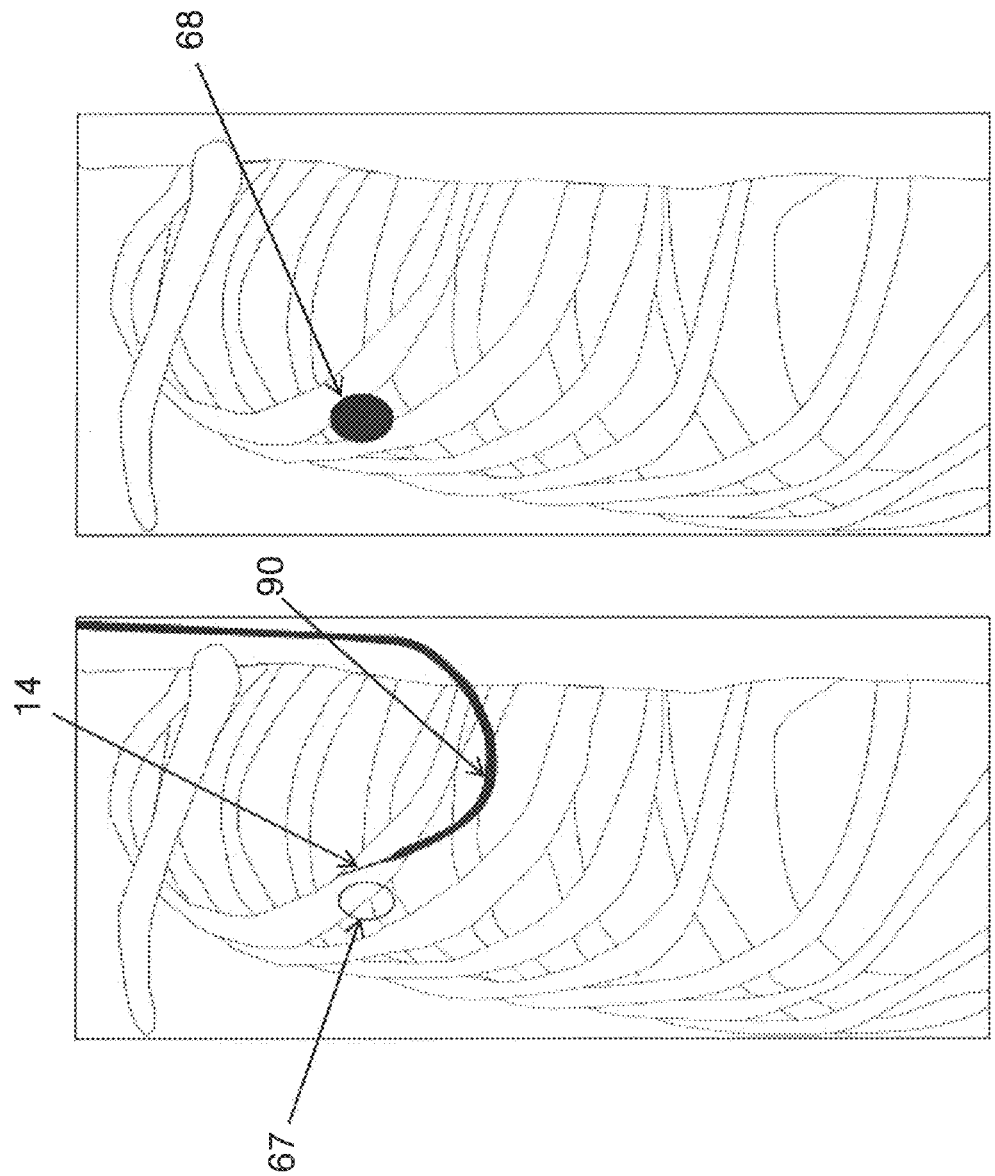

MICROWAVE ABLATION CATHETER AND METHOD OF UTILIZING THE SAME

CROSS REFERENCE TO RELATED APPLICATIONS

The present application claims the benefit of and priority to U.S. Provisional Patent Application Ser. No. 61/680,555 filed on Aug. 7, 2012 by Brannan et al.; U.S. Provisional Patent Application Ser. No. 61/783,921 filed on Mar. 14, 2013 by Ladtkow et al.; U.S. Provisional Patent Application Ser. No. 61/784,048 filed on Mar. 14, 2013 by Ladtkow et al.; U.S. Provisional Patent Application Ser. No. 61/784,176 filed on Mar. 14, 2013 by Ladtkow et al.; U.S. Provisional Patent Application Ser. No. 61/784,297 filed on Mar. 14, 2013 by Ladtkow et al.; and U.S. Provisional Patent Application Ser. No. 61/784,407 filed on Mar. 14, 2013 by Ladtkow et al., the entire contents of each being incorporated herein by reference.

BACKGROUND

1. Technical Field

The present disclosure relates to a microwave ablation catheter and method of utilizing the same. More particularly, the present disclosure relates to a microwave ablation catheter that is positionable through one or more branched luminal networks of a patient for treating tissue.

2. Description of Related Art

Microwave ablation may be utilized for treating various maladies, e.g., nodules, of different organs like the liver, brain, heart, lung and kidney. When a nodule is found, for example, within a lung, several factors are considered in making a diagnosis. For example, a biopsy of the nodule may be taken using a biopsy tool under CT guidance. If the biopsy reveals that the nodule is malignant, it may prove useful to ablate the nodule. In this instance, microwave ablation, which typically includes transmitting microwave energy to a percutaneous needle, may be utilized to ablate the nodule. Under certain surgical scenarios, certain current percutaneous methods of microwave ablation procedures can result in pneumothoraces (air leaks) and a collection of air in the space around the lungs which if not appreciated by the clinician can ultimately lead to collapse of the lung or a portion thereof Endobronchial navigation uses CT image data to create a navigation plan to facilitate advancing a navigation catheter (or other suitable device) through a bronchoscope and a branch of the bronchus of a patient to the nodule. Electromagnetic tracking may also may be utilized in conjunction with the CT data to facilitate guiding the navigation catheter through the branch of the bronchus to the nodule. In certain instances, the navigation catheter may be positioned within one of the airways of the branched luminal networks adjacent to or within the nodule or point of interest to provide access for one or more tools. Once the navigation catheter is in position, fluoroscopy may be used to visualize biopsy tools, such as, for example, biopsy brushes, needle brushes and biopsy forceps as they are passed through the navigation catheter and into the lung and to the nodule or point of interest.

SUMMARY

As can be appreciated, a microwave ablation catheter that is positionable through one or more branched luminal networks of a patient to treat tissue may prove useful in the surgical arena.

Aspects of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present discloser provides a microwave ablation system configured for use in luminal network. The microwave ablation system includes a microwave energy source and a tool for treating tissue. An extended working channel is configured to provide passage for the tool. A locatable guide catheter is positionable through the extended working channel and configured to navigate the extended working channel adjacent the target tissue. The microwave ablation system includes a navigation system that is configured for guiding the tool, extended working channel or the locatable guide through a luminal network following a predetermined determined pathway to the target tissue.

The microwave ablation system may include a bronchoscope that is configured to receive the extended working channel for providing access to the luminal network. The tool may be a microwave ablation catheter, a biopsy brush, needle brushes and biopsy forceps.

The microwave ablation catheter may include a coaxial cable that is connected at its proximal end to a microwave energy source and at its distal end to a distal radiating section. The coaxial cable includes inner and outer conductors and a dielectric positioned therebetween. The inner conductor extends distally past the outer conductor and is in sealed engagement with the distal radiating section. A balun is formed in part from a conductive material electrically connected to the outer conductor of the coaxial cable and extends along at least a portion of the coaxial cable. The conductive material has a braided configuration and is covered by at least one insulative material.

A multi-lumen housing that is configured to receive the ablation catheter may be provided with the microwave ablation system. The multi-lumen housing may include a hub at a proximal end thereof. The hub may include a plurality of ports. One of the plurality of ports may be an electrical port configured to provide electrical communication between the coaxial cable and the microwave energy source. Two of the plurality of ports may be a fluid intake port and a fluid return port configured to provide respective ingress and egress of a coolant to and from the multi-lumen housing for cooling the distal radiating section of the coaxial cable.

The multi-lumen housing may include a four lumen configuration having two lumens dedicated for communication with a respective one of the fluid intake and return ports and two lumens dedicated to support the coaxial cable including the balun. Alternatively, the multi-lumen housing may include a five lumen configuration having four lumens two of which being dedicated for communication with the fluid intake port and two of which being dedicated for communication with the fluid return port and one lumen designated to support the coaxial cable including the balun.

The extended working channel may include a closed distal end. The extended working channel may include a multi-lumen configuration and may be configured to receive the ablation catheter. The extended working channel may include hub at a proximal end thereof. The hub may include a plurality of ports. Two of the plurality of ports may be a fluid intake port and a fluid return port configured to provide respective ingress and egress of a coolant to and from the extended working channel for cooling the distal radiating section of the coaxial cable.

The extended working channel may include a three lumen configuration having two lumens dedicated for communication with a respective one of the fluid intake and return ports and one lumen dedicated to support the coaxial cable including the balun. Alternatively, the extended working channel may include a four lumen configuration having two lumens dedicated for communication with a respective one of the fluid intake and return ports and two lumens dedicated to support the coaxial cable including the balun. Alternatively, the extended working channel may include a five lumen configuration having four lumens two of which being dedicated for communication with the fluid intake port and two of which being dedicated for communication with the fluid return port and one lumen designated to receive the ablation catheter.

The predetermined pathway may be generated based on computed tomographic (CT) data of the luminal network, and is displayed in a generated model. The predetermined pathway may be generated from CT data to identify a pathway to a target identified by a user in the CT data, and the pathway is generated for acceptance by the user before use in the navigation system.

An aspect of the present disclosure provides a microwave ablation system configured for use in luminal network. The microwave ablation system includes a microwave energy source and a tool for treating tissue. An extended working channel is configured to provide passage for the tool. A locatable guide catheter is positionable through the extended working channel and configured to navigate the extended working channel adjacent the target tissue. The microwave ablation system includes one or more imaging modalities for confirming placement of the tool within target tissue.

The microwave ablation system may include a bronchoscope that is configured to receive the extended working channel for providing access to the luminal network. The tool may be a microwave ablation catheter, a biopsy brush, needle brushes and biopsy forceps.

The microwave ablation catheter may include a coaxial cable that is connected at its proximal end to a microwave energy source and at its distal end to a distal radiating section. The coaxial cable includes inner and outer conductors and a dielectric positioned therebetween.

The inner conductor extends distally past the outer conductor and is in sealed engagement with the distal radiating section. A balun is formed in part from a conductive material electrically connected to the outer conductor of the coaxial cable and extends along at least a portion of the coaxial cable. The conductive material has a braided configuration and is covered by at least one insulative material.

A multi-lumen housing that is configured to receive the ablation catheter may be provided with the microwave ablation system. The multi-lumen housing may include a hub at a proximal end thereof. The hub may include a plurality of ports. One of the plurality of ports may be an electrical port configured to provide electrical communication between the coaxial cable and the microwave energy source. Two of the plurality of ports may be a fluid intake port and a fluid return port configured to provide respective ingress and egress of a coolant to and from the multi-lumen housing for cooling the distal radiating section of the coaxial cable.

The multi-lumen housing may include a four lumen configuration having two lumens dedicated for communication with a respective one of the fluid intake and return ports and two lumens dedicated to support the coaxial cable including the balun. Alternatively, the multi-lumen housing may include a five lumen configuration having four lumens two of which being dedicated for communication with the fluid intake port and two of which being dedicated for communication with the fluid return port and one lumen designated to support the coaxial cable including the balun.

The extended working channel may include a closed distal end. The extended working channel may include a multi-lumen configuration and may be configured to receive the ablation catheter. The extended working channel may include hub at a proximal end thereof. The hub may include a plurality of ports. Two of the plurality of ports may be a fluid intake port and a fluid return port configured to provide respective ingress and egress of a coolant to and from the extended working channel for cooling the distal radiating section of the coaxial cable.

The extended working channel may include a three lumen configuration having two lumens dedicated for communication with a respective one of the fluid intake and return ports and one lumen dedicated to support the coaxial cable including the balun. Alternatively, the extended working channel may include a four lumen configuration having two lumens dedicated for communication with a respective one of the fluid intake and return ports and two lumens dedicated to support the coaxial cable including the balun. Alternatively, the extended working channel may include a five lumen configuration having four lumens two of which being dedicated for communication with the fluid intake port and two of which being dedicated for communication with the fluid return port and one lumen designated to receive the ablation catheter.

The imaging modality may be computer tomography, ultrasound and fluoroscopy. Computer tomography data may be manipulated to create a virtual fluoroscopic image that identifies the target tissue. The virtual fluoroscopic image is generated for comparison with a live fluoroscopic image to provide a user with the ability to compare placement of the extended working channel and microwave ablation catheter within target tissue.

BRIEF DESCRIPTION OF THE DRAWING

Various embodiments of the present disclosure are described hereinbelow with references to the drawings, wherein:

FIG. 2 is a front view of an embodiment of a lumen configuration configured for use with the microwave catheter assembly shown in FIG. 1;

FIG. 3A is a front view of an another embodiment of a lumen configuration configured for use with the microwave catheter assembly shown in FIG. 1;

FIG. 3B is a front view of an another embodiment of a lumen configuration configured for use with the microwave catheter assembly shown in FIG. 1;

FIG. 3C is a front view of an another embodiment of a lumen configuration configured for use with the microwave catheter assembly shown in FIG. 1, whereby the lumen supporting the coaxial microwave structure also communicates cooling fluid with inflow or outflow ports;

FIG. 12A is a schematic, plan view of the extended working channel positioned within a bronchoscope prior to being positioned within a trachea of a patient;

FIG. 12B is a schematic, plan view of the bronchoscope shown in FIG. 12A positioned within the trachea of the patient with the extended working channel extending distally therefrom;

FIG. 12C is a partial, cutaway view of the extended working channel and locatable guide positioned within the bronchoscope;

FIG. 13A is a schematic, plan view of the bronchoscope positioned within the trachea of the patient with the extended working channel extending distally therefrom;

FIG. 13B is a partial, cutaway view of the extended working channel and a biopsy tool positioned within the bronchoscope;

FIG. 15A is a schematic, plan view of the bronchoscope positioned within the trachea of the patient with an extended working channel according to an alternate embodiment extending distally therefrom;

FIG. 15B is a partial, cutaway view of the extended working channel shown in FIG. 15A positioned within the bronchoscope;

FIG. 16A is a schematic, plan view of the bronchoscope positioned within the trachea of the patient with the extended working channel shown in FIG. 15A extending distally therefrom;

FIG. 16B is a schematic, plan view of the bronchoscope positioned within the trachea of the patient with the extended working channel shown in FIG. 15A extending distally therefrom and adjacent target tissue;

FIG. 16C is a partial, cutaway view of the extended working channel and the microwave ablation catheter shown in FIG. 2 coupled to one another and positioned within the bronchoscope;

FIG. 16D is a cross-sectional view taken along line section 16D-16D in FIG. 16C;

FIG. 17 is a schematic, plan view of another embodiment of the extended working shown in FIGS. 9 and 15A with the extended working channel positioned within the lung of a patient and having a balloon coupled thereto in an deflated configuration;

FIG. 18 is an enlarged area of detail of Fig, 17 and showing the balloon in an inflated configuration;

FIG. 19A is a schematic, plan view of an alternate embodiment of a balun configured for use with the microwave ablation catheter shown in FIG. 2 with the balun shown in an expanded configuration;

FIG. 19B is a schematic, plan view of the balun shown in FIG. 19A in an non-expanded configuration;

FIG. 24 is a partial, cutaway view of another embodiment of the microwave ablation catheter shown in FIG. 1;

FIG. 25 is a cross-sectional view taken along line section 25-25 in FIG. 24;

FIG. 26 is a cross-sectional view taken along line section 26-26 in FIG. 24;

FIG. 39A is a schematic, plan view of an alternate embodiment of the microwave ablation catheter shown in FIG. 2 including a balloon coupled thereto and shown in a deflated configuration;

FIG. 39B is a schematic, plan view of the microwave catheter shown in FIG. 39A with the balloon shown in an inflated configuration;

FIG. 46A is a fluoroscopic images of a patient, having a catheter placed therein; and FIG. 46B is a virtual fluoroscopic image of a patient depicting a target.

DETAILED DESCRIPTION

Figure 1:
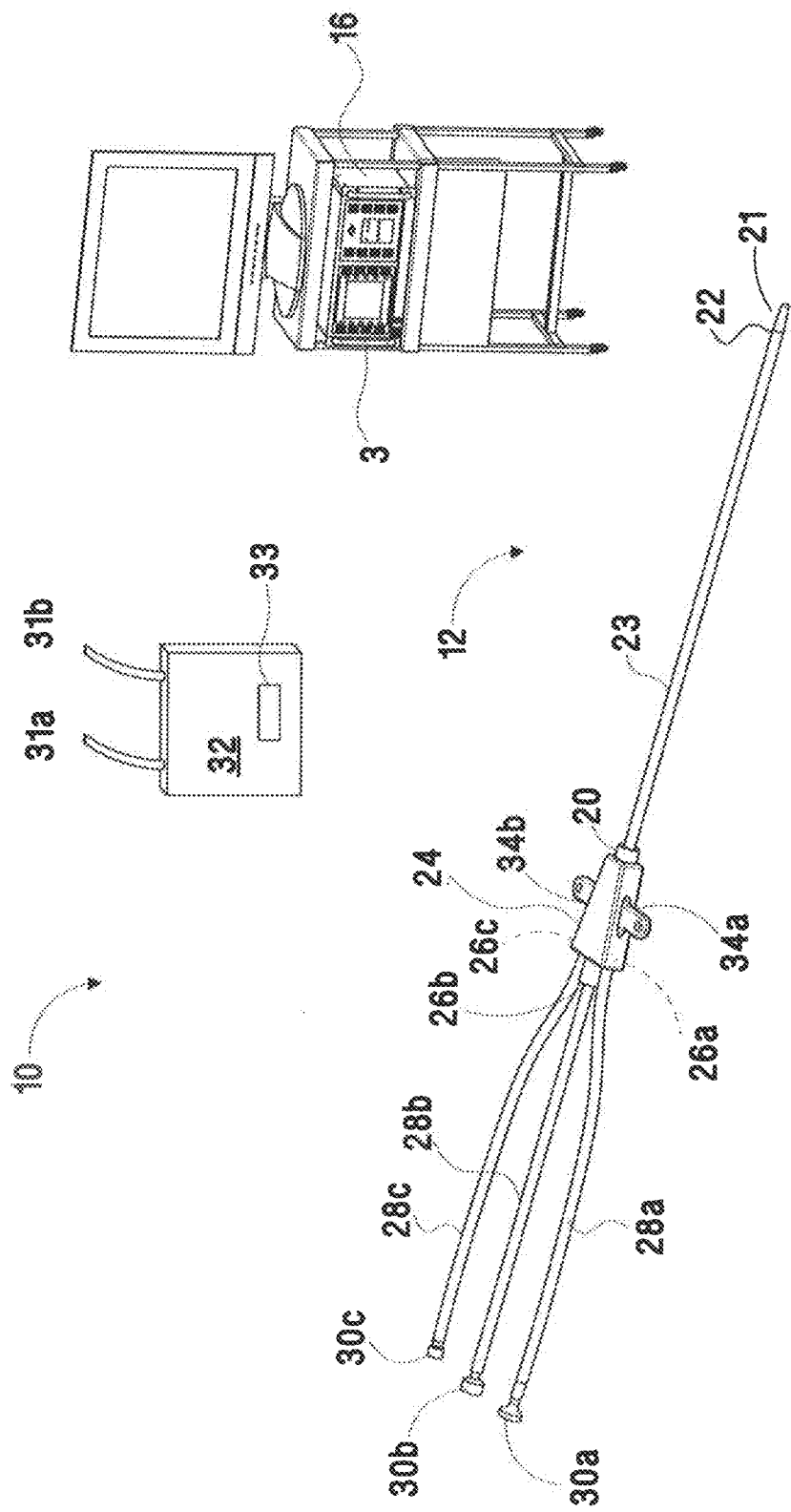
FIG. 1 is a perspective view of a microwave ablation system including a microwave ablation catheter assembly configured for use with a microwave ablation system according to an embodiment of the instant disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As can be appreciated an energy device, such as a microwave ablation catheter, that is positionable through one or more branched luminal networks of a patient to treat tissue may prove useful in the surgical arena and the present disclosure is directed to such apparatus, systems and methods. Access to lumeninal networks may be percutaneous or through natural orifice. In the case of natural orifice, an endobronchial approach may be particularly useful in the treatment of lung disease. Targets, navigation, access and treatment may be planned pre-procedurally using a combination of imaging and/or planning software. In accordance with these aspects of the present disclosure the planning software may offer custom guidance using pre-procedure images). Navigation of the luminal network may be accomplished using image-guidance. These image-guidance systems may be separate or integrated with the energy device or a separate access tool and may include MRI, CT, fluoroscopy, ultrasound, electrical impedance tomography, optical, and device tracking systems. Methodologies for locating the separate or integrated to the energy device or a separate access tool include EM, IR, echolocation, optical, and others. Tracking systems may integrated to imaging device, where tracking is done in virtual space or fused with preoperative or live images. In some cases the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device placement may be performed with imaging and/or navigational guidance using the modalities listed above. The energy device has the ability to deliver an energy field for treatment (including but not limited to electromagnetic fields) and may have the ability to monitor treatment during energy application. The monitoring of the treatment may include thermometry, electrical impedance, radiometry, density measurement, optical absorption, hydration, ultrasound, and others. Additionally or alternatively treatment may be monitored from within the lumen or extracorporeally using an additional device or the image-guidance modalities described above. After treatment, the energy device and/or an additional device may have the ability to confirm adequate treatment was performed, employing at least the techniques described above with respect to treatment monitoring. Further, treatment confirmation may be from within the lumen or extracorporeal. The long term treatment performance may be performed with imaging which may be integrated into a follow-up software application.

One embodiment of the present disclosure is directed, in part, to a microwave ablation catheter that is positionable through one or more branched luminal networks of a patient to treat tissue. The microwave ablation catheter is part of an ablation system that includes a microwave energy source and a planning and navigation system for the placement of the catheter at a desired location within the luminal network. Further, the system includes imaging modalities that can be employed to confirm placement of the catheter and the effect of the application of energy. The microwave catheter itself may include the capability to aide in the confirmation of the placement within the tissue to be treated, or additional devices may be used in combination with the microwave catheter to confirm placement within the tissue to be treated. Still further, one or more thermocouples or temperature sensors on the microwave catheter detect the temperature of the microwave catheter or the tissue surrounding the catheter and enable monitoring of the microwave catheter temperature and the tissue temperature during and after treatment both for safety purposes and for dosage and treatment pattern monitoring purposes. The microwave catheter may also assist in the access to the target tissue, either intraluminal or outside the lumen. The microwave catheter may also assist in the monitoring of the treatment through various measurement techniques and may also be used for treatment confirmation, in addition to assistance from other monitoring and confirmation devices.

FIGS. 1-5 depict various aspects of a microwave ablation system 10 (system 10). The system 10, as show in FIG. 1 includes a microwave ablation catheter assembly 12 (assembly 12) configured to house a microwave ablation catheter 14 (ablation catheter 14) (shown in FIG. 4). Assembly 12 and ablation catheter 14 are configured to couple to a microwave energy source (energy source 16) that is configured to transmit microwave energy to the catheter 14 to treat target tissue, e.g., lung tissue.

The assembly 12 shown in FIG. 1 is configured to receive the ablation catheter 14 and to provide a pathway for a cooling medium to circulate within the assembly 12 and cool the ablation catheter 14 when the ablation catheter 14 is energized. With these purposes in mind, assembly 12 is formed by overmolding plastic to form a generally elongated housing 23 having an outer sheath 18 (FIG. 2) and a plurality of lumens 19a, 19b, and 19c extending from a proximal end 20 to a distal end 22 that includes a relatively pointed or appropriately rounded distal tip 21. A hub portion 24 is provided at the proximal end 20 and includes ports 26a, 26b, 26c that couple to corresponding distal ends (not explicitly shown) of connection tubes 28a, 28b, 28c. Connection tubes 28a, 28c include respective proximal ends 30a, 30c that are configured to releasably couple either directly or indirectly to a fluid source 32 including hoses 31a, 31b that provide one or more suitable cooling mediums (e.g., water, saline, air or combination thereof) to the ablation catheter 14. In embodiments, the fluid source 32 may be a component of a cooling system that is disclosed in U.S. patent application Ser. No. 13/835, 625, entitled "Recirculating Cooling System For Energy Delivery Device", filed on Mar. 15, 2013, by Larson et al., the entirety of which is incorporated herein by reference. A proximal end 30b of connection tube 28b is configured to couple either directly or indirectly to the energy source 16 to energize the ablation catheter 14. An optional pair of wings 34a, 34b may be provided at the proximal end 20 of the assembly 12. The wings 34a, 34b may extend laterally from respective right and left sides of the proximal end 20 and may be configured to rest on a patient or to be grasped by a clinician for manipulation of the assembly 12.

The ports 26a, 26c of the assembly 12 are in fluid communication with corresponding lumens 19a, 19c of the plurality of lumens 18 provided within the assembly 12 (FIG. 2) and are configured to provide one of the aforementioned cooling mediums to the assembly 12. In an embodiment, such as the embodiment illustrated in FIG. 2, port 26a is an outflow port and provides a point of egress for the cooling medium from outflow lumen 19a and port 26c is an inflow port and provides point of ingress for the cooling medium into the inflow lumen 19c.

FIG. 3A illustrates an alternate lumen configuration that may be utilized with the assembly 12. In this embodiment, two outflow lumens 19a' and one inflow lumen 19c' are provided and are in fluid communication with the respective ports 26a, 26c.

FIG. 3B illustrates an alternate lumen configuration that may be utilized with the assembly 12. In this embodiment, two outflow lumens 19a' and one inflow lumen 19c' are provided and are in fluid communication with the respective ports 26a, 26c. Additionally, the lumen supporting the coaxial microwave structure is also used for either fluid inflow or outflow.

FIG. 3C illustrates an alternate lumen configuration similar to FIGS. 3a and 3b that may be utilized with the assembly 12. In this embodiment, two outflow lumens 19a' and two inflow lumens 19c' are provided and are in fluid communication with the respective ports 26a, 26c.

A third lumen 19b is provided within the assembly 12 and is configured to support the ablation catheter 14 when the ablation catheter 14 is coupled to the assembly 12. In the embodiment illustrated in FIG. 2, the outflow and inflow lumens 19a, 19c are formed above the lumen 19b. In the embodiment illustrated in FIG. 3A, the lumen 19b is centered between the outflow lumens 19a and inflow lumens 19c to provide two opposing outflow lumens 19a and two opposing inflow lumens 19c around the lumen 19b. In the embodiments illustrated in FIGS. 3A and 3B, the lumen 19b is centered between the outflow lumens 19a and inflow lumen 19c to provide two opposing outflow lumens 19a and one opposing inflow lumen 19c around the lumen 19b. The lumen configurations illustrated in FIGS. 2 and 3A-3C provide the assembly 12 with the needed flexibility to move within the relatively thin conductive airways (and/or vessels) in the branch of the bronchus.

In an embodiment, the assembly 12 may include a 4 lumen configuration (not shown). In this embodiment, three (3) outer lumens (e.g., a combination of outflow and inflow lumens 19a, 19c, respectively) may be equally spaced around a center lumen (e.g., lumen 19b) that is configured to support the ablation catheter 14 when the ablation catheter 14 is coupled to the assembly 12. In one particular embodiment, the three (3) outer lumens may be configured to include two (2) inflow lumens 19c and one (1) outflow lumen 19a (or vice versa).

The outflow and inflow lumens 19a, 19c extend a predetermined distance within the assembly 12 and can function with various coolant feedback protocols (e.g., open or closed feedback protocols). In the embodiments illustrated in FIGS. 2 and 3A-3C, the inflow lumens 19c extend distally of the outflow lumens 19a to allow an adequate amount of cooling medium to circulate around the ablation catheter 14. It should be understood, regardless of the number of or configuration of lumens, space not filled within the lumen supporting the coaxial cable and radiating section may be used for additional fluid ingress or egress to improve fluid flow and directly cool through intimate fluid contact the coaxial microwave structures. In addition to supporting the ablation catheter, the lumen 19b may also support additional outflow or inflow of coolant, whereby lumen 19b may couple to connection tubes 28a, 28c and their respective proximal ends 30a, 30c.

Figure 4:
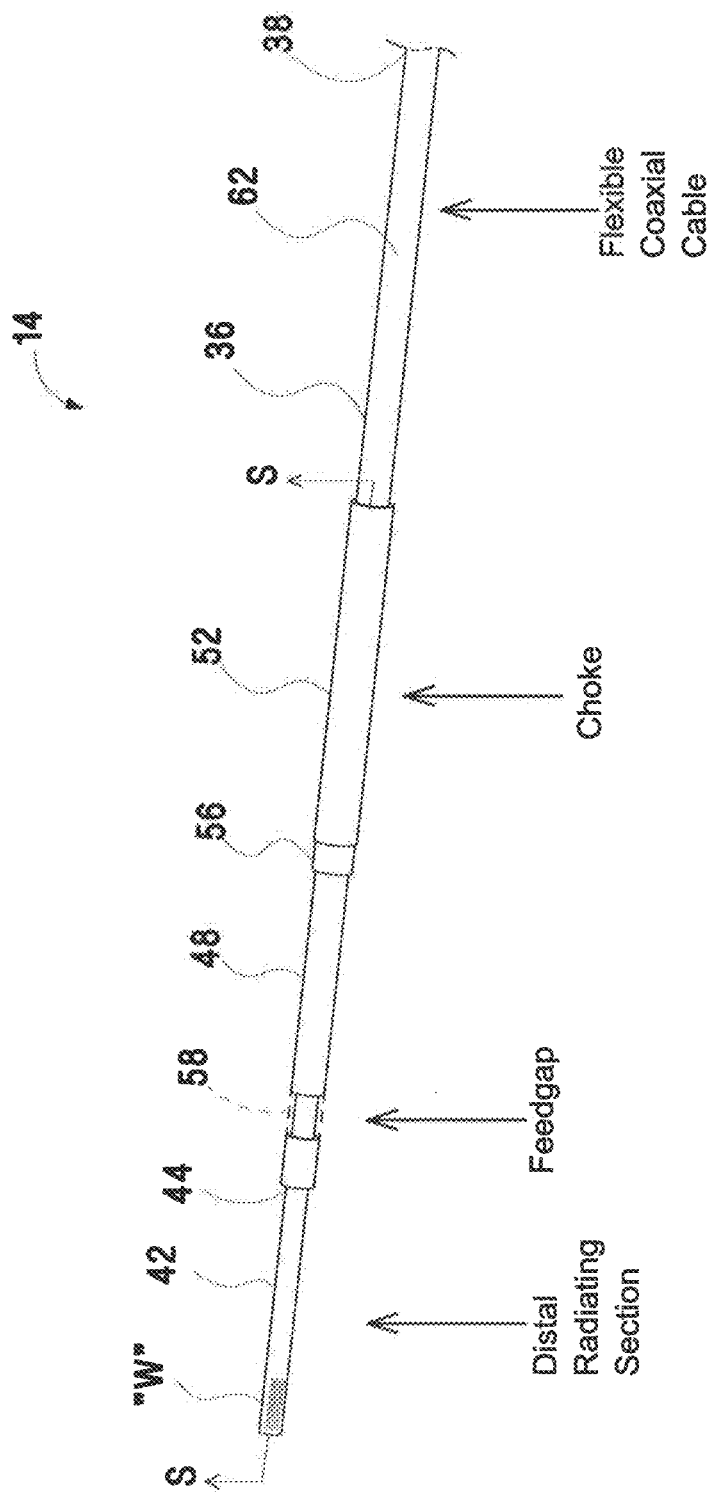
FIG. 4 is a perspective view of a distal end of a microwave ablation catheter configured for use with the microwave ablation assembly shown in FIG. 1.
Figure 5:
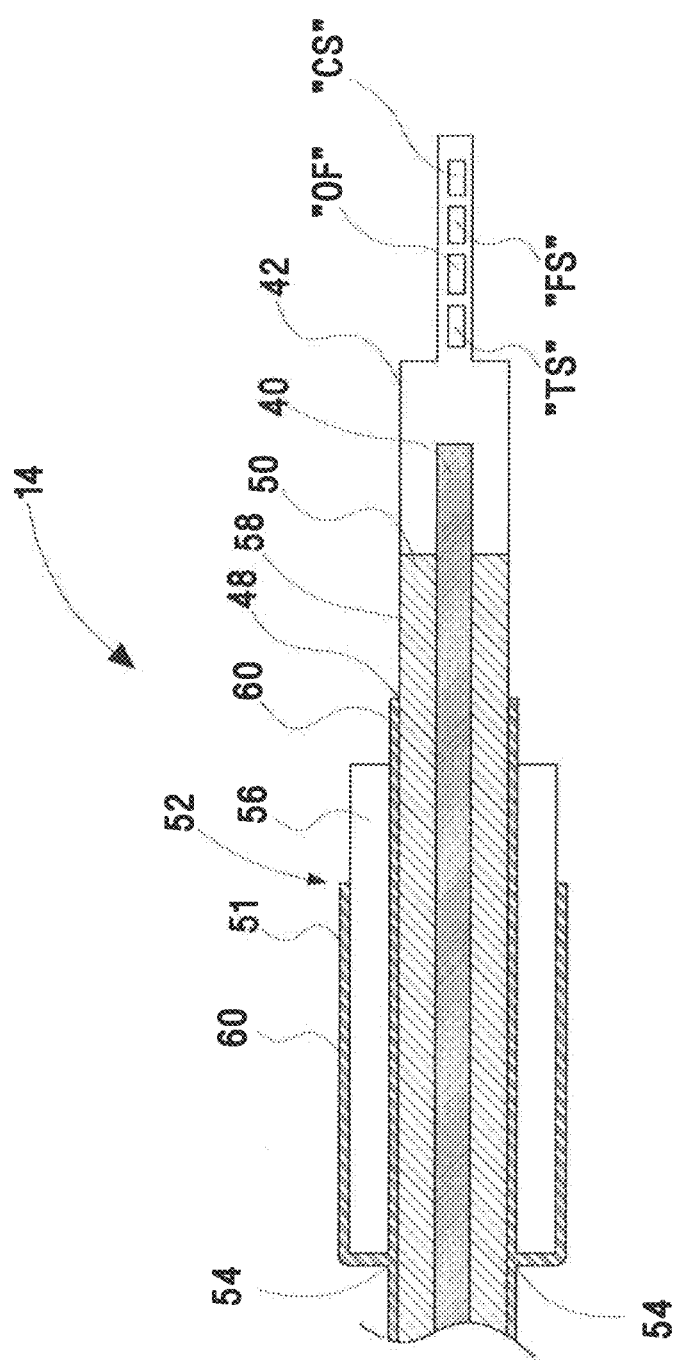
FIG. 5 is a cross-sectional view taken along line section 5-5 in FIG. 4.

Referring now to FIGS. 4 and 5, the ablation catheter 14 is illustrated. Ablation catheter 14 includes a coaxial cable 36. Coaxial cable 36 includes a proximal end 38 that couples to port 26b (shown in FIG. 1) that provides electrical connection to the inner conductor 40 and outer conductor 48 of the coaxial cable 36 and the energy source 16.

A distal radiating section 42 is provided at a distal end 44 of the coaxial cable 36 and is configured to receive the inner conductor 40, as best seen in FIG. 5. The distal radiating section 42 may be formed from any suitable material. In embodiments, the distal radiating section 42 may formed from ceramic or metal, e.g., copper, gold, silver, etc. The distal radiating section 42 may include any suitable configuration including but not limited to a blunt configuration, flat configuration, hemispherical configuration, pointed configuration, bar-bell configuration, tissue piercing configuration, etc. The distal radiating section 42 may couple to the distal end 44 of the coaxial cable via soldering, ultrasonic welding, adhesive, or the like. In one embodiment the distal radiating section 42 is sealed to the inner conductor 40 and a dielectric 50 to prevent fluid from contacting the inner conductor 40. As an alternative, the seal may be just between the inner conductor 40 and the dielectric 50.

An outer conductor 48 is braided and extends along the dielectric 50 positioned between the inner and outer conductors 40, 48, respectively (FIG. 5). As defined herein braided means made by intertwining three or more strands, and while described as a braid, the actual construction is not so limited and may include other formations of outer conductors of coaxial cables as would be understood by those of ordinary skill in the art. One advantage of a braided configuration of the outer conductor 48 is that it provides the ablation catheter 14 with the flexibility to move within the relatively narrow luminal structures such as the airways of the lungs of a patient. Additionally, through the use of flat wire braiding and follow on braid compression with an appropriately sized die, the cross sectional dimension of the braided conductor may be minimized significantly in comparison to other conductive structures, such as a drawn copper tubing, while maintain an acceptable electrical performance.

A choke or balun 52 is formed in part of a conductive layer 51 that extends along a portion of the coaxial cable 36. The conductive layer 51 may be a braided material of similar construction as the outer conductor 48 and is connected to the outer conductor 48. Specifically, a portion of the outer conductor 48 is shorted (e.g., soldered, interbraided or otherwise affixed) to a proximal portion 54 of the conductive layer 51.

The balun 52 also includes an insulative layer 56, which may be formed of a polytetrafluoroethylene (PTFE). The insulative layer 56 is generally formed between the conductive material 52 and the outer conductor 48. The insulative layer 56 extends distally past a distal end of the conductive material 52. The insulative layer 56 and its orientation extending beyond the conductive layer can be adjusted during manufacture to control the overall phase, energy field profile, and temperature response of the coaxial cable 36.

The outer conductor 48 extends distally beyond the insulative layer 56. A portion of the outer conductor 48 is removed to expose the dielectric 50 of the coaxial cable 36 and form a feedgap 58. The feedgap 58 is located distally from the balun 52 and proximal of and immediately adjacent the distal radiating section 42. The feedgap 58 and distal radiating section 42 are located and dimensioned to achieve a specific radiation pattern for the ablation catheter 14.

The ablation catheter 14 may optionally include an outer sheath 62 that extends to the proximal end 54 of the balun 52. Alternatively, no outer sheath 62 is employed and just a thin layer of insulative material 60 (e.g., a layer of polyethylene terephthalate (PET)) may be used to cover a portion of the outer conductor 48, and the balun 52 up to the point the insulative layer 56 extends beyond the conductive layer 51 of the balun 52 (FIG. 5). In yet a further embodiment the layer of PET 60 may be configured to extend proximally along the length of the coaxial cable 36 to assist in maintaining the braided configuration of the outer conductor 48 and conductive layer 51. As will be appreciated by those of skill in the art, removal of the outer sheath 62 and replacing it with a thin material, either along the length of the coaxial cable 36 or just at the balun 52 increases the flexibility of the ablation catheter 14. This added flexibility is beneficial for enabling greater ranges of movement when the ablation catheter 14 is used in luminal networks having small diameters and having a branched structure of multiple sharp turns, as will be described in greater detail below.

The flexibility of the ablation catheter 14 can be altered to accommodate a specific surgical procedure, a specific luminal structure, specific target tissue, a clinician's preference, etc. For example, in an embodiment, it may prove advantageous to have an ablation catheter 14 that is very flexible for movement through the relatively narrow airway of the lungs of a patient. Alternatively, it may prove advantageous to have an ablation catheter 14 that is only slightly flexible, e.g., where the ablation catheter 14 is needed to pierce or puncture target tissue. Still further, to achieve the desired amount of flexibility it may be desirable to form the balun 52 in a manner consistent with the disclosure of U.S. patent application Ser. No. 13/834,581 entitled "Microwave Energy-Delivery Device and System", filed on Mar. 15, 2013 by Brannan et al., the entire contents of which is incorporated herein by reference. Still further, although the microwave ablation catheter described here may be specific, it should be understood to those of skill in the art that other microwave ablation catheter embodiments, either simplified or more complex in structural detail, may be employed without departing from the scope of the instant disclosure.

In embodiments, a temperature monitoring system 3 (FIG. 1), e.g., microwave thermometry, may be utilized with the ablation catheter 14 to observe/monitor tissue temperatures in or adjacent an ablation zone. In an embodiment, for example, one or more temperature sensors "TS" may be provided on the ablation catheter 14, e.g., adjacent the distal radiating section 42 (as shown in FIG. 5) and may be configured to measure tissue temperatures in or adjacent an ablation zone. The temperature monitoring system 3 can be, for example, a radiometry system, a thermocouple based system, or any other tissue temperature monitoring system known in the art. The temperature monitoring system 3 may be incorporated into the energy source 16 to provide feedback to the energy source, or alternatively be housed in a separate box providing audible or visual feedback to the clinician during use of the ablation catheter 14. In either embodiment, the temperature monitoring system 3 may be configured to provide tissue temperature and ablation zone temperature information to the energy source 16 (or other suitable control system). In embodiments, temperature sensors 3 may be included along the coaxial cable 36, or along assembly 12 (described with reference to FIG. 1), or along the EWC 90 to provide a greater array of temperature data collection points and greater detail on the temperature of the tissue following application of energy.

In at least one embodiment, the tissue temperature and/or ablation zone temperature information may be correlated to specific known ablation zone sizes or configurations that have been gathered through empirical testing and stored in one or more data look-up tables and stored in memory of the temperature sensing monitoring system 3 and/or the energy source 16. The data look-up tables may be accessible by a processor of the temperature sensing monitoring system 3 and/or the energy source 16 and accessed by the processor while the distal radiating section 42 is energized and treating target tissue. In this embodiment, the temperature sensors "TS" provide tissue temperature and/or ablation zone temperature to the microprocessor which then compares the tissue temperature and/or ablation zone temperature to the known ablation zone sizes stored in the data look-up tables. The microprocessor may then send a command signal to one or more modules of the temperature sensing monitoring system 3 and/or the energy source 16 to automatically adjust the microwave energy output to the distal radiating section 42. Alternatively, a manual adjustment protocol may be utilized to control the microwave energy output to the distal radiating section 42. In this embodiment, the microprocessor may be configured to provide one or more indications (e.g., visual, audio and/or tactile indications) to a user when a particular tissue temperature and/or ablation zone temperature is matched to a corresponding ablation zone diameter or configuration.

System 10, depicted in FIG. 1 is configured to treat tissue, and as further set forth in FIG. 7 enables a method of identifying target tissue (hereinafter simply referred to as "a target") utilizing computed tomographic (CT) images, and once identified further enables the use of a navigation or guidance system to place the catheter assembly 12 or other tools at the target. CT data facilitates the planning of a pathway to an identified target as well as providing the ability to navigate through the body to the target location, this includes a preoperative and an operative component (i.e., pathway planning and pathway navigation).

The pathway planning phase includes three general steps. The first step involves using software for generating and viewing a three-dimensional model of the bronchial airway tree ("BT") and viewing the CT data to identify targets. The second step involves using the software for selection of a pathway on the BT, either automatically, semi-automatically, or manually, if desired. The third step involves an automatic segmentation of the pathway(s) into a set of waypoints along the path that can be visualized on a display. It is to be understood that the airways are being used herein as an example of a branched luminal network. Hence, the term "BT" is being used in a general sense to represent any such luminal network (e.g., the circulatory system, or the gastro-intestinal tract, etc.)

Figure 6:
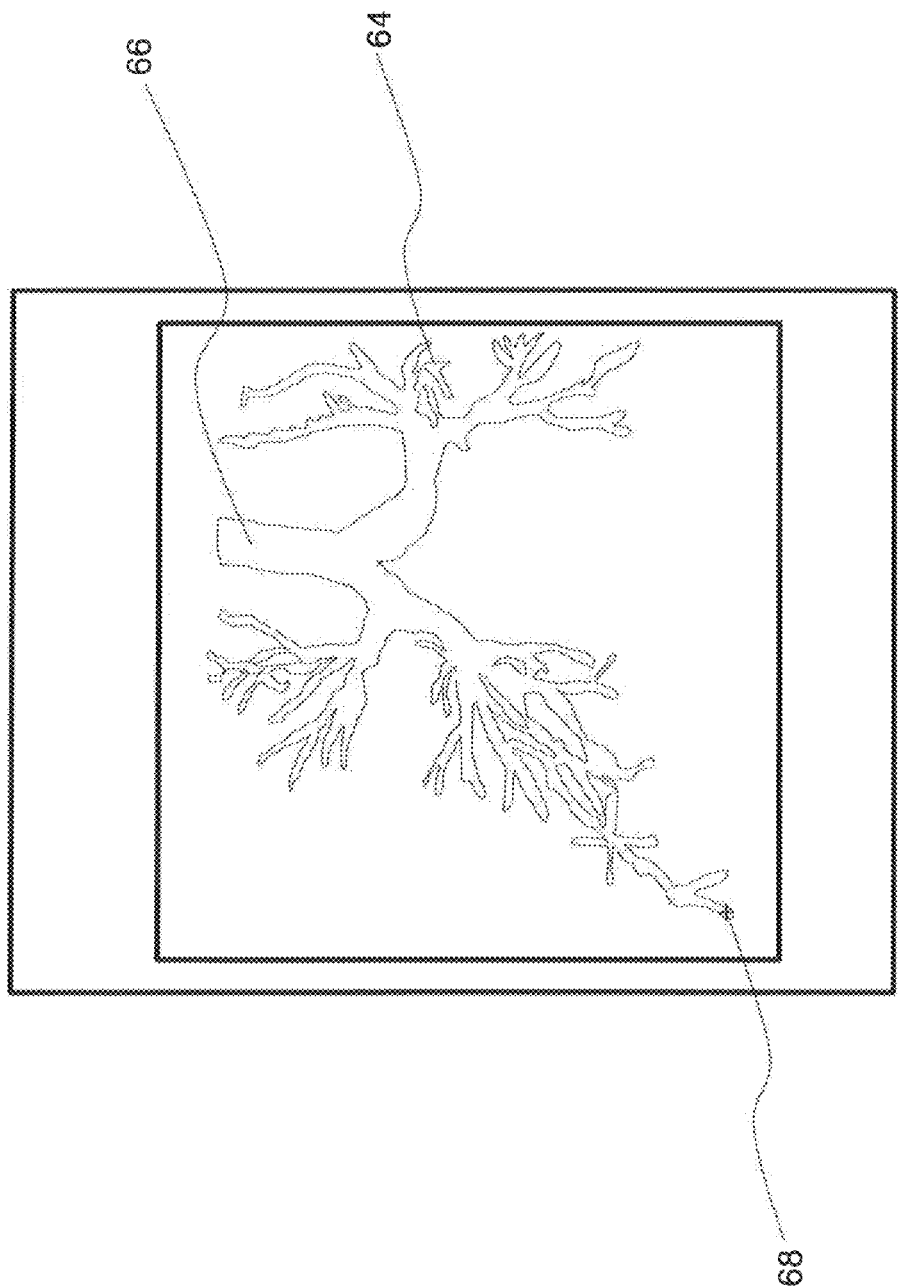
FIG. 6 is a screen shot of a CT based luminal navigation system in accordance with an embodiment of the present disclosure.

Using a software graphical interface 64 as shown in FIG. 6, generating and viewing a BT, starts with importing CT scan images of a patient's lungs into the software. The software processes the CT scans and assembles them into a three-dimensional CT volume by arranging the scans in the order they were taken and spacing them apart according to the setting on the CT when they were taken. The software uses the newly-constructed CT volume to generate a three-dimensional map, or BT, of the airways. The software then displays a representation of the three-dimensional map 66 on the software graphical interface 64. A user may be presented with various views to identify masses or tumors that the medical professional would like to biopsy or treat, and to which the medical professional would like to use the system 10 to navigate.

Next, the software selects a pathway to a target, e.g., target 68 identified by a medical professional. In one embodiment, the software includes an algorithm that does this by beginning at the selected target and following lumina back to the entry point. The software then selects a point in the airways nearest the target. The pathway to the target may be determined using airway diameter.

After the pathway has been determined, or concurrently with the pathway determination, the suggested pathway is displayed for user review. This pathway is the path from the trachea to the target that the software has determined the medical professional is to follow for treating the patient. This pathway may be accepted, rejected, or altered by the medical professional. Having identified a pathway in the BT connecting the trachea in a CT image with a target, the pathway is exported for use by system 10 to place a catheter and tools at the target for biopsy of the target and eventually treatment if necessary. Additional methods of determining a pathway from CT images are described in commonly assigned U.S. patent application Ser. No. 13/838,805 entitled "Pathway Planning System and Method", filed on Mar. 15, 2013, by Baker et al., the entirety of which is incorporated herein by reference.

Figure 7:
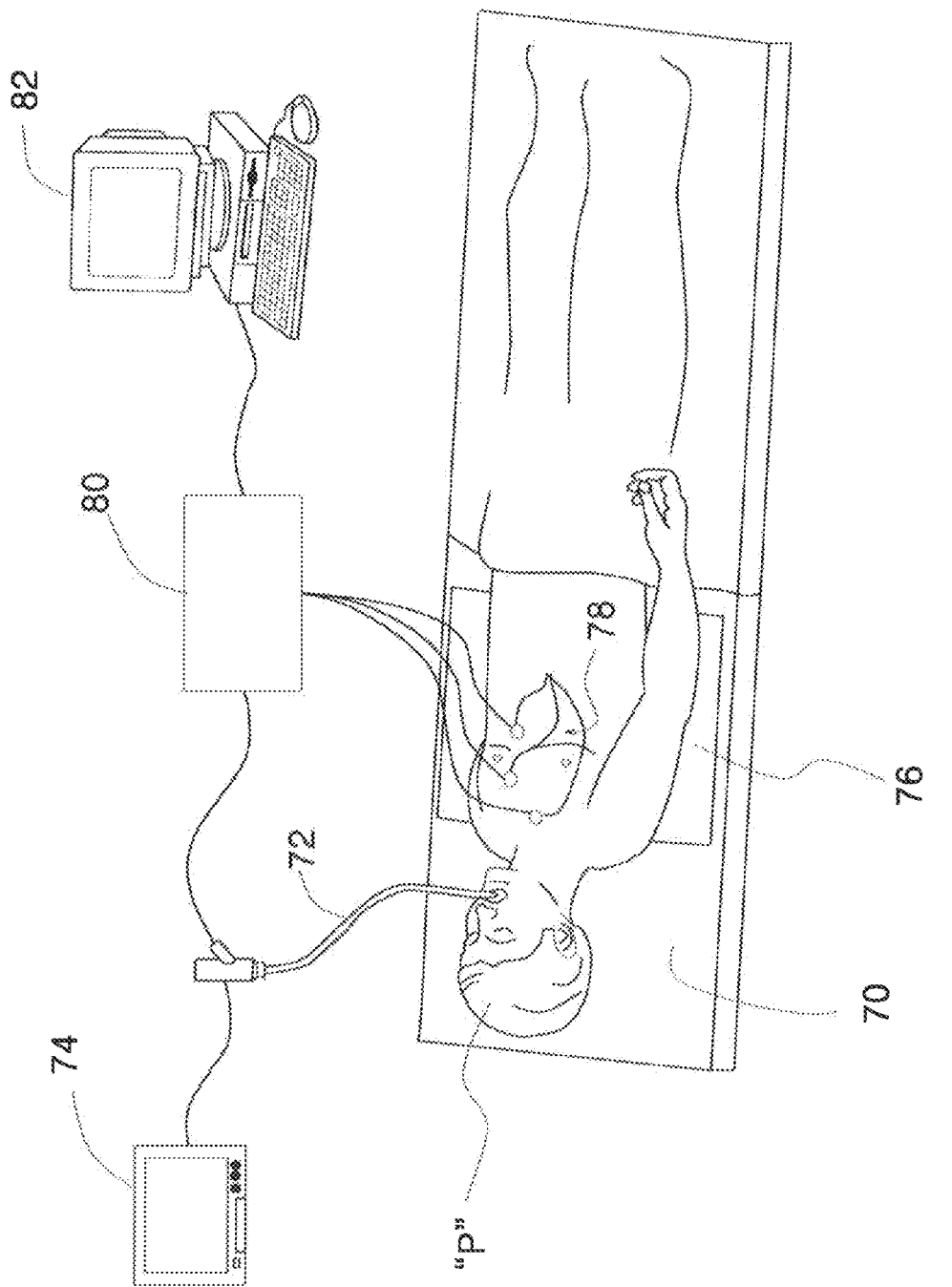
FIG. 7 is a perspective view of a microwave ablation system and luminal navigation system configured for use the microwave ablation catheter assembly shown in FIG. 1 and microwave ablation catheter shown in FIG. 2 in accordance with an embodiment of the present disclosure.

FIG. 7 shows a patient "P" lying on an operating table 70 and connected to a system enabling navigation along the determined pathway within the luminal network to achieve access to the identified target. A bronchoscope 72 is inserted into the patient's lungs. Bronchoscope 72 is connected to monitoring equipment 74, and typically includes a source of illumination and a video imaging system. In certain cases, the devices of the present disclosure may be used without a bronchoscope, as will be described below. System 10 monitors the position of the patient "P", thereby defining a set of reference coordinates. Specifically, system 10 utilizes a six degrees-of-freedom electromagnetic position measuring system according to the teachings of U.S. Pat. No. 6,188,355 and published PCT Application Nos. WO 00/10456 and WO 01/67035, which are incorporated herein by reference. A transmitter arrangement 76 is implemented as a board or mat positioned beneath patient "P." A plurality of sensors 78 are interconnected with a tracking module 80 which derives the location of each sensor 78 in 6 DOF (degrees of freedom). One or more of the reference sensors 78 (e.g., 3 sensors 78) are attached to the chest of patient "P" and their 6 DOF coordinates sent to a computer 82 (which includes the software) where they are used to calculate the patient coordinate frame of reference.

Figure 8:
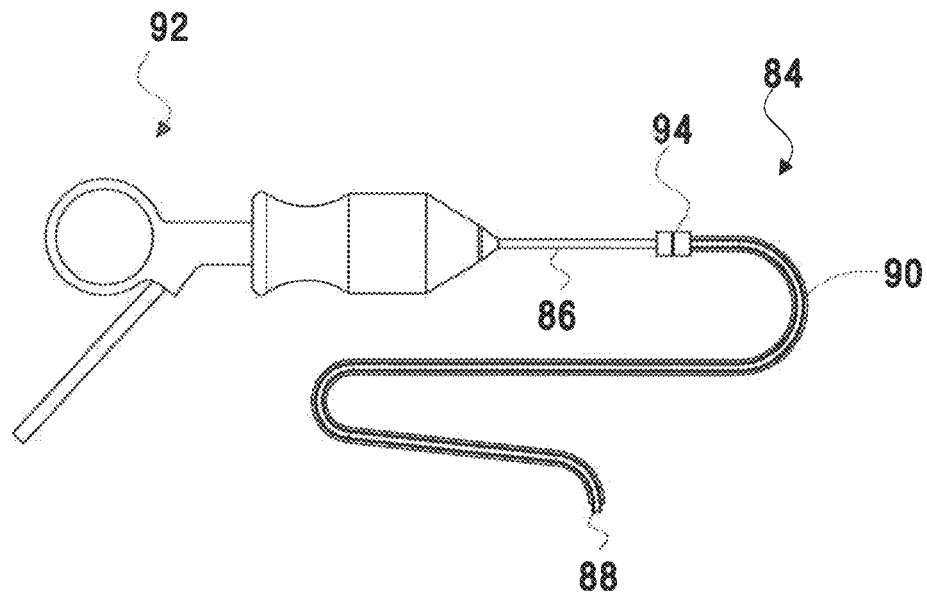
FIG. 8 is a side view of a luminal catheter delivery assembly including an extended working channel and locatable guide catheter in accordance with an embodiment of the present disclosure.
Figure 9:
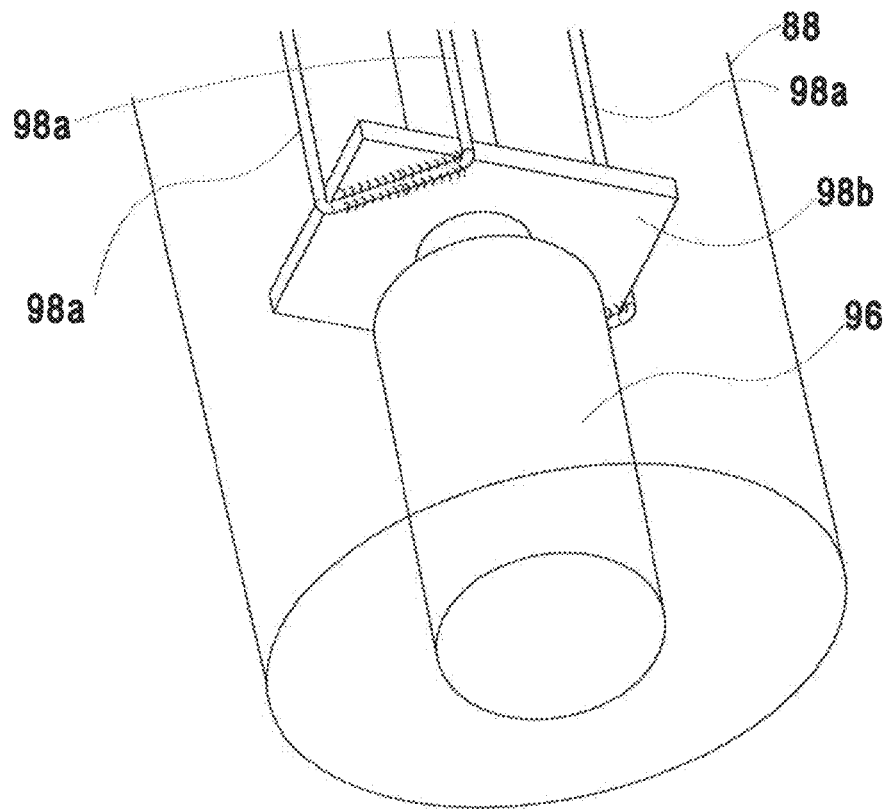
FIG. 9 is a partial, perspective view of a distal end of the locatable guide catheter shown in FIG. 8.

FIG. 8 depicts a positioning assembly 84, constructed and operative according to the teachings of the present disclosure. Positioning assembly 84 includes a locatable guide 86 which has a steerable distal tip 88, an extended working channel 90 and, at its proximal end, a control handle 92.

There are several methods of steering the extended working channel 90. In a first method, a single direction of deflection may be employed. Alternatively, a multi-directional steering mechanism with a manual direction selector may be employed to allow selection of a steering direction by the practitioner without necessitating rotation of the catheter body. With multi-directional steering four elongated tensioning elements ("steering wires") 98a are implemented as pairs of wires formed from a single long wire extending from handle 92 to distal tip 88. Steering wires 98a are bent over part of a base 98b and return to handle 92. Steering wires 98a are deployed such that tension on each wire individually will steer the distal tip 88 towards a predefined lateral direction. In the case of four steering wires 98a, the directions are chosen to be opposite directions along two perpendicular axes. In other words, the four steering wires 98a are deployed such that each wire, when actuated alone, causes deflection of the distal tip 98 in a different one of four predefined directions separated substantially by multiples of 90°.

Locatable guide 86 is inserted into the extended working channel 90 within which it is locked in position by a locking mechanism 94. A position sensor element 96 of system 10 is integrated with the distal tip 88 of the locatable guide 86 and allows monitoring of the tip position and orientation (6 DOF) relative to the reference coordinate system.

Figure 10:
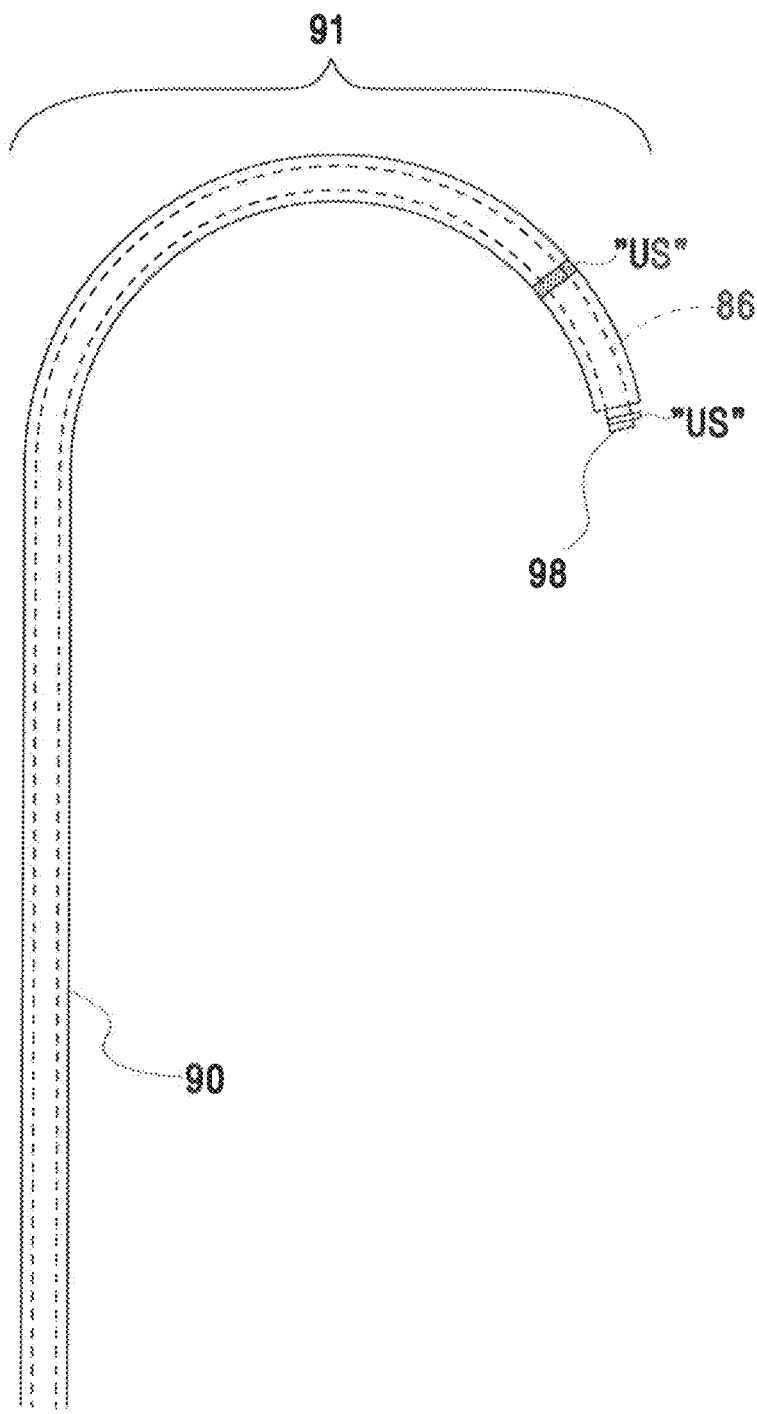
FIG. 10 is a side view of the extended working channel shown in FIG. 8 with the microwave ablation catheter extending from a distal end thereof.

In embodiments, locatable guide 86 may have a curved or hooked configuration as shown in FIG. 10. This alternative is currently marketed by Covidien LP under the name EDGED. In such a system, it is the extended working channel 90 that is formed with a curved tip 91. Differing amounts of pre-curve implemented in the extended working channel 90 can be used, however, common curvatures include 45, 90, and 180 degrees. The 180 degree extending working channel 90 has been found particular useful for directing the locatable guide 86 to posterior portions of the upper lobe of the lung which can be particularly difficult to navigate.

The locatable guide 86 is inserted into the extended working channel 90 such that the position sensor 96 projects from the distal tip 88 of the extended working channel 90. The extended working channel 90 and the locatable guide 86 are locked together such that they are advanced together into the lung passages of the patient "P." In this embodiment, the extended working channel 90 may include a steering mechanism similar to the one already described above. As can be appreciated, certain modifications may need to be made to the extended working channel 90 in order for the extended working channel to function as intended.

In embodiments, an integrated radial ultrasound probe "US" (FIG. 10) may be provided on the extended working channel 90, the locatable guide 86, catheter assembly 12 and/or the ablation catheter 14. For illustrative purposes, the ultrasound probe "US" is shown disposed on the extended working channel 90 and the locatable guide 86. The ultrasound probe "US" may be configured to provide ultrasound feedback to one or more modules of the system 10 during navigation and insertion of the ablation catheter 14 to facilitate positioning the ablation catheter 14 adjacent target tissue. As will be appreciated a US probe may also be used without the extended working channel but in conjunction with an endoscope for imaging central lesions that would be accessible to the endoscope. Furthermore, the US probe may be used to monitor treatment progression and/or confirm treatment completion.

As noted above, the present disclosure employs CT data (images) for the route planning phase. CT data is also used for the navigation phase. Specifically, the CT system of coordinates is matched with the patient system of coordinates; this is commonly known as registration. Registration is generally performed by identifying locations in both the CT and on or inside the body, and measuring their coordinates in both systems. Manual, semi-automatic or automatic registration can be utilized with the system 10. For purposes herein, the system 10 is described in terms of use with automatic registration. Reference is made to commonly assigned U.S. patent application Ser. No. 12/780,678, which is incorporated herein by reference, for a more detailed description of automatic registration techniques.

The automatic registration method includes moving locatable guide 86 containing position sensor 96 within a branched structure of a patient "P." Data pertaining to locations of the position sensor 96 while the position sensor 96 is moving through the branched structure is recorded using the transmitter arrangement 80. A shape resulting from the data is compared to an interior geometry of passages of the three-dimensional model of the branched structure. And, a location correlation between the shape and the three-dimensional model based on the comparison is determined.

In addition to the foregoing, the software of the system 10 identifies non-tissue space (e.g. air filled cavities) in the three-dimensional model. Thereafter, the software records position data of the position sensor 96 of the locatable guide 86 as the locatable guide 86 is moved through one or more lumens of the branched structure. Further, the software aligns an image representing a location of the locatable guide 86 with an image of the three-dimensional model based on the recorded position data and an assumption that the locatable guide 86 remains located in non-tissue space in the branched structure.

Figure 11:
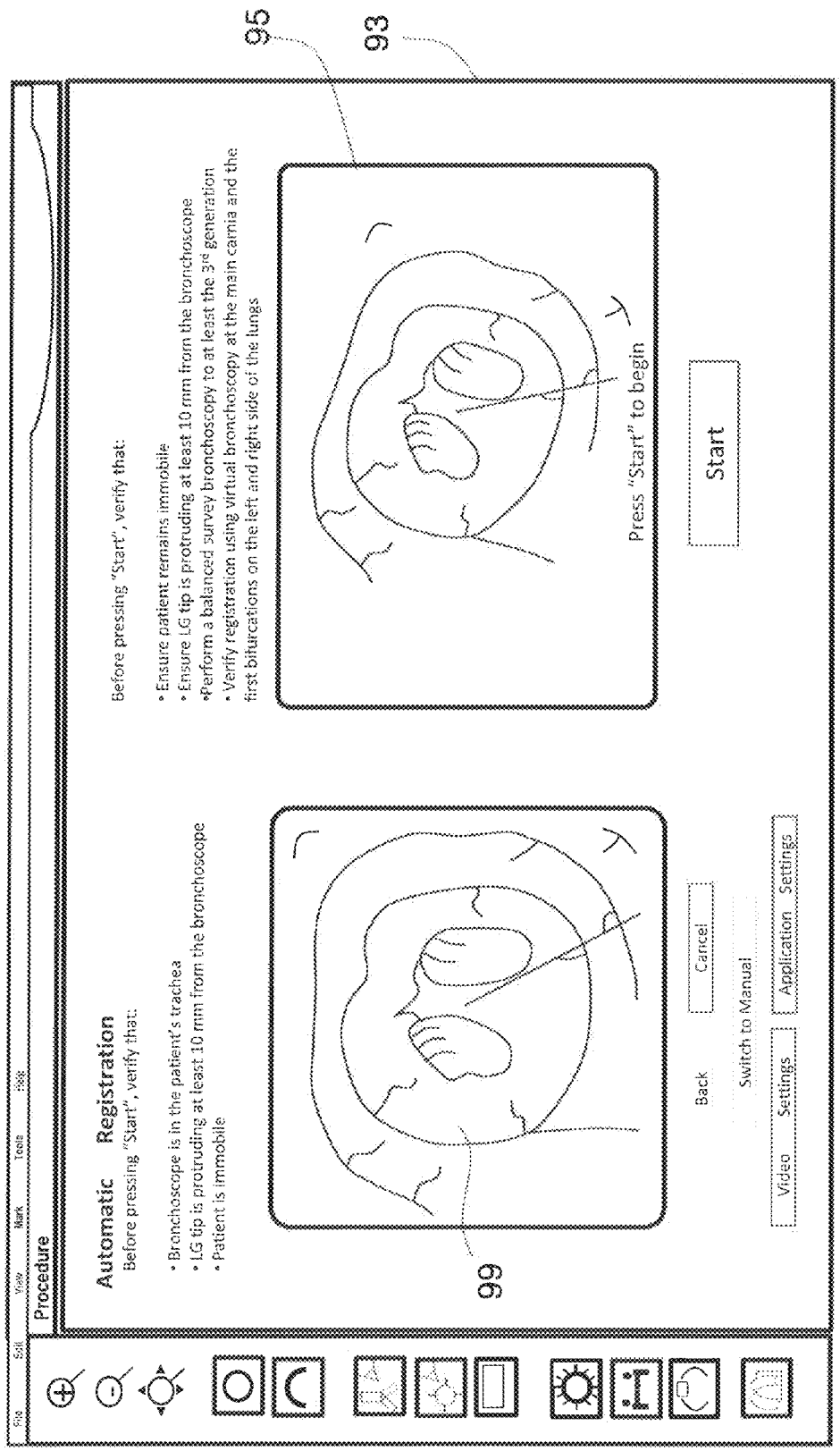
FIG. 11 is a screen shot of a CT based luminal navigation system in accordance with an embodiment of the present disclosure.
Figure 14:
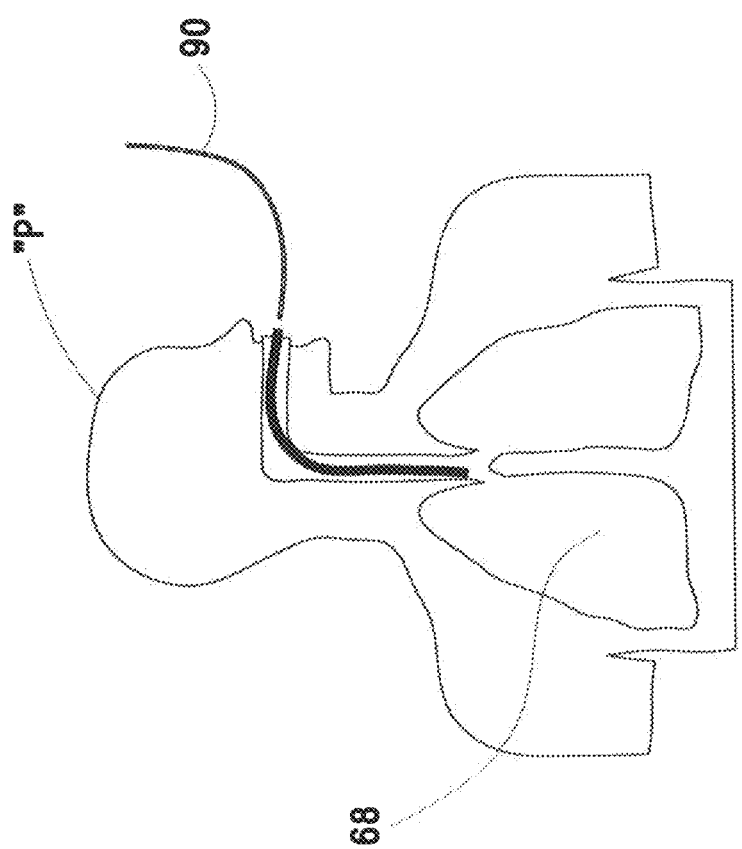
FIG. 14 is a schematic, plan view of the bronchoscope positioned within the trachea of the patient with the extended working channel removed from the bronchoscope.

Once in place in the patient "P," a screen 93 will be displayed by the software on the monitoring equipment 74 (FIG. 11). The right image is the actual bronchoscopic image 95 generated by the bronchoscope 72. Initially there is no image displayed in the left image 97, this will be a virtual bronchoscopy generated from the CT image data once registration is complete.

Starting with the locatable guide 86, and specifically the position sensor 96 approximately 3-4 cm above the main carina, as viewed through the bronchoscope 72, the bronchoscope 72 is advanced into both the right and left lungs to, for example, the fourth generation of the lung passages. By traversing these segments of the lungs, sufficient data is collected as described above such that registration can be accomplished.

Now that the targets have been identified, the pathway planned, the bronchoscope 72 including locatable guide 86 inserted into the patient "P," and the virtual bronchoscopy image registered with the image data of the bronchoscope 72, the system 10 is ready to navigate the position sensor 96 to the target 68 within the patient's lungs. The computer 80 provides a display similar to that shown in FIG. 11 identifying the target 68 and depicting the virtual bronchoscopy image 99. Appearing in each of the images on the display is the pathway from the current location of the position sensor 96 to the target 68. This is the pathway that was established during the pathway planning phase discussed above. The pathway may be represented, for example, by a colored line. Also appearing in each image is a representation of the distal tip 88 of the locatable guide 86 and position sensor 96. Once the pathway is established, a clinician may utilize system 10 to treat the target tissue 68.

Operation of the system 10 to treat target tissue is described with reference to FIGS. 12A-16C. It is assumed the pathway to the target 68 had been ascertained via the methods described above. After, advancing the bronchoscope 72 including the extended working channel 90 and the locatable guide 86 to a point of being wedged within the luminal network, the extended working channel and locatable guide are further advanced along the identified pathway to the target 68 (see FIGS. 12A-12C).

In some cases the target tissue may be directly accessed from within the lumen (such as for the treatment of the endobronchial wall for COPD, Asthma, lung cancer, etc.), however in other instances, the target is not in direct contact with the BT and use of the locatable guide alone does not achieve access to the target. Additional access tools may be required to cross the lumen and access the target tissue (such as for the treatment of disease within the parenchyma).

Final localization and confirmation of the locatable guide or access tool with extended working channel may be performed with imaging and/or navigational guidance (this may include the same or different combinations of imaging and navigation techniques listed above).

Once the locatable guide 86 or an additional access tool has successfully been navigated to the target 68 location, the locatable guide 86 or access tool may be removed, leaving the extended working channel 90 in place as a guide channel for a biopsy tool 84 to the target 68 location (FIGS. 13A-13B). The medical tools may be biopsy tools that can be used to sample the target 68. Details of this system are included in U.S. Pat. No. 7,233,820, already incorporated herein by reference.

Once the locatable guide 86 has successfully been navigated to the target 68 location, the locatable guide 86 may be removed, leaving the extended working channel 90 in place as a guide channel for bringing a tool 84 to the target 68 location (FIGS. 13A-13B). The medical tools may be biopsy tools that can be used to sample the target 68. These samples are retrieved and sent to pathology for analysis to determine if treatment of the target is necessary. The biopsy analysis can happen in real time after the biopsy procedure such that the ablation can be performed immediately, or there can be some period of time, e.g., hours, days, weeks, between the time when the biopsy is taken and when the ablation procedure is performed.

If it is determined that the target 68 requires treatment (e.g., ablation), the assembly 12 including the ablation catheter 14 may be positioned through the bronchoscope 72 and the extended working channel 90 to enable treatment. Placement of the assembly may occur after the extended working channel 90 has been navigated to the target 68, or the extended working channel 90 may be navigated with the assembly 12 to reach the target 68. This second option may require a sensor providing 6 DOF positioning within either the extended working channel 90 or the assembly 12. As noted above, the braided configuration of the outer conductor 48 and the conductive layer 51 of the balun 52 in combination with the lumen configurations depicted in FIGS. 2-3, provides the assembly 12 with the needed flexibility to move within the relatively narrow airways.

In embodiments, the target tissue "T" may be pierced or penetrated to allow placement of the distal radiating section 42 within the target 68 (e.g., centered within the mass for treatment). For example, a guide wire, piercing tool, a biopsy tool 84 or the distal end 21 of the assembly 12 (described with reference to FIG. 1) may be utilized to pierce or penetrate the target 68. In the instance where the guide wire or piercing tool is utilized to penetrate or pierce tissue, the guide wire or piercing tool may passed through the extended working channel 90 to penetrate the target 68. Once pierced, the extended working channel 90 may be held in place and the guide wire or piercing tool removed to allow the assembly 12, housing the ablation catheter 14, to be inserted into the opening created by the tool or the guide wire in the target 68. Alternatively, while the guide wire or piercing tool is in the target 68, the extended working channel 90 may be extended to place the distal end of the extended working channel 90 within the opening created in the target 68. Following placement of the extended working channel 90 within the target 68, the guide wire or piercing tool can be removed to allow for insertion of the assembly 12 including ablation catheter 14. This second method helps assure proper placement of the ablation catheter 14, housed within the assembly 12, into the target 68.

One or more imaging modalities may be utilized to confirm that the ablation catheter 14 has been properly positioned (e.g. within the target 68.) For example, computer tomography (CT), ultrasound, fluoroscopy, and other imaging modalities may be utilized individually or in combination with one another to confirm that the ablation catheter 14 has been properly positioned within the target 68. One methodology employing both CT and fluoroscopy imaging modalities is described in commonly assigned U.S. application Ser. No. 12/056,123 entitled "CT-Enhanced Fluoroscopy," the contents of which is incorporated herein by reference.

Yet a further alternative method of ablation catheter 14 placement confirmation is disclosed herein. FIG. 46A represents a live fluoroscopic image depicting the placement of an extended working channel 90 and an ablation assembly 12 or biopsy tool 84 extending therefrom, after performing one of the navigation procedures described herein. FIG. 46B is a virtual fluoroscopic image depicting the same patient and displaying a target 68 thereon. The virtual fluoroscopic image is generated from the same CT data used in both the planning and navigation methods described above. The CT data is manipulated to create a computer model of a fluoroscopic image of the patient. The target 68 is the same target 68 identified in the planning phase, and the location of the target 68 in the virtual fluoroscopic image corresponds to the location of the target identified by the clinician during planning The virtual fluoroscopic image and the live fluoroscopic image may be registered to one another. This may be done using, for example, one or more fiducial markers placed either prior to the CT scan and that will also appear on the fluoroscopic image, or by identifying landmarks within the physiology that may act as fiducial markers (e.g., curvature and spacing of the rib cage). The two images, the live fluoroscopic image and the static virtual fluoroscopic image provide the clinician with the ability to compare placement of the extended working channel 90 and the ablation assembly 12 with the location of the target 68. This may be done in either a side by side comparison mode as shown in FIGS. 46A and 46B. For example, in FIG. 46A, the live fluoroscopic image, a mass 67 that has been identified as the target 68 during the planning phase may only be lightly visible under fluoroscopy, often soft tissue is difficult to discern in fluoroscopic images, but by comparing the location of the extended working channel 90 and the ablation assembly 12 as shown in FIG. 46A to the location of the target 68 shown in FIG. 46B, the necessary adjustments to positioning for proper ablation can be readily ascertained.

Alternatively, where the live and the virtual fluoroscopic images are registered to one another, comparison may be made by overlaying the virtual image (FIG. 46B) over the live image (FIG. 46 A) such that a composite image is created. This composite image then depicts the relative position of the target 68 to the placement of the ablation assembly 12 and extended working channel 90. By continuing live fluoroscopy visualization of the placement of the extended working channel 90 and/or the ablation assembly 12, or a biopsy tool 84 into the target 68 is enabled, thus enabling the clinician to actually see the proper placement into a target 68 in real time using a combination of a live fluoroscopic image and an overlaid virtual fluoroscopic image. Once placement of the ablation catheter 14 is confirmed within the target 68, microwave energy can be transmitted to the ablation catheter 14 to treat the target 68.

Following treatment of the target 68, one of the aforementioned imaging modalities may be utilized to confirm that a suitable ablation zone has been formed around the target 68 and to determine whether additional application of energy are necessary. These steps of treating and imaging may be repeated iteratively until a determination is made that the target has been successfully ablated. Moreover, the methodology described above using the imaging modalities to confirm the extent of treatment and determine whether additional application of energy is necessary can be combined with the radiometry and temperature sensing techniques described above to both confirm what is depicted by the imaging modality and to assist in determining treatment cessation points.

In an embodiment, such as, for example, when the target 68 is relatively close to a distal end of the bronchoscope 72, the extended working channel 90 may be removed (FIG. 14), or not used at all, and the bronchoscope 72 kept in place to visually guide access tools and the assembly 12 including the ablation catheter 14 to target 68. Alternately, the extended working channel 90 and accompanying access tools may be placed without use of the bronchoscope 72, or the bronchoscope 72 can be removed after placement of the extended working channel 90 in combination with access tools at the target 68 and kept in place and the assembly 12 including the ablation catheter 14 can be extended through the extended working channel 90 to treat the target 68.

As noted above, temperature monitoring system 3 can be used to determine and monitor temperature of the target tissue 68, ablation zone size, etc. In embodiments, the temperature monitoring system 3 can incorporated into one or more components (e.g., software graphical interface 64) that are configured for use with the system 10.

In embodiments, placement of the extended working channel 90 and/or the ablation catheter 14 within the luminal network may accomplished without the use of the aforementioned pathway planning and pathway navigation methods. In this instance, computer tomography, ultrasound and/or fluoroscopy mat be utilized to facilitate positioning the extended working channel 90, and/or access tools and/or the ablation catheter 14 within the luminal network.

In embodiments, the distal radiating section 42 may be covered by a temperature sensitive "wax" material "W" that melts when energy is applied to the inner conductor 20, thereby absorbing heat from the distal radiating section 42 by changing phase.

Moreover, in place of fluid cooling the distal radiation section 42 may be frozen to create an ice formation therearound. When the distal radiating section is energized, the ice turns to gas which may result in high heat dissipation, which, in turn, cools the distal radiating section 42.

Further, in accordance with the instant disclosure, it may prove advantageous to utilize the ablation catheter 14 without the assembly 12. In this particular embodiment, the extended working channel 90 may be modified to provide for fluid cooling of the ablation catheter 14, for example one of the aforementioned lumen and port configurations and a closed distal tip. As can be appreciated, one or more other modifications may also have to be made to the extended working channel 90 in order for the extended working channel 90 to function as intended herein.

FIGS. 15A-15B illustrate an extending working channel 190 having a closed distal end and a modified catheter assembly 12 inserted therein. Rather than a closed distal end as shown in FIG. 1, the catheter assembly 12 has an open distal end. A space between the inner surface of the extended working channel 190 and the catheter assembly 12 establishes a fluid inflow lumen 119a. A fluid outflow lumen 119c is exposed by the opening of the distal end of the catheter assembly 12. The lumens 119a and 119c allow for cooling fluid to flow in the extended working channel 190 and catheter assembly 12 to cool an the ablation catheter 14 located within the catheter assembly 12. A cross section of the extended working channel 190 with modified catheter assembly 12 is shown in FIG. 16D. The catheter assembly 12 may optionally include a position sensor 96 such that the catheter assembly 12 acts as a locatable guide 86 (FIG. 12) to assist in the positioning of the extended working channel at a target 68. The extended working channel 190 may be formed to meet the flexibility criteria described above. Alternatively, the extended working channel may be placed as described above using a locatable guide 86 Thereafter, the locatable guide 86 may be removed and the extended working channel 190 kept in place. With the locatable guide 86 removed, the modified catheter assembly 12 and ablation catheter 14 may be positioned within the extended working channel 190 (FIG. 16A) and energized to form an ablation zone "AB" suitable for treating target 68 (FIG. 16B). FIG. 16C shows yet another optional configuration, where the ablation catheter 14 is placed into the extended working channel 190 without any assembly following placement of the extended working channel 190 and removal of the locatable guide 86. Water may be circulated within the extended working channel 190 to cool the distal radiating section in a manner as described above.

As can be appreciated, a result of the flexible assembly 12 including the ablation catheter 14 being inserted endobrachially is that the likelihood of pneumothoraces occurring is greatly reduced by navigating through the luminal branches of the lung. Moreover, the ability of the system 10 to create a pathway to target tissue takes the guess work out of positioning the locatable guide, the extended working channel and the assembly 12 including the ablation catheter 14.

From the foregoing and with reference to the various figure drawings, those skilled in the art will appreciate that certain modifications can also be made to the present disclosure without departing from the scope of the same. For example, one or modifications may be made in the way of device delivery and placement; device cooling and antenna buffering; and sensor feedback. The following are a variety of non-limiting examples of such modifications considered within the scope of the present disclosure.

I. Device Delivery and Placement

In accordance with the instant disclosure, various methods may be utilized to deliver the ablation catheter 14 and/or the extended working channel 90/190 into a desired location in the target tissue 68.

For example, to address the occurrence of bleeding within the patient as a result of biopsy or ablation, the bronchoscope may be employed to create tamponade; that is, the bronchoscope can be wedged into the bronchus to stop the bleeding at points the bronchoscope can reach. However, in accordance with the instant disclosure, the extended working channels 90/190 could be navigated to the target 68 and one or more expandable members may be provided on the extended working channels 90/190 to create tamponade. The expandable member, e.g., a balloon, can be inflated to stop bleeding at these remote locations.

Specifically, FIGS. 17 and 18 illustrate the extended working channels 90/190 including a balloon "B" that is positioned on an exterior surface of the extended working channels 90/190. The balloon "B" is initially in a deflated configuration (FIG. 17) for navigating the extended working channel 90/190 through a conductive airway and positioning the extended working channels 90/190 adjacent the target 68. Subsequently, the balloon is inflated for anchoring the extended working channel 90/190 in place and to create a tamponade (FIG. 18).

In the embodiment where the balloon "B" is provided on the extended working channel 90, one or more lumens may be provided on the extended working channel 90 and may be in fluid communication with the balloon "B" to provide one or more suitable fluids from the fluid source 32 to the balloon "B" to move the balloon "B" from the inflated configuration to the deflated configuration (and vice versa). Moreover, in this embodiment, the balloon "B" may be configured to control local lung properties which change with respiration. For example, the relative permittivity of deflated lung tissue at 2450 MHz is 48 and the relative permittivity of inflated lung tissue at the same frequency is 20; this large permittivity range makes it difficult to tune an antenna to a single frequency. It has been found through empirical testing that by adding the balloon "B," the lung can be locally isolated during an inflated or deflated state to produce one or more desired properties, e.g., electrical and thermal. Specifically, thermal conductivity changes with inflation and deflation of the lungs. For example, if local respiration was stopped with the lung inflated and the ablation catheter 14 was matched to the target 68 with a relative permittivity of 45, heating can be focused thermally and electrically to the target 68. Likewise, if the lung were fixed in a deflated configuration, more lung tissue could be thermally treated to produce additional margin around the target 68.

FIGS. 19A-19B illustrate an ablation catheter 214 according to another embodiment of the present disclosure. Ablation catheter 214 is similar to ablation catheter 14. Accordingly, only those features unique to ablation catheter 214 are described in detail. An expandable balun 252 is provided on a coaxial cable 236. The balun 252 functions in a manner as described above with respect to the balun 52. Unlike balun 52, however, the balun 252 is expandable (air/fluid pressure) and configured to provide the functions of the balloon "B" as described above.

One or more lumens (not shown) may be provided on the ablation catheter 214 and configured to receive one or more suitable fluids from the fluid source 32 to move the balun 252 between the deflated and inflated configurations, see FIGS.

19A-19B. Alternatively, the lumens 19a, 19c of the assembly 12 may be in fluid communication with the balun 252 and configured to provide one or more suitable fluids from the fluid source 32 to the balun 252 to move the balun 252 between inflated and deflated configurations. As can be appreciated, other methods and/or devices may be utilized to move the balun 252 between inflated and deflated configurations.

Figure 20:
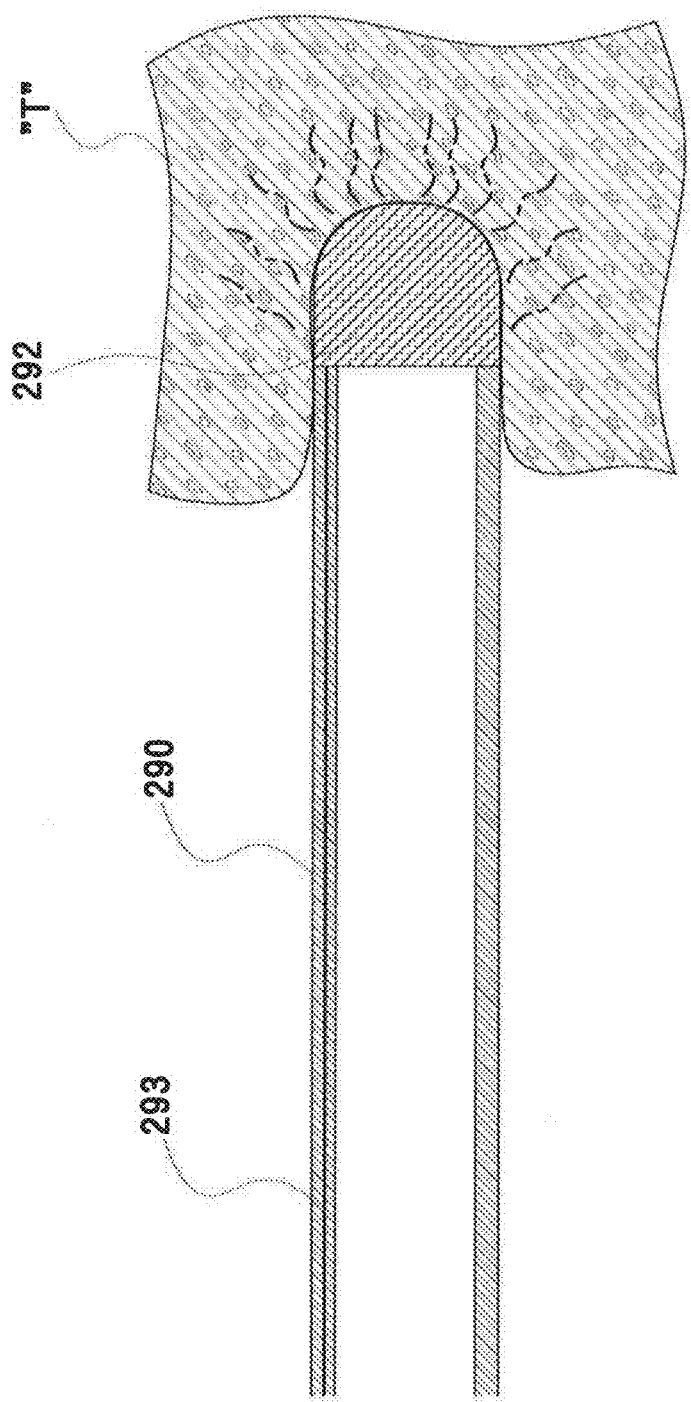
FIG. 20 is a schematic, plan view of a distal tip configuration that may be utilized with the microwave ablation catheter assembly shown in FIG. 1, the microwave ablation catheter shown in FIG. 2 or the extended working channel shown in FIG. 15A.

FIG. 20 illustrates an extended working channel 290 according to another embodiment of the instant disclosure. In this embodiment, a closed distal tip 291 is energizable for penetrating tissue "T." Specifically, an electrode 292 may be coupled at the distal tip 291 of the extending working channel 290. The electrode 291 may be in electrical communication with the energy source 16 via one or more leads or wires 293 that extend within the extended working channel 290. The electrode 292 may be configured for monopolar operation. A return pad (not shown) may be positioned on a patient and utilized as a return electrode. Alternatively, a second electrode (not shown) can be provided on the extended working channel 290 to create a bipolar electrode configuration. In use, when the electrode 291 is energized, the distal tip 291 may be utilized to penetrate tissue to facilitate positioning the extended working channel 290 adjacent target tissue.

Figure 21:
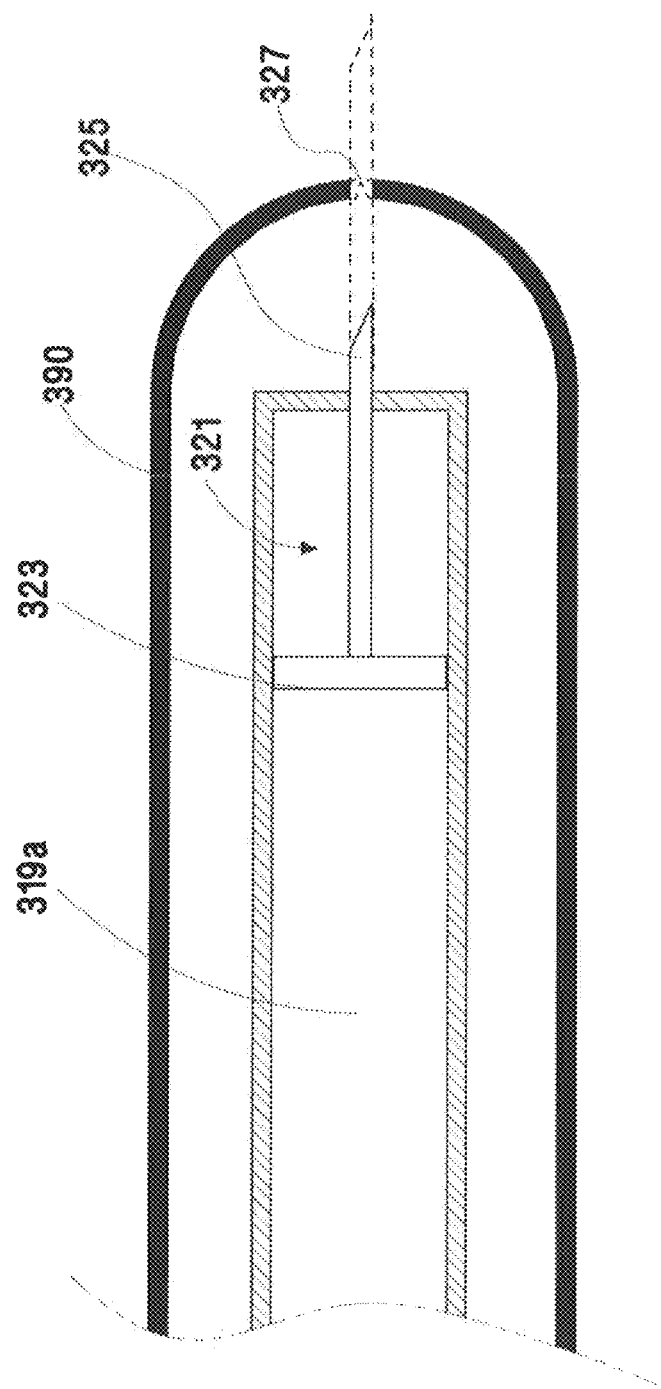
FIG. 21 is a schematic, plan view of an alternate embodiment of the extended working channel shown in FIG. 15A.

FIG. 21 illustrates an extended working channel 390 according to another embodiment of the instant disclosure. The extended working channel 390 includes a closed distal end and at least one water filled lumen or chamber (e.g., a lumen 319a of the cooling water loop utilized to cool the distal radiating section 42) that includes a piston assembly 321 including a base 323 and a needle 325 extending distally from the base and through an aperture (not shown) at a distal end of the lumen 319a. A seal (not shown) may be provided within the aperture of the lumen 319a to maintain the pressure within the lumen. An optional seal 327 may be provided at a distal tip of the extended working channel 390 and may be configured to maintain a fluid tight seal. The piston assembly 321 is movable within the lumen 319a to move the needle 325 from a retracted configuration to an extended configuration (shown in phantom in FIG. 21) through the seal 327. In the extended configuration, the needle 325 may be utilized to anchor the extended working channel 390 to tissue and/or penetrate tissue.

In use, water may be provided to the extended working channel 390 to move the needle 325 to the extended configuration for penetrating tissue; this may be done prior to energizing the distal radiating section 42 and/or when the distal radiating section 42 is energized. Thus, the cooling water loop serves a dual purpose (cooling of the distal radiating section and extension of the needle 325) and may eliminate the need for a separate push/pull member or sheath.

Figure 22:
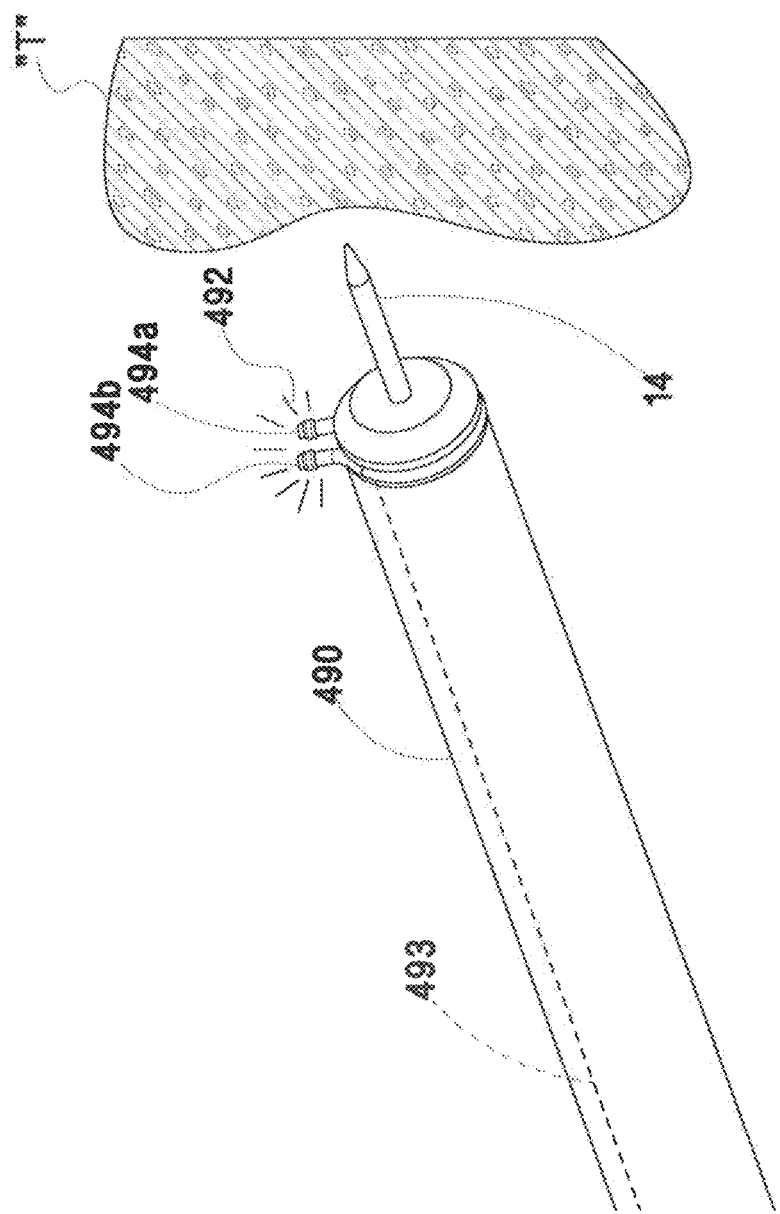
FIG. 22 is a schematic, plan view of yet another embodiment of the extended working channel shown in FIG. 15A.

FIG. 22 illustrates an extended working channel 490 according to another embodiment of the instant disclosure. The extended working channel 490 includes an open distal end and an electrode 492 operably coupled thereto. Electrode 492 is similar to the electrode 292 illustrated in FIG. 20. Unlike electrode 292, however, electrode 492 may extend along an outer peripheral surface of the extended working channel 490. Additionally, a pair of upright electrode extensions 494a, 494b may be provided on the electrode 492 and configured to function as a monopolar pencil to treat tissue.

The electrode 492 may be in electrical communication with the energy source 16 via one or more leads or wires 493 that extend within the extended working channel 490. The electrode 492 may be configured for monopolar operation. A return pad (not shown) may be positioned on a patient and utilized as a return electrode. Alternatively, a second electrode (not shown) can be provided on the extended working channel 490 to create a bipolar electrode configuration. In use, after tissue has been ablated, the upright extensions 494a, 494 may be utilized to transmit microwave energy (or RF) to neighboring tissue. After the tissue has been treated, the upright extensions 494a, 494b may be utilized to scrape the electrosurgically treated tissue. As can be appreciated, having the electrode 492 on the extended working channel 490, allows a user to treat tissue with the electrode 492 while leaving ablation catheter 14 in place within the extended working channel 490.

Figure 23:
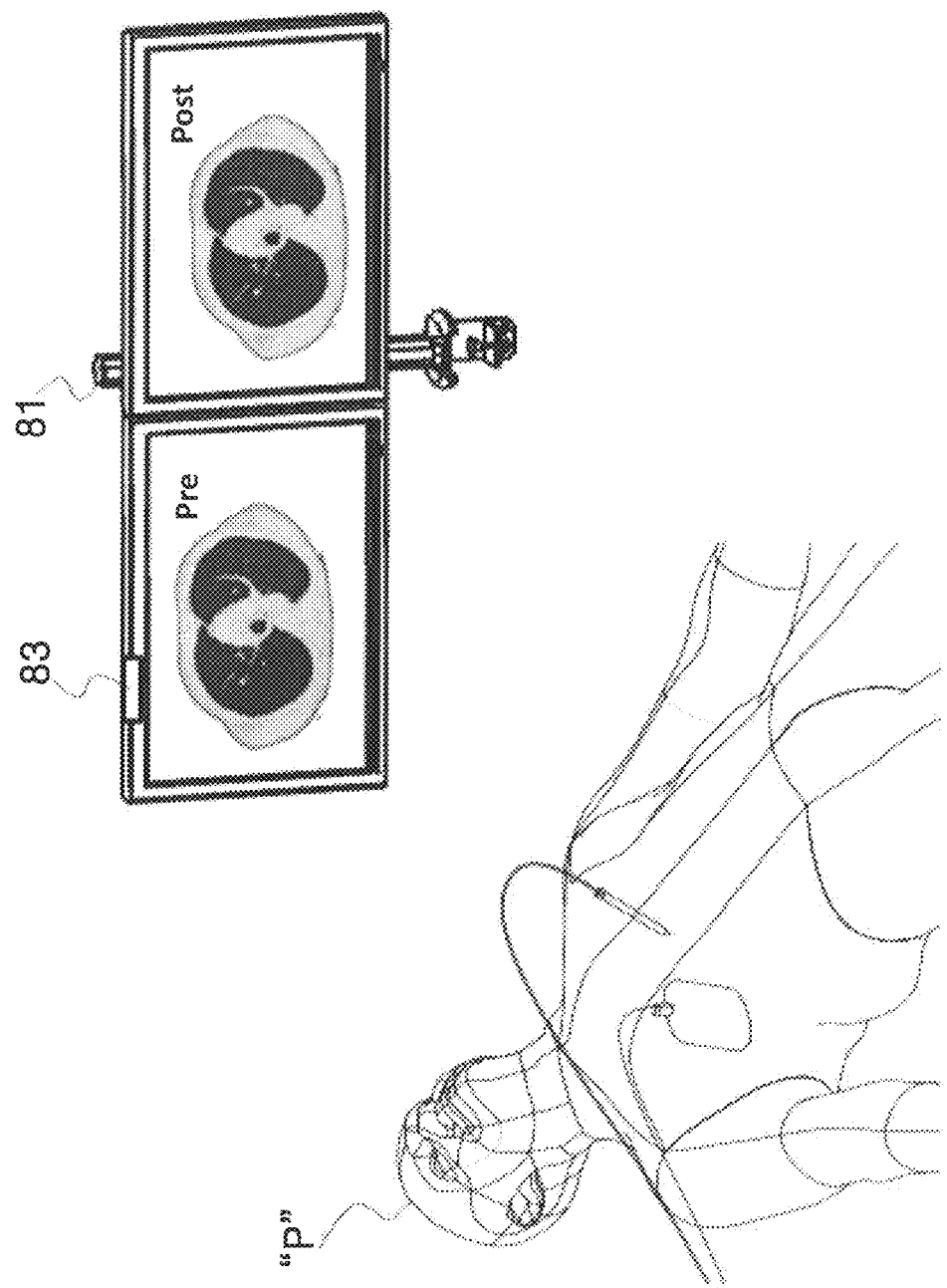
FIG. 23 is a perspective view of an alternate embodiment of the luminal navigation system shown in FIG. 7.

FIG. 23 illustrates a head-up display 81 (e.g., Google glasses) that communicates with the guidance system for providing a virtual internal image to a clinician. The virtual internal image includes information pertaining to planning the pathway to the target 68 and for guiding and navigating one of the aforementioned tools, extended working channels and the locatable guides through the lungs of a patient "P." The head-up display 81 may include one or more electromagnetic sensors 83 for providing a position of the head-up display 81 relative to a patient "P" for projecting the virtual internal image into a clinician's view of the patient "P" with the proper orientation.

II. Device Cooling and Antenna Buffering

The following embodiments are configured to protect a patient from unintended heating from the coaxial cable 36 and/or the distal radiating section 42 and/or configured to provide dielectric buffering to the distal radiating section 42.

FIGS. 24-26 illustrate an assembly 512 according to an embodiment of the instant disclosure. Assembly 512 is similar to assembly 12. Accordingly, only those features unique to assembly 512 are described in detail.

A partition 511 is provided within the housing 523 adjacent the distal end of the assembly 512 to provide a chamber 514 that is configured to isolate the distal radiating section 542 from the rest of the coaxial cable 536. A dielectric (e.g. ceramic, hydrogel, etc.) 513 is provided within the chamber 514 to cover the distal radiating section 542 and is configured to cool the distal radiating section 542 and the inner conductor 540 when contacted by fluid being transmitted through the lumens 519a, 519c and into contact with the partition 511. In accordance with the instant disclosure, the dielectric 513 is capable of withstanding heat without changing properties to buffer the distal radiating section 542 and create a separate active cooling system around the coaxial cable 536. This reduces, if not eliminates, phase changes around the distal radiating section 542 during activation thereof and may reduce the active cooling requirements on the coaxial cable 536.

Figure 27:
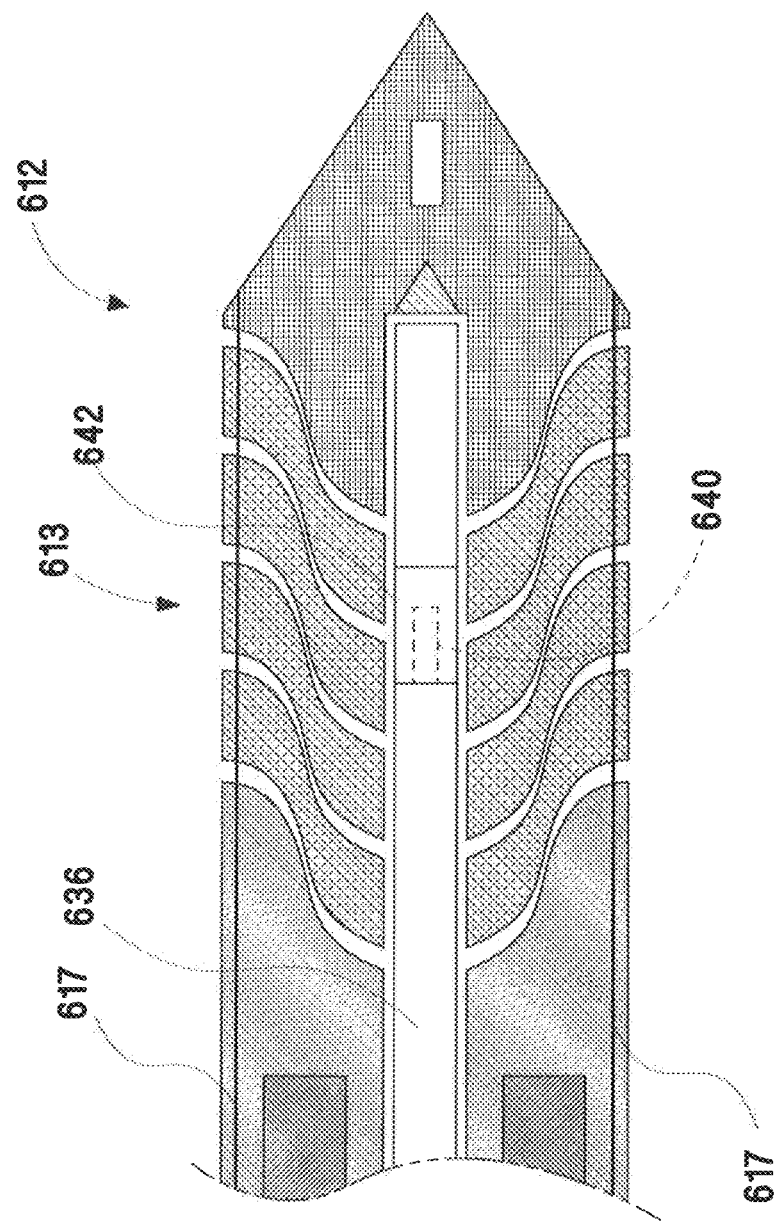
FIG. 27 is a partial, cutaway view of yet another embodiment of the microwave ablation catheter shown in FIG. 1.

FIG. 27 illustrates an assembly 612 according to an embodiment of the instant disclosure. A plurality of ceramic elements 613 extend at least partially along the coaxial cable 636 and form a nested configuration. The ceramic elements 613 serve as a heat sink to cool a distal radiating section 642 and an inner conductor 640. The ceramic elements 613 may be actuatable to move from a relaxed configuration wherein the plurality of ceramic elements 613 are spaced apart from one another (as shown in FIG. 27) to allow the coaxial cable 636 to flex, to a compressed configuration wherein the ceramic elements 613 are moved towards one another to increase cooling of the distal radiating section 642 and the inner conductor 640, and to secure the position of the location of the assembly. A pair pull wire 617 operably couples to the ceramic elements 613 and is configured to move the ceramic elements 613 to the compressed configuration.

Figure 28:
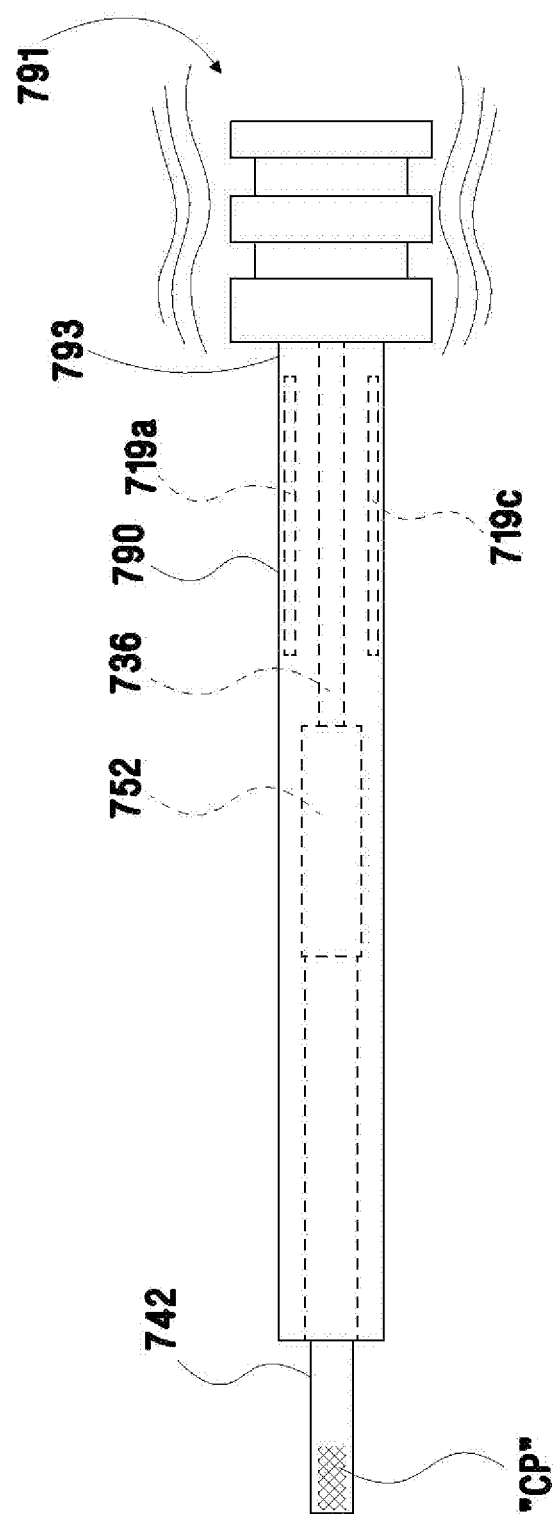
FIG. 28 is a schematic, plan view of still yet another embodiment of the microwave ablation catheter shown in FIG. 1.

FIG. 28 illustrates an extended working channel 790 according to an embodiment of the instant disclosure. The extended working channel 790 functions as a structural thermal sink that is configured to sink heat either by itself or in conjunction with a cooling fluid. In the embodiment illustrated in FIG. 28, the extended working channel 790 is formed from a material that is a good thermal conductor to pull away heat from the distal radiating section 742. A heat sink 791 is operably coupled to a proximal end 793 of the extended working channel 790. For example, lumens 719a, 719c (shown in phantom) extend to a proximal end of a balun 752 to cool the proximal end 793 of the extended working channel 790. In this particular embodiment, the fluid may flow up to the proximal end of the balun 752 and turn around; this would keep the extended working channel 790 cool at the proximal end 793. Conduction is utilized to move cool air through a distal end of the extending working channel 790 distal to the balun 752 to the cooled proximal end 793 of the extended working channel 790 proximal to the balun 752. Additionally or alternatively, a ceramic paste "CP" may at least partially cover the distal radiating section 742 and may serve as a dielectric buffer to provide static cooling of the distal radiating section 742. Use of the ceramic paste "CP" may allow the extended working channel 790 to be formed without the lumens 719a, 719c, which, in turn, would allow the extended working channel 790 to remain flexible while providing static cooling and/or buffering.

Figure 29:
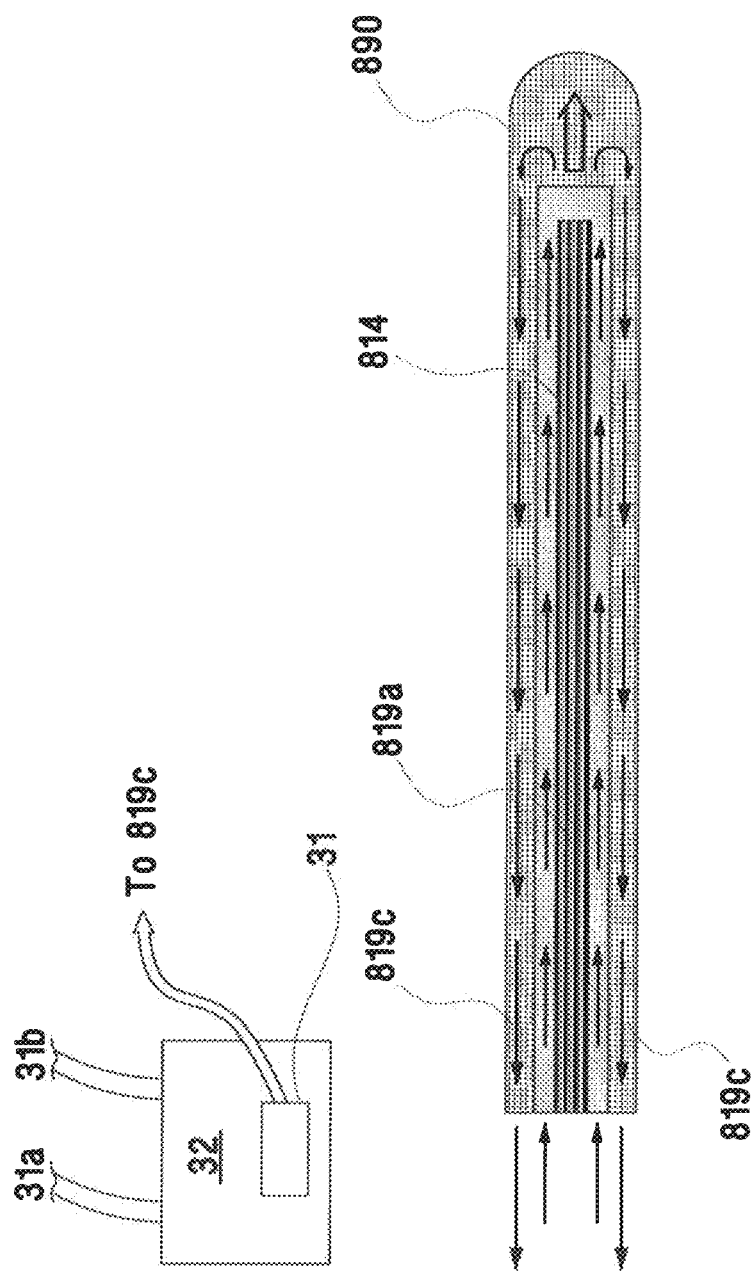
FIG. 29 is a schematic, plan view illustrating a circulation feedback loop that is configured for use with the extended working channels shown in FIGS. 15A, 17 and 21, and the microwave ablation catheter shown in FIGS. 1, 24 and 27-28.

FIG. 29 illustrates an extended working channel 890 according to an embodiment of the present disclosure. By using a vacuum pump to pull water through a the extended working channel 890, the boiling point of the water circulating through the extended working channel 890 can be lowered. At this pressure water boils at about body temperature and the boiling water will rapidly vaporize and the change of phase results in cooling of the fluid and components adjacent to it and create an additional cooling effect for an ablation catheter 814. To this end, a vacuum pump 33 operably couples to a fluid return port (not shown) on the extended working channel to pressurize a fluid circulating through lumens 819c for lowering a boiling point of the fluid circulating through the lumens 819c. In embodiments, an air-mist mixture may be utilized as the cooling medium and circulated through the lumens 819a, 819c; this embodiment takes advantage of the large energy needed to change phase from liquid to vapor, even where temperature remains constant.

Figure 30:
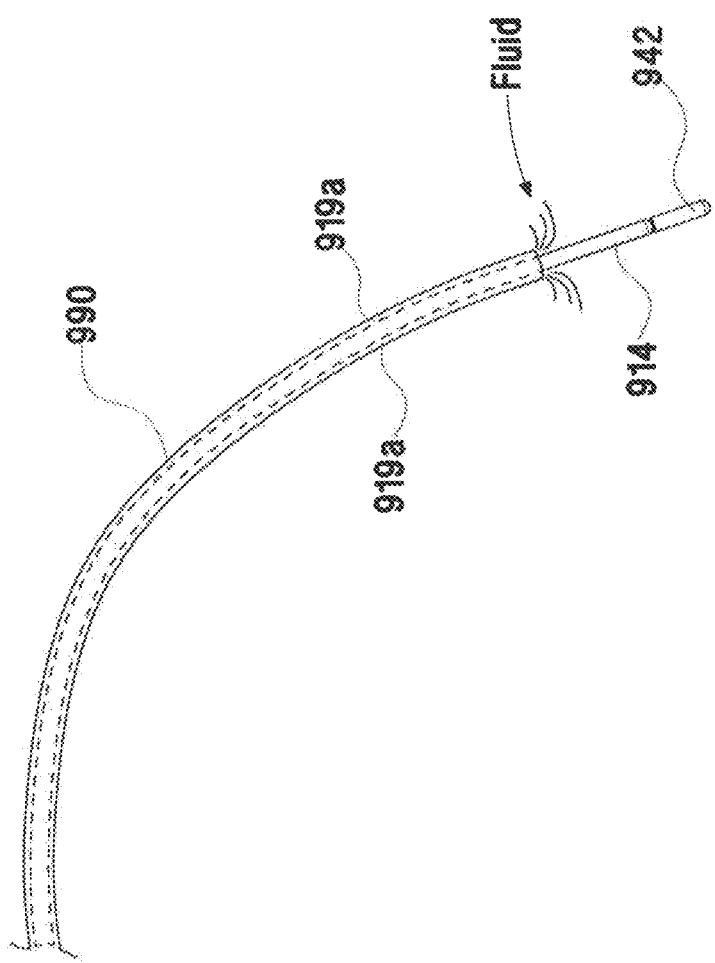
FIG. 30 is a schematic, plan view of still yet another embodiment of the extended working channel shown in FIG. 15A.

FIG. 30 illustrates an extended working channel 990. The extended working channel 990 may include a two lumen configurations (not explicitly shown). In this embodiment, one lumen is dedicated for communication with a fluid intake port (not shown) of the extended working channel 990 and one lumen dedicated to support the ablation catheter 914. Unlike the previous disclosed lumen configurations, the fluid intake port and the lumen are configured for an open loop cooling protocol. The open loop cooling protocol may improve fluid flow within the extended working channel 990. Moreover, energy delivery and microwave energy absorption may be improved by hydrating the target. Further, the open loop cooling protocol may be combined with expandable balloon "B" and/or expandable balun 252 to lock the extended working channel 990 in place, which, in turn, may increase dielectric buffering around the distal radiating section 942.

In embodiments, the extended working channel 990 may include a fluid return port and a corresponding third lumen that is configured to provide suction for suctioning the cooling fluid dispensed from the extended working channel 990; this may provide a user with the ability to perform a Bronchoalveolar Lavage (BAL) at the end of the microwave ablation procedure, i.e., by stopping fluid flow and sucking the fluid back to retrieve one or more tissue samples.

Figure 31:
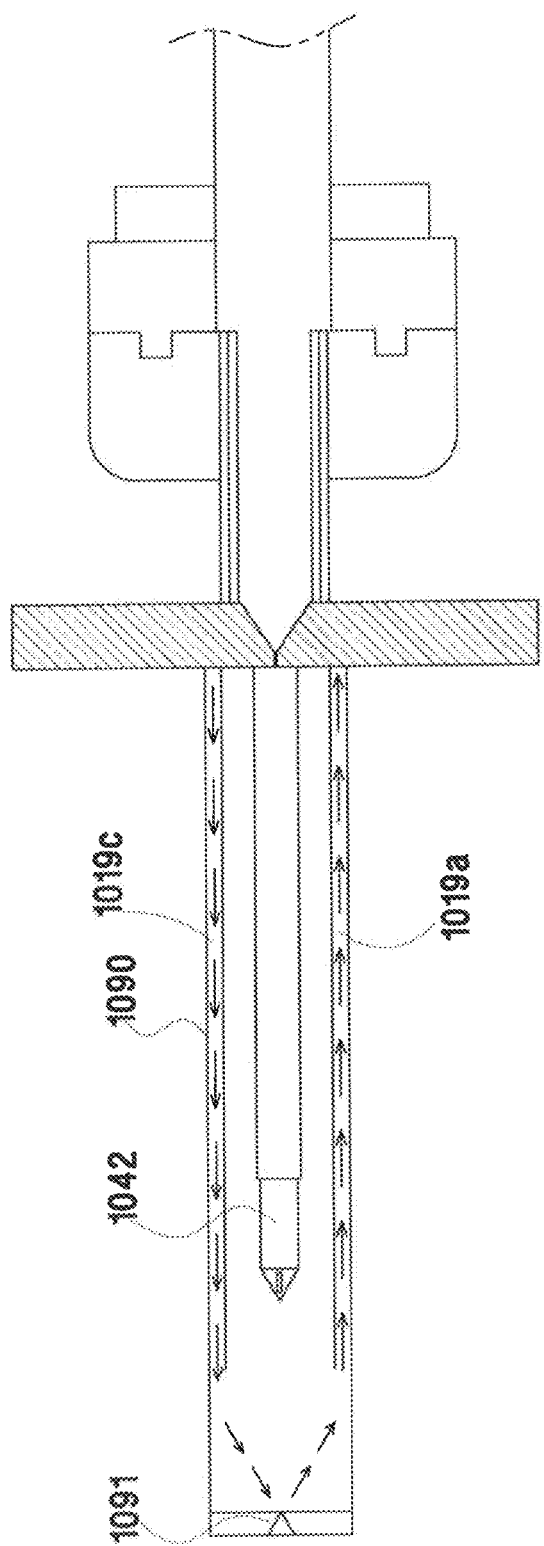
FIG. 31 is a schematic, plan view of still yet another embodiment of the extended working channel shown in FIG. 15A with the microwave ablation catheter shown in FIG. 2 in a retracted configuration.
Figure 32:
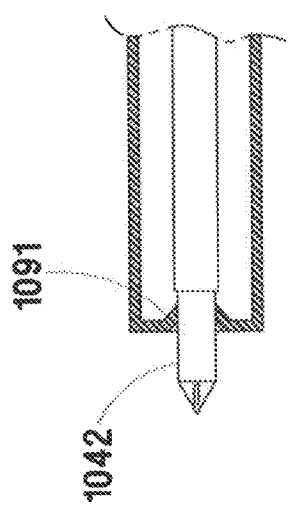
FIG. 32 is a schematic, plan view of the extended working channel shown in FIG. 31 with the microwave ablation catheter shown in an extended configuration.

FIGS. 31-32 illustrate an extended working channel 1090 according to another embodiment of the present disclosure. In this embodiment, the extended working channel 1090 may be utilized as a thermal and electrical control by extending the distal radiating section 1042 through a seal structure 1091 that is provided at a distal end of the extended working channel 1090. The seal structure 1091 is configured for sealed engagement with the distal radiating section 1042 to maintain a fluid tight seal when the distal radiating section 1042 is extended therethrough for treating tissue.

Figure 33:
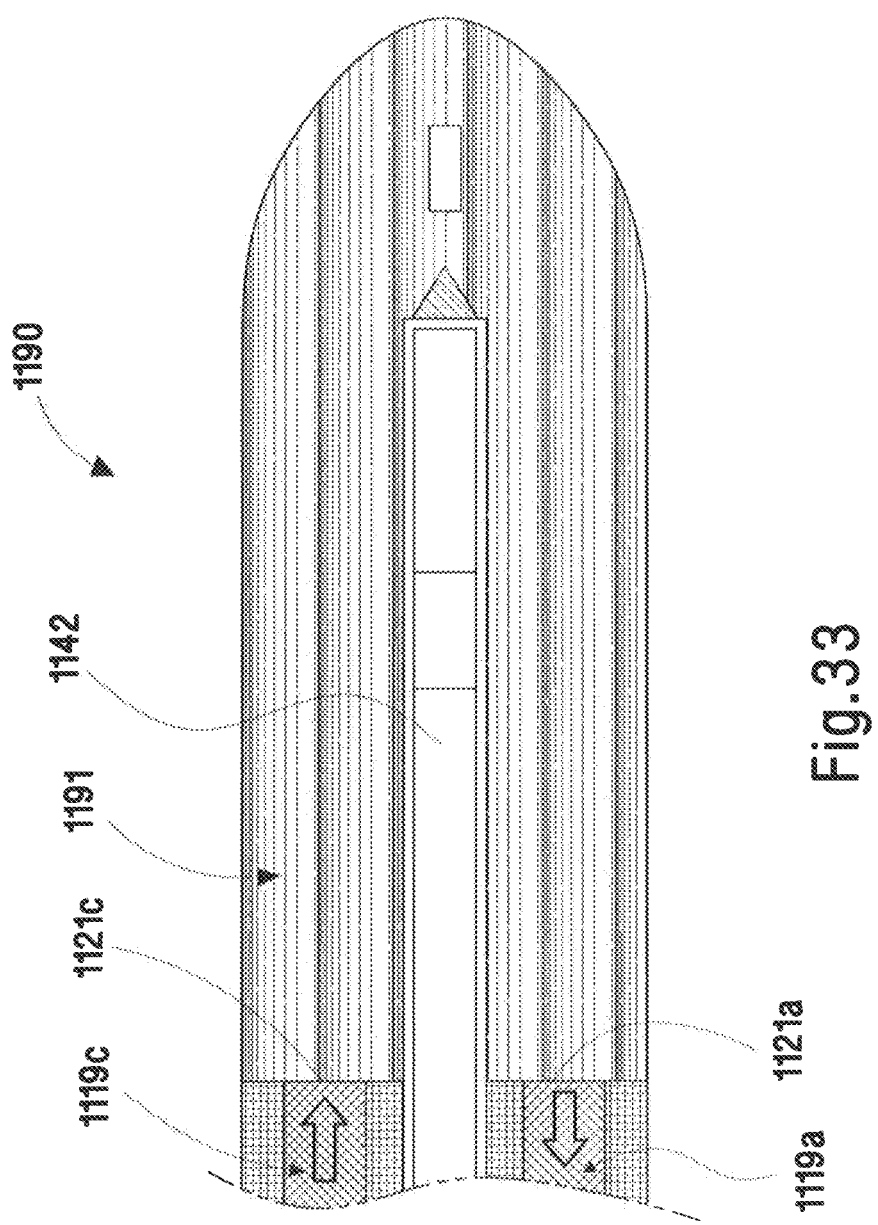
FIG. 33 is a schematic, plan view of still yet another embodiment of the extended working channel shown in FIG. 15A.

FIG. 33 illustrates an extended working channel 1190 according to another embodiment of the present disclosure. In this embodiment, no flow fluid buffering is utilized to cool the distal radiating section 1142. With this purpose in mind, a chamber 1191 is provided at a distal end of the extended working channel 1190 and is not in fluid communication with lumens 1119a, 1119c. The chamber 1191 surrounds the distal radiating section 1142 and configured to receive a high boiling point liquid (e.g., water, saline, etc.) being therein to cool the distal radiating section 1142. In this embodiment seal members 1121a, 1121b may be optionally provided at distal ends of the lumens 1119a, 1119c and are configured to maintain the high boiling point liquid within the chamber 1191. The higher boiling point liquid in changer 1191 absorbs heat generated by the distal radiating section 1142 and transfers it to the fluid circulated through lumens 1119a and 1119c.

Figure 35:
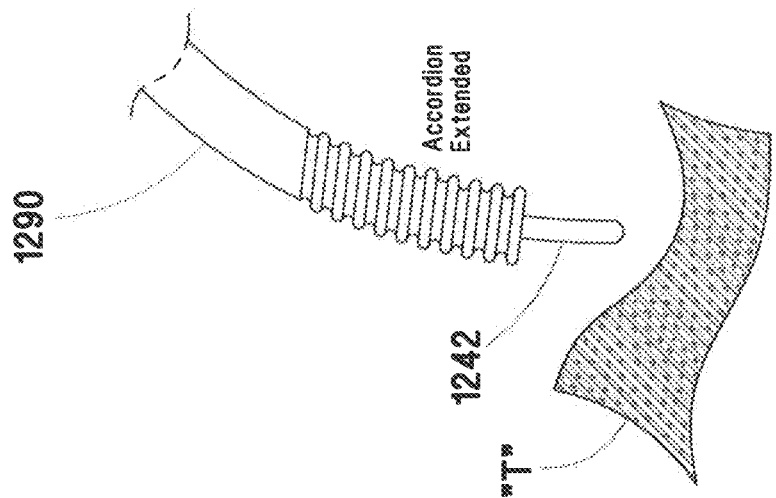
FIG. 35 is a schematic, plan view of the extended working channel shown in FIG. 34 in an expanded configuration.
Figure 34:
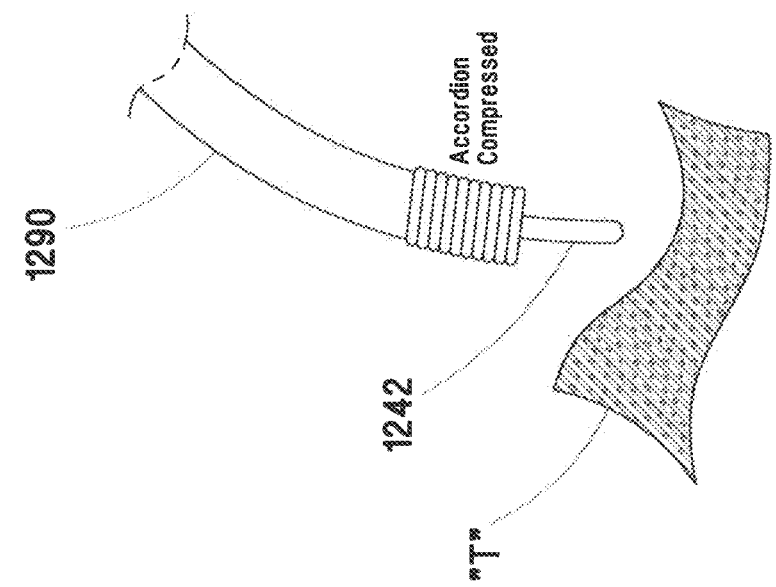
FIG. 34 is a schematic, plan view of still yet another embodiment of the extended working channel shown in FIG. 15A with the extended working channel shown in a non-expanded configuration.

FIGS. 34 and 35 illustrate an extended working channel 1290 according to another embodiment of the instant disclosure. In this embodiment, a heat sink 1291 having an accordion configuration is coupled to a distal end of the extended working channel 1290. The heat sink 1291 is configured to couple to the distal radiating section 1242 via one or more suitable coupling methods when the distal radiating section 1242 is extended through the extended working channel 1290. In the illustrated embodiment, for example, a seal (not shown) may be provided at a distal end of the extended working channel 1290 and may be configured to releasably engage (via a press or friction fit) the distal radiating section 1242 as the distal radiating section is extended from the extended working channel 1290 (FIG. 34). As the heat sink heats, it begins to extend distally away from the extended working channel 1290 bringing the distal radiating section 1242 coupled thereto with it. In the extended configuration, the distal radiating section 1242 will have been moved away from surrounding tissue, which, in turn, may reduce collateral damage to the surrounding tissue (FIG. 35).

Figure 36B:
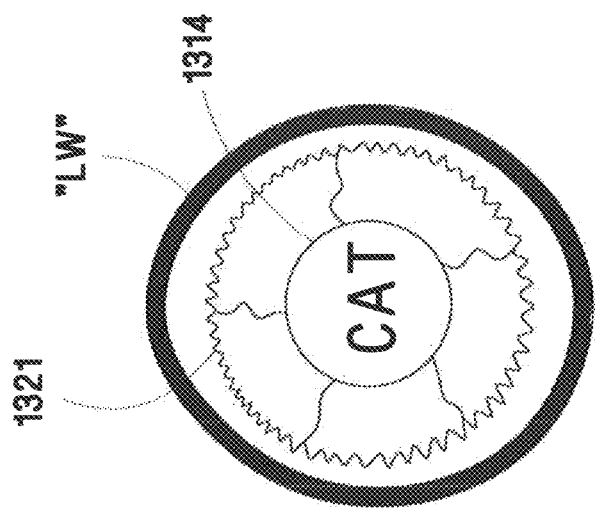
FIG. 36B is a front view of the microwave catheter shown in FIG. 36A with the conductive balloon shown in an inflated configuration.
Figure 36A:
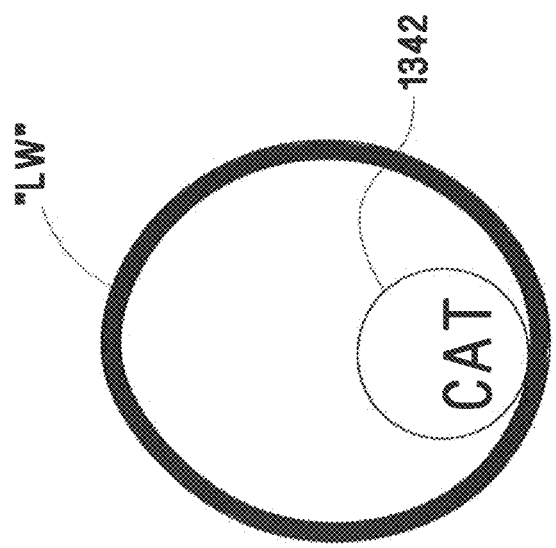
FIG. 36A is a front view of an alternate embodiment of the microwave ablation catheter shown in FIG. 2 including a conductive balloon coupled thereto and shown in a deflated configuration.

FIGS. 36A and 36B illustrate an ablation catheter 1314 according to an embodiment of the instant disclosure. In the embodiment illustrated in FIGS. 36A and 36B, a heat sink is created with the walls of a lung ("LW"), which, typically, include a temperature in the range of about 37° C. To this end, a thermally conductive balloon 1321 is positioned adjacent a distal radiating section (not explicitly shown) of the ablation catheter 1314 and is expandable (via one or more of the aforementioned lumen configurations) to dissipate heat from the distal radiating section into the wall of a lung "LW" of patient. Specifically, when the distal radiating section is energized, the conductive balloon 1321 is inflated and expands into contact with the wall of the lung "LW," which, in turn sinks the heat absorbed by the thermally conductive balloon 1321.

Figure 37B:
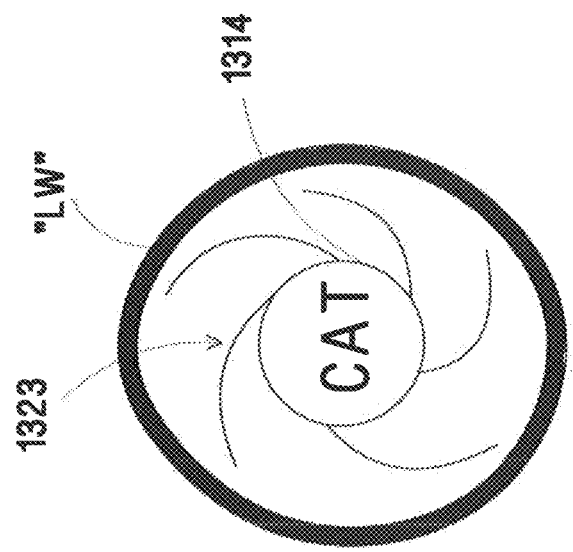
FIG. 37B is a front view of the microwave catheter shown in FIG. 37A with the plurality of thermally conductive fins shown in a deployed configuration.
Figure 37A:
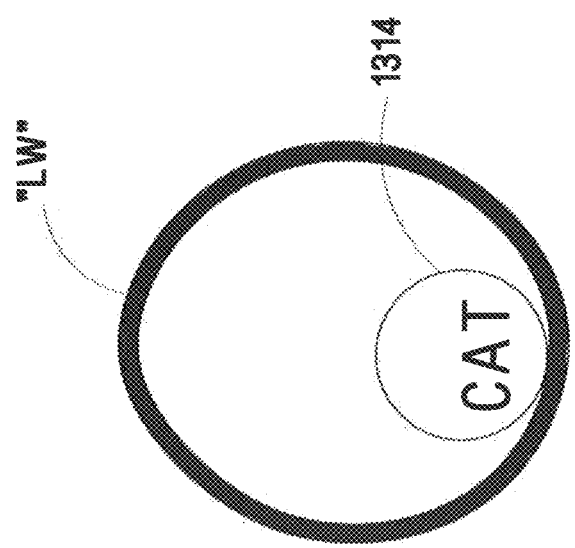
FIG. 37A is a front view of an alternate embodiment of the microwave ablation catheter shown in FIG. 2 including a plurality of thermally conductive fins coupled thereto and shown in a non-deployed configuration.

Alternatively, a plurality of thermally conductive fins 1323 (FIGS. 37A-37B) may be positioned adjacent the distal radiating section. In this embodiment, the fins 1323 are expandable to absorb and dissipate heat from the distal radiating section when the distal radiating section is energized. In the embodiment illustrated in FIGS. 37A-37B, the fins 1323 are formed from a shape memory metal that is configured to move to an expanded configuration when heated as a result of the distal radiating section being energized. Once expanded, airflow may be introduced into the bronchus and across the plurality of thermally conductive fins 1323 to cool the conductive fins 1323, which, in turn, will cool the distal radiating section.

Figure 38:
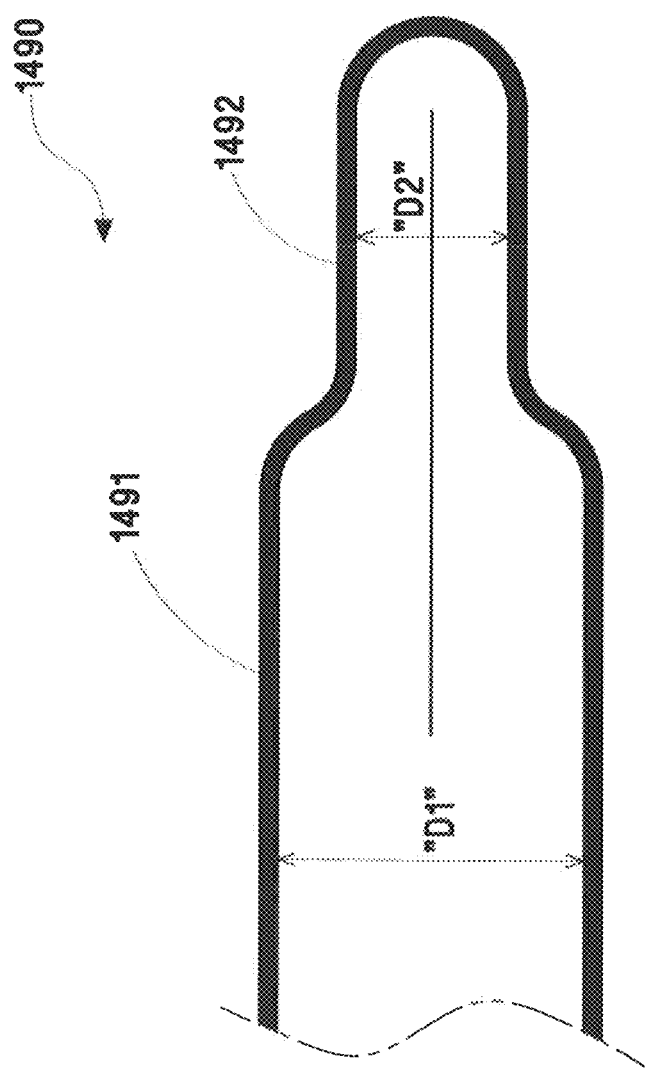
FIG. 38 is a schematic, plan view of still yet another embodiment of the extended working channel shown in FIG. 15A.

FIG. 38 illustrates an extended working channel 1490 according to an embodiment of the instant disclosure. In this embodiment, the extended working channel 1490 includes a proximal end 1491 including a diameter "D1" that is larger than a tapered distal end 1492 that includes a diameter "D2." The larger diameter D1 of the proximal end 1491 allows for more cooling for a given length of extended working channel 1490. In accordance with the instant disclosure, the diameter "D1" of the proximal end 1491 should be large enough to minimize coolant pressure drop but small enough to fit in airways.

FIGS. 39A-39B illustrate an ablation catheter 1514 according to an embodiment of the instant disclosure. Specifically, a balloon 1515 may be positioned adjacent the radiating section 1542 (and/or the balun not shown) and may be in fluid communication with the lumens (not explicitly shown) within the ablation catheter 1514. The balloon 1515 is movable from a deflated configuration (FIG. 39A) for extending the ablation catheter 1514 through an extended working channel 1590 to an inflated configuration (FIG. 39B). In the inflated configuration, the balloon 1515 may serve to expand a buffering volume, i.e., there is more volume to heat. Moreover, the balloon 1515 may be configured to anchor the distal radiating section 1542 in an airway of the lung. Further, the balloon 1515 may be configured to increase flow rate around the balun of the ablation catheter 1514.

III. Sensor Feedback

The following embodiments are configured to provide sensor and/or visual feedback to the system 10 or physician relating device placement (e.g., the extended working channel 90/190, the catheter assembly 12 and/or the ablation catheter 14), tissue environment, ablation progress, device performance, safety, etc.

Figure 40B:
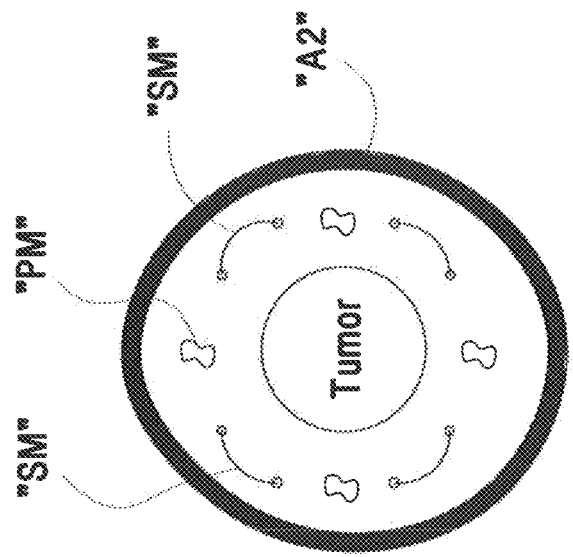
FIG. 40B is a schematic, plan view of the fiducial markers shown in FIG. 40A, wherein the fiducial markers are shown adjacent target tissue that has been ablated.
Figure 40A:
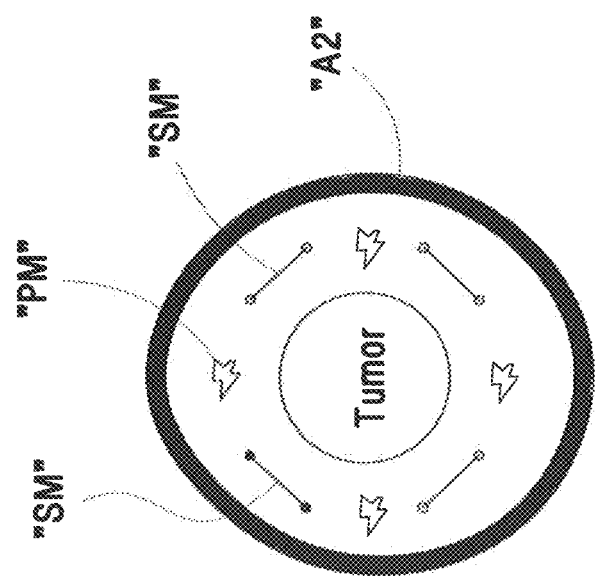
FIG. 40A is a schematic, plan view of various fiducial markers configured for use with the microwave ablation system shown in FIG. 7, wherein the fiducial markers are shown adjacent target tissue that has not been ablated.

In accordance with the instant disclosure, one or more feedback mechanisms may be utilized with the instant disclosure. For example, FIGS. 40A-40B illustrate various fiducial markers that may be detectable by the system 10. Any of the aforementioned extended working channels that include an open distal end, e.g., the working channel 90, may be utilized as a conduit for the placement of one or more fiducial markers within the patient following removal of the locatable guide 86. These markers can be used for a variety of purposes including identifying tumors and lesions for follow-up analysis and monitoring, to identify locations that biopsy sampling has been undertaken, and to identify the boundaries or the center of a tumor or lesion for application of treatment. Other uses will be understood by those of skill in the art as falling within the scope of the present disclosure.

In embodiments, the fiducial markers may be formed from a shape memory alloy "SM." In this embodiment, the fiducial markers "SM" are configured to change shape when heated to a predetermined temperature. Additionally or alternatively, the fiducial markers may be formed from poloxamers "PM." Poloxamers can be transformed from liquid to solid using energy from the distal radiating section of the ablation catheter, e.g., distal radiating section 42. Once in the body, the fiducial markers "PM" cool to body temp and transform back to liquid and are dissolved in the bloodstream. In solid form, the fiducial markers "PM" may be visible under CT, ultrasound, and other imaging modalities to reveal the real time growth of the ablation zone "AZ."

Figure 41:
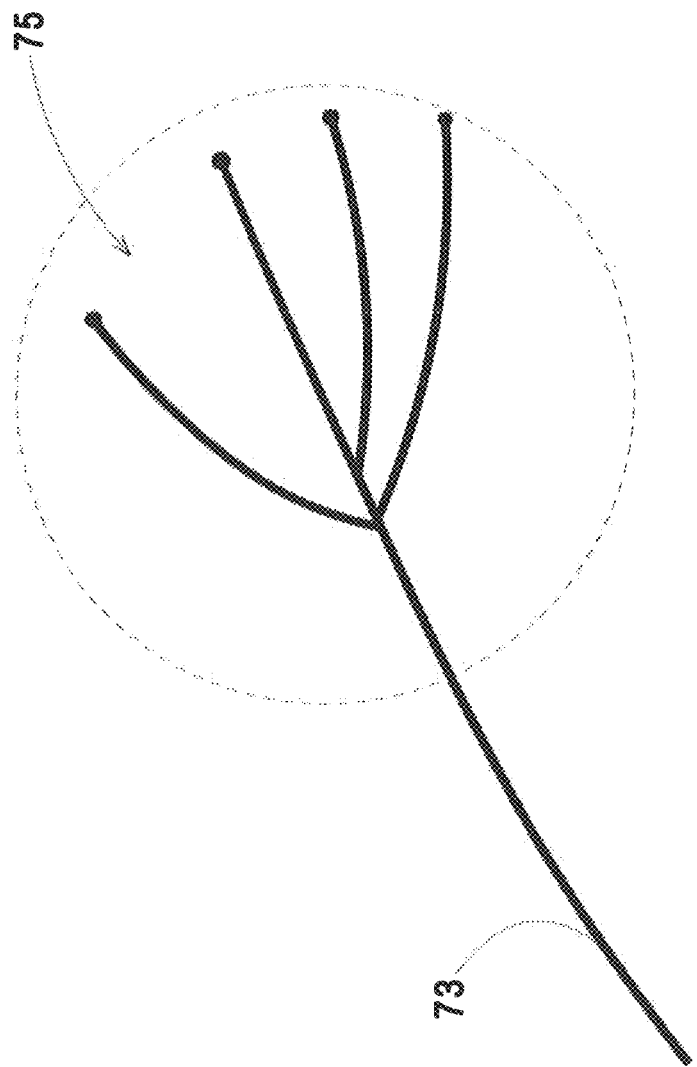
FIG. 41 is a schematic, plan view of a guide wire including a plurality of thermocouples configured for use with the microwave ablation system shown in FIG. 7.

FIG. 41 illustrates another feedback mechanism that may be utilized with the system 10. In this embodiment, a guide wire 73 that is positionable within one of the aforementioned extended working channels (e.g., the extended working channel 90) and deployable therefrom may be utilized for measuring a temperature of the aforementioned distal radiating sections (e.g., distal radiating section 42). The guide wire 73 includes at least one thermocouple 75 at a distal end thereof. The thermocouples 75 may be configured to capture temperature measurements when deployed from the extended working channel. The thermal couples 75 may be in communication with a microcontroller of the energy source 16 to monitor rate of change of the temperature of or surrounding the distal radiating section 42; the rate of change can be analyzed to correlate with a specific ablation size. In embodiments, the guide wire 73 may be utilized to deploy the ablation catheter 14 from the extended working channel 90.

Figure 42:
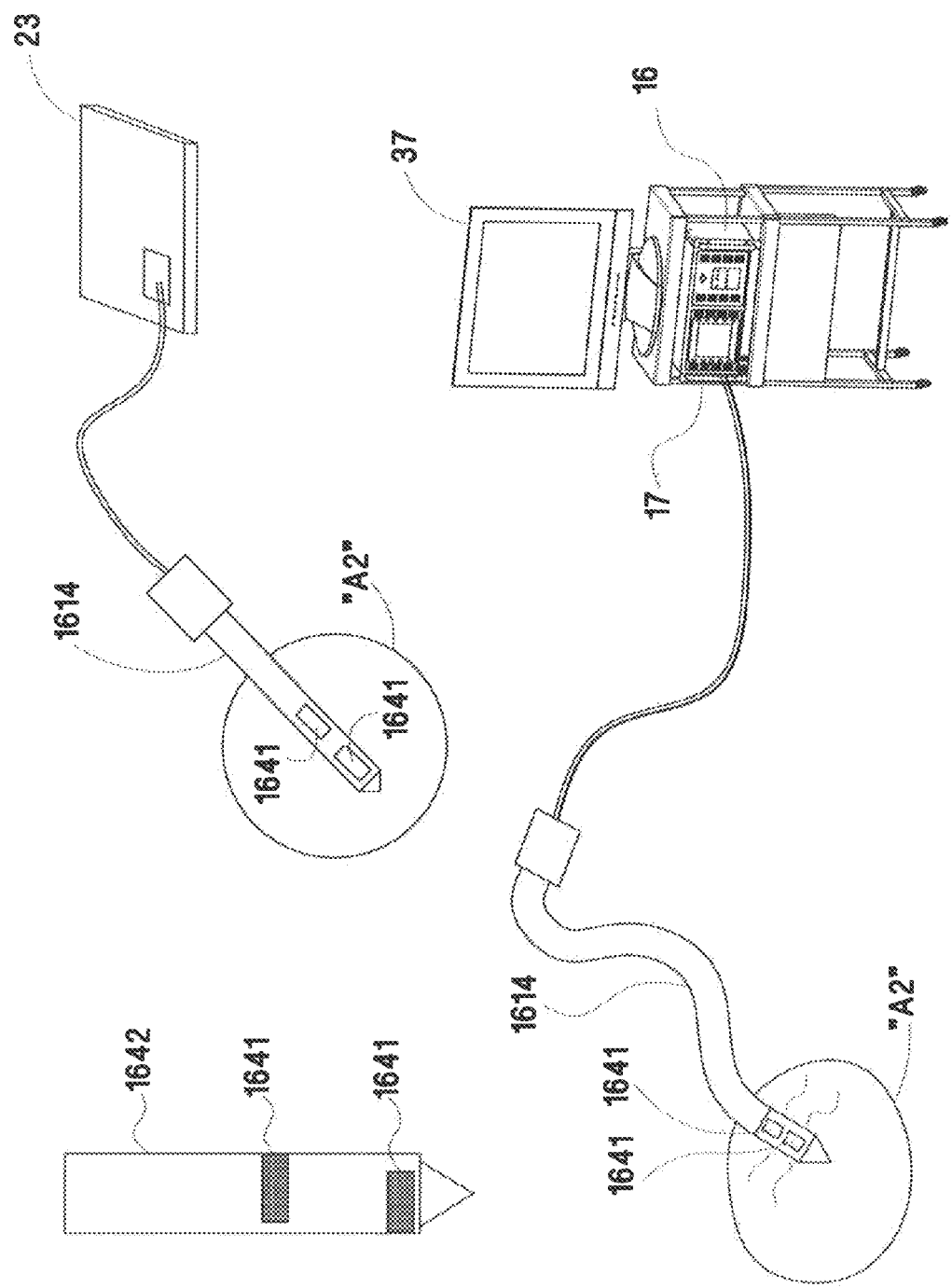
FIG. 42 is a perspective view of an electrical measurement system configured for use with the microwave ablation system shown in FIG. 7.
Figure 43:
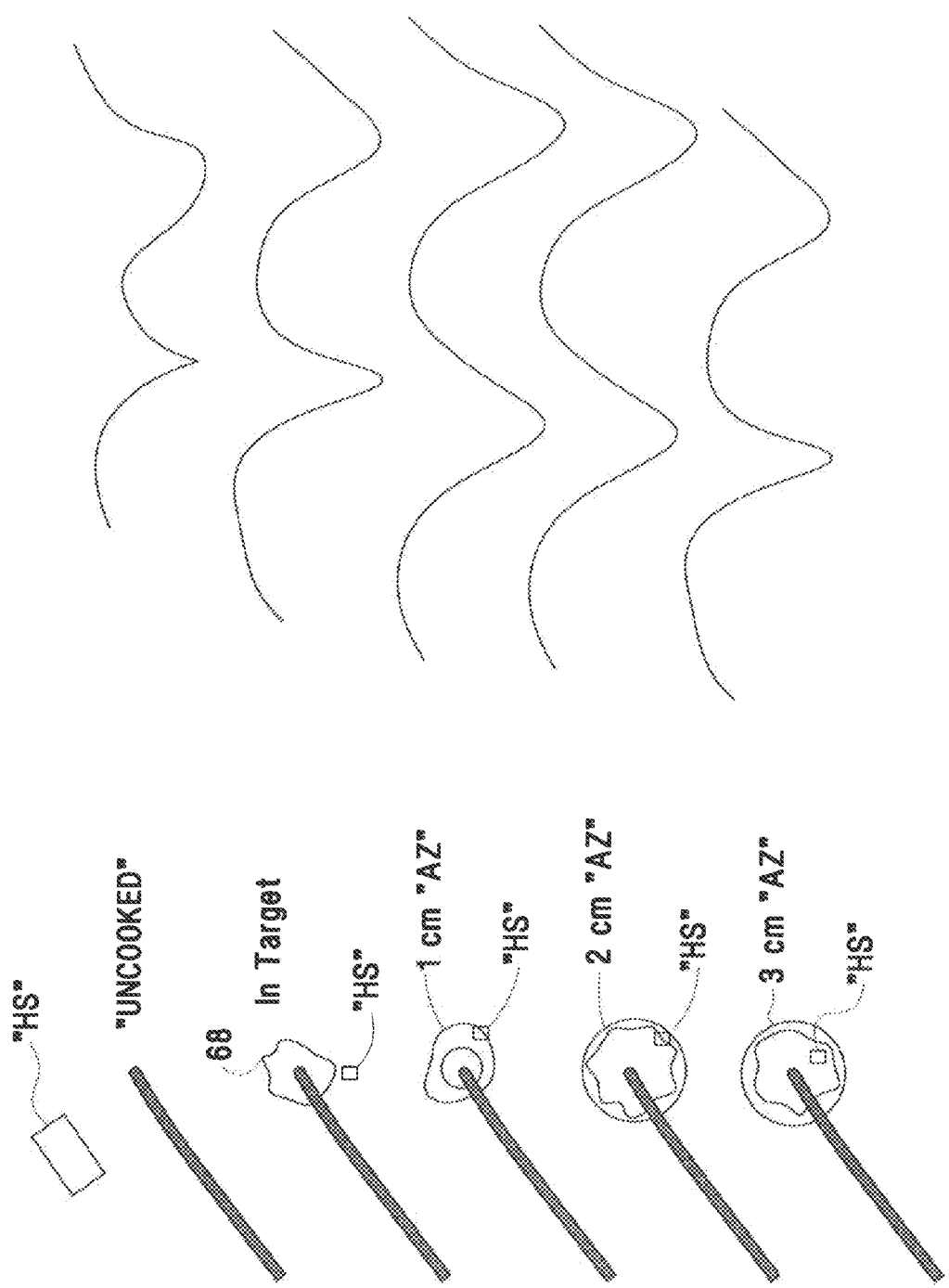
FIG. 43 is a schematic, plan view of a feedback configuration configured for use with the microwave ablation system shown in FIG. 7.

FIGS. 42-43 illustrate another feedback mechanism that may be utilized with the system 10. In the embodiment illustrate in FIG. 42, the system 10 is capable of detecting placement of an ablation catheter 1642 in healthy vs. tumor tissue or if bleeding occurs along the ablation catheter 1642. With this purpose in mind, one or more electrodes 1641 (two electrodes 1641 shown in FIG. 42) are provided adjacent a distal radiating section 1642 and are configured to detect data pertaining to the target tissue prior to, during or after activation of the distal radiating section 1642. The data pertaining to tissue may include electrical properties of the tissue, e.g., RF impedance.

In embodiments, the electrodes 1641 can be utilized to capture dielectric measurements of the surrounding tissue to ensure placement in tumor tissue. The amount and type of buffering of the distal radiating section 1642 will play a role in how well the electrodes 1641 can capture these measurements. With either of the RF or dielectric measurement types, a controller 17 (or another system 23, e.g., a laptop) connected to the ablation catheter 1614 will be needed to capture and analyze the data to interpret to the user. After the data is analyzed, the controller 17 provides the relevant information to a user, e.g., on a display 37.

In embodiments, the controller 17 may be configured to perform S-parameter (FIG. 43) analysis between input and output ports of the microwave energy source. In this embodiment, the S-parameter analysis is utilized to determine ablation size "AZ", to control operation of the energy source 16 and/or to detect damage to the distal radiating section 1642 in real-time.

In embodiments, one or more sensor configurations may be utilized with the system 10. For example, a hydration sensor "HS" (see FIG. 43 for example) may be utilized to measure the water content of the tissue at some distance from distal radiating section 42 to monitor ablation progress and/or completion. In this instance, the extended working channel 90 may be utilized to position the "HS" at a predetermined point away from where the distal radiating section 42 is going to be positioned. As moisture is driven out of the tissue, the sensor "HS" tracks the rate of change and can tell the user when the ablation is complete. Dielectric properties can be directly correlated with hydration levels of the tissue.

Moreover, one or more fiber optic cables "FC" may through the extended working channel 90 for positioning adjacent to target tissue for providing a visual perspective of the target tissue to a clinician. Alternately, the fiber optic cable "FC" may be provided adjacent to the distal radiating section 42 (see FIG. 5 for example). In this embodiment, one or more lenses (not shown) may be provided adjacent to the distal radiating section 42 and coupled to a distal end of the fiber optic cable "FC." Further, one or more force sensor "FS" configured to provide feedback on force being applied by the distal radiating section 42 to penetrate tissue. In this instance, the force sensor "FS" may be operably coupled adjacent the distal radiating section (see FIG. 5 for example).

In embodiments, one or more chemical sensor "CS" may be configured to detect one or ore chemicals of tissue prior to, during or after activation of the distal radiating section 42 (see FIG. 5 for example). In this embodiment, the chemical sensor "CS" may be in operable communication with the microcontroller 17 that is configured to detect chemicals associated with the target tissue, e.g., acids and proteins. The chemicals detected may be correlated to a progression of thermal ablation growth and stored in one or more data look-up tables (not shown) that is accessible to the microcontroller 17.

Figure 44:
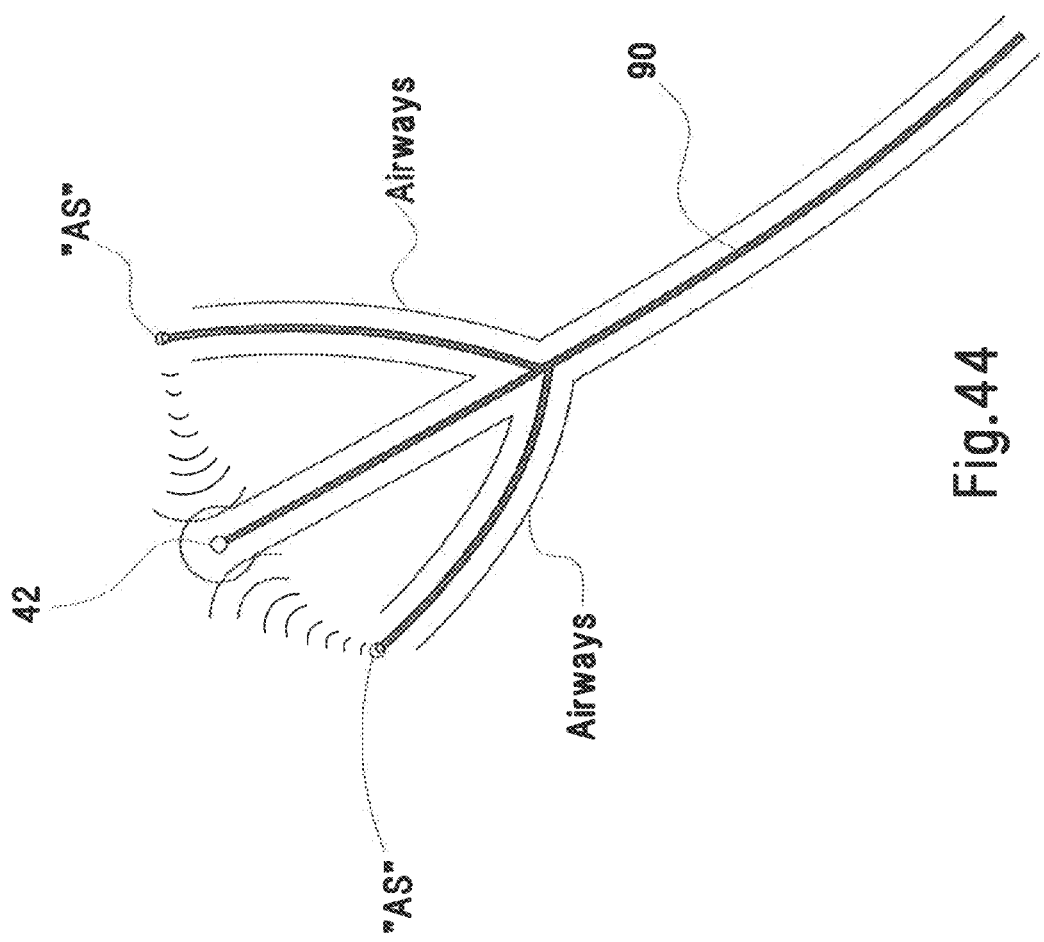
FIG. 44 is a schematic, plan view of an another embodiment of a feedback configuration configured for use with the microwave ablation system shown in FIG. 7.

FIG. 44 illustrates a method of placement configuration for various sensor configurations. Specifically, alternate airways may be utilized to deploy sensors (e.g., acoustic, thermocouples, electrical sensors, etc). In one particular embodiment, the ablation catheter 14 may be extended through the extended working channel 90 and positioned in between two opposing sensors, e.g., acoustic sensors "AS" that are positioned in opposite airways. During operation of the distal radiating section 42, a ping across the airways can be generated to measure tissue properties, e.g., measure impedance, dielectric or temperature.

Figure 45:
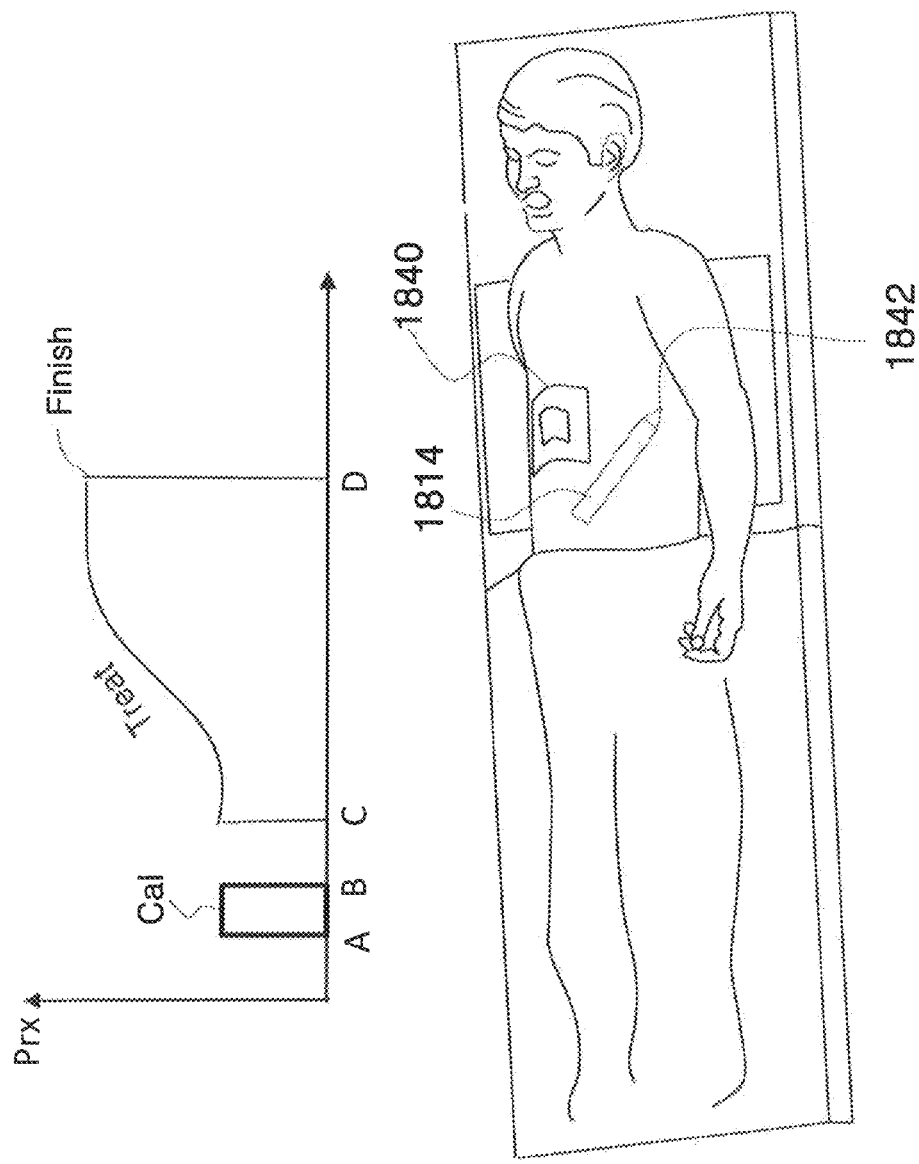
FIG. 45 is schematic, plan view of a yet another embodiment of a feedback configuration configured for use with the microwave ablation system shown in FIG. 7.

FIG. 45 illustrates another feedback mechanism that may be utilized with the system 10. In this embodiment, two antennas for ablation (e.g., procedural/completeness) monitoring are provided, a sensor patch 1840 and a distal radiating section 1842 of an ablation catheter 1814 (shown not positioned within an extended working channel for clarity). Sensor patch 1840 is positionable on a patient and configured to calibrate the ablation catheter 1814 prior to treating tissue and determine when the tissue has been adequately ablated. The sensor patch 1840 is in operable communication with controller 17 configured to monitor the amount of power received by the sensor patch 1840 as the distal radiating section 1842 is energized. The graph indicates received power at the sensor patch 1840 during both calibration (points A-B) and an ablation cycle (points C-D). The calibration cycle baselines transmission path. As ablation progresses, transmission path between distal radiating section 1842 and sensor patch 1840 becomes less lossy due to desiccation resulting in increasing received power. Ablation completeness is determined by amount of increased power received above calibration. For example, 1.5 cm ablation zone "AZ" increases power to sensor patch 1840 by approximately 15%. In an embodiment, when the power at the sensor patch 1840 reaches the calibration level or surpasses the calibration level, the microcontroller 17 automatically shuts power off to ablation catheter 1814.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave ablation system configured for use in luminal network, comprising:
    a microwave energy source;
    a tool for treating tissue, the tool being configured to receive microwave energy from the microwave energy source;
    an extended working channel configured to provide passage for the tool;
    a locatable guide catheter including a position sensor positionable through the extended working channel and configured to navigate the extended working channel adjacent the target tissue; and
    a navigation system for guiding at least one of the tool, extended working channel or the locatable guide through a luminal network following a predetermined determined pathway to the target tissue.

2. The microwave ablation system according to claim 1, further including a bronchoscope configured to receive the extended working channel for providing access to the luminal network.

3. The microwave ablation system according to claim 1, wherein the tool is selected from the group consisting of a microwave ablation catheter, a biopsy brush, needle brushes and biopsy forceps.

4. The microwave ablation system according to claim 3, wherein the microwave ablation catheter comprises:
    a coaxial cable connected at a proximal end of the coaxial cable to a microwave energy source and at a distal end of the coaxial cable to a distal radiating section, the coaxial cable including inner and outer conductors and a dielectric positioned therebetween, the inner conductor extending distally past the outer conductor and in sealed engagement with the distal radiating section; and
    a balun formed in part from a conductive material electrically connected to the outer conductor of the coaxial cable and extending along at least a portion of the coaxial cable, the conductive material having a braided configuration and covered by at least one insulative material.

5. The microwave ablation catheter according to claim 4, further including a multi-lumen housing that is configured to receive the ablation catheter.

6. The microwave ablation catheter according to claim 5, wherein the multi-lumen housing includes a hub at a proximal end thereof, the hub including a plurality of ports.

7. The microwave ablation catheter according to claim 6, wherein at least one of the plurality of ports is an electrical port configured to provide electrical communication between the coaxial cable and the microwave energy source, and wherein at least two of the plurality of ports are a fluid intake port and a fluid return port configured to provide respective ingress and egress of a coolant to and from the multi-lumen housing for cooling the distal radiating section of the coaxial cable.

8. The microwave ablation catheter according to claim 7, wherein the multi-lumen housing includes a four lumen configuration having two lumens dedicated for communication with a respective one of the fluid intake and return ports and two lumens dedicated to support the coaxial cable including the balun.

9. The microwave ablation catheter according to claim 8, wherein the multi-lumen housing includes a five lumen configuration having four lumens two of which being dedicated for communication with the fluid intake port and two of which being dedicated for communication with the fluid return port and one lumen designated to support the coaxial cable including the balun.

10. The microwave ablation system according to claim 4, wherein the extended working channel includes a closed distal end.

11. The microwave ablation system according to claim 10, wherein the extended working channel includes a multi-lumen configuration and is configured to receive the ablation catheter.

12. The microwave ablation system according to claim 11, wherein the extended working channel includes hub at a proximal end thereof, the hub including a plurality of ports.

13. The microwave ablation system according to claim 12, wherein at least two of the plurality of ports are a fluid intake port and a fluid return port configured to provide respective ingress and egress of a coolant to and from the extended working channel for cooling the distal radiating section of the coaxial cable.

14. The microwave ablation system according to claim 13, wherein the extended working channel includes one of:
a three lumen configuration having two lumens dedicated for communication with a respective one of the fluid intake and return ports and one lumen dedicated to support the coaxial cable including the balun;
a four lumen configuration having two lumens dedicated for communication with a respective one of the fluid intake and return ports and two lumens dedicated to support the coaxial cable including the balun; and
a five lumen configuration having four lumens two of which being dedicated for communication with the fluid intake port and two of which being dedicated for communication with the fluid return port and one lumen designated to receive the ablation catheter.

15. The microwave ablation system according to claim 1, wherein the predetermined pathway is generated based on computed tomographic (CT) data of the luminal network, and is displayed in a generated model.

16. The microwave ablation system according to claim 15, wherein the predetermined pathway is generated from CT data to identify a pathway to a target identified by a user in the CT data, and the pathway is generated for acceptance by the user before use in the navigation system.

17. A microwave ablation system configured for use in luminal network, comprising:
a microwave energy source;
a tool for treating tissue, the tool receiving microwave energy from the microwave energy source;
an extended working channel configured to provide passage for the tool;
a locatable guide catheter including a position sensor positionable through the extended working channel and configured to navigate the extended working channel adjacent the target tissue; and
at least one imaging modality for confirming placement of the tool within target tissue.

18. The microwave ablation system according to claim 17, further including a bronchoscope configured to receive the extended working channel for providing access to the luminal network.

19. The microwave ablation system according to claim 18, wherein the tool is selected from the group consisting of a microwave ablation catheter, a biopsy brush, needle brushes and biopsy forceps.

20. The microwave ablation system according to claim 19, wherein the microwave ablation catheter comprises:
a coaxial cable connected at a proximal end of the coaxial cable to a microwave energy source and at a distal end of the coaxial cable to a distal radiating section, the coaxial cable including inner and outer conductors and a dielectric positioned therebetween, the inner conductor extending distally past the outer conductor and in sealed engagement with the distal radiating section; and
a balun formed in part from a conductive material electrically connected to the outer conductor of the coaxial cable and extending along at least a portion of the coaxial cable, the conductive material having a braided configuration and covered by at least one insulative material.

21. The microwave ablation catheter according to claim 20, further including a multi-lumen housing that is configured to receive the ablation catheter.

22. The microwave ablation catheter according to claim 21, wherein the multi-lumen housing includes a hub at a proximal end thereof, the hub including a plurality of ports.

23. The microwave ablation catheter according to claim 22, wherein at least one of the plurality of ports is an electrical port configured to provide electrical communication between the coaxial cable and the microwave energy source, and wherein at least two of the plurality of ports are a fluid intake port and a fluid return port configured to provide respective ingress and egress of a coolant to and from the multi-lumen housing for cooling the distal radiating section of the coaxial cable.

24. The microwave ablation catheter according to claim 23, wherein the multi-lumen housing includes a three lumen configuration having two lumens dedicated for communication with a respective one of the fluid intake and return ports and one lumen dedicated to support the coaxial cable including the balun.

25. The microwave ablation catheter according to claim 24, wherein the multi-lumen housing includes a five lumen configuration having four lumens two of which being dedicated for communication with the fluid intake port and two of which being dedicated for communication with the fluid return port and one lumen designated to support the coaxial cable including the balun.

26. The microwave ablation system according to claim 17, wherein the extended working channel includes a closed distal end.

27. The microwave ablation system according to claim 26 wherein the extended working channel includes a multi-lumen configuration and is configured to receive the ablation catheter.

28. The microwave ablation system according to claim 27, wherein the extended working channel includes hub at a proximal end thereof, the hub including a plurality of ports.

29. The microwave ablation system according to claim 28, wherein the extended working channel includes one of:
a three lumen configuration having two lumens dedicated for communication with a respective one of the fluid intake and return ports and one lumen dedicated to support the coaxial cable including the balun;
a four lumen configuration having two lumens dedicated for communication with a respective one of the fluid intake and return ports and two lumens dedicated to support the coaxial cable including the balun; and
a five lumen configuration having four lumens two of which being dedicated for communication with the fluid intake port and two of which being dedicated for communication with the fluid return port and one lumen designated to receive the ablation catheter.

30. The microwave ablation system according to claim 17, wherein the at least one imaging modality is selected from the group consisting of computer tomography, ultrasound and fluoroscopy.

31. The microwave ablation system according to claim 30, wherein computer tomography data is manipulated, by a computer, to create a virtual fluoroscopic image that identifies the target tissue.

32. The microwave ablation system according to claim 31, wherein the virtual fluoroscopic image is generated, by the computer, for comparison with a live fluoroscopic image to provide a user with the ability to compare placement of the extended working channel and microwave ablation catheter within target tissue.

* * * * *